(12) United States Patent
Ju et al.

(10) Patent No.: US 10,689,412 B2
(45) Date of Patent: Jun. 23, 2020

(54) DNA SEQUENCING BY SYNTHESIS USING RAMAN AND INFRARED SPECTROSCOPY DETECTION

(71) Applicants: Jingyue Ju, Englewood Cliffs, NJ (US);
Jian Wu, New York, NY (US);
Zengmin Li, Flushing, NY (US)

(72) Inventors: Jingyue Ju, Englewood Cliffs, NJ (US);
Jian Wu, New York, NY (US);
Zengmin Li, Flushing, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 284 days.

(21) Appl. No.: 15/490,823

(22) Filed: Apr. 18, 2017

(65) Prior Publication Data
US 2017/0283451 A1    Oct. 5, 2017

Related U.S. Application Data

(62) Division of application No. 14/119,846, filed as application No. PCT/US2012/039198 on May 23, 2012, now Pat. No. 9,624,539.

(60) Provisional application No. 61/489,191, filed on May 23, 2011.

(51) Int. Cl.
| C12Q 1/68 | (2018.01) |
| C07H 19/06 | (2006.01) |
| C07H 19/16 | (2006.01) |
| C12Q 1/6827 | (2018.01) |
| C12Q 1/6869 | (2018.01) |
| C07H 21/00 | (2006.01) |
| C12Q 1/6874 | (2018.01) |

(52) U.S. Cl.
CPC .............. *C07H 19/06* (2013.01); *C07H 19/16* (2013.01); *C07H 21/00* (2013.01); *C12Q 1/6827* (2013.01); *C12Q 1/6869* (2013.01); *C12Q 1/6874* (2013.01); *C12Q 2525/101* (2013.01); *C12Q 2533/101* (2013.01); *C12Q 2565/632* (2013.01)

(58) Field of Classification Search
CPC ....... C07H 19/06; C07H 19/16; C12Q 1/6869
USPC .......................................... 536/4.1; 435/6.1
See application file for complete search history.

(56) References Cited

U.S. PATENT DOCUMENTS

| 5,804,386 A | 9/1998 | Ju |
| 5,814,454 A | 9/1998 | Ju |
| 5,876,936 A | 3/1999 | Ju |
| 5,952,180 A | 9/1999 | Ju |
| 6,046,005 A | 4/2000 | Ju et al. |
| 6,495,680 B1 | 12/2002 | Gong |
| 6,627,748 B1 | 9/2003 | Ju et al. |

(Continued)

FOREIGN PATENT DOCUMENTS

| WO | WO 2015/123430 | 8/2015 |
| WO | WO 2015/148402 | 10/2015 |

(Continued)

OTHER PUBLICATIONS

May 11, 2016 Restriction Requirement issued in connection with U.S. Appl. No. 14/119,846, Ju et al.

(Continued)

*Primary Examiner* — Jezia Riley
(74) *Attorney, Agent, or Firm* — John P. White; Gary J. Gershik; Cooper & Dunham LLC

(57) ABSTRACT

This invention provides a process of labeling a polynucleotide analogue to be detected by Raman and/or infrared spectroscopy detection.

13 Claims, 26 Drawing Sheets

Specification includes a Sequence Listing.

(56) References Cited

U.S. PATENT DOCUMENTS

| | | | |
|---|---|---|---|
| 6,664,079 | B2 | 12/2003 | Ju et al. |
| 7,074,597 | B2 | 7/2006 | Ju |
| 7,345,159 | B2 | 3/2008 | Ju et al. |
| 7,635,578 | B2 | 12/2009 | Ju et al. |
| 7,713,698 | B2 | 5/2010 | Ju et al. |
| 7,790,869 | B2 | 9/2010 | Ju et al. |
| 7,883,869 | B2 | 2/2011 | Ju et al. |
| 7,982,029 | B2 | 7/2011 | Ju et al. |
| 8,088,575 | B2 | 1/2012 | Ju et al. |
| 8,298,792 | B2 | 10/2012 | Ju et al. |
| 8,796,432 | B2 | 8/2014 | Ju et al. |
| 8,889,348 | B2 | 11/2014 | Ju |
| 9,115,163 | B2 | 8/2015 | Ju et al. |
| 9,133,511 | B2 | 9/2015 | Ju et al. |
| 9,159,610 | B2 | 10/2015 | Zhang et al. |
| 9,175,342 | B2 | 11/2015 | Ju et al. |
| 9,255,292 | B2 | 2/2016 | Ju et al. |
| 9,297,042 | B2 | 3/2016 | Ju et al. |
| 9,528,151 | B2 | 12/2016 | Ju et al. |
| 9,624,539 | B2 | 4/2017 | Ju et al. |
| 9,670,539 | B2 | 6/2017 | Ju et al. |
| 9,708,358 | B2 | 7/2017 | Ju et al. |
| 9,718,852 | B2 | 8/2017 | Ju et al. |
| 9,719,139 | B2 | 8/2017 | Ju et al. |
| 9,725,480 | B2 | 8/2017 | Ju et al. |
| 9,868,985 | B2 | 1/2018 | Ju et al. |
| 10,000,801 | B2 | 6/2018 | Ju et al. |
| 10,144,961 | B2 | 12/2018 | Ju et al. |
| 10,240,195 | B2 | 3/2019 | Fuller et al. |
| 10,246,479 | B2 | 4/2019 | Ju et al. |
| 10,260,094 | B2 | 4/2019 | Ju et al. |
| 2006/0057565 | A1 | 3/2006 | Ju et al. |
| 2011/0014611 | A1 | 1/2011 | Ju et al. |
| 2012/0142006 | A1 | 6/2012 | Ju et al. |
| 2012/0156680 | A1 | 6/2012 | Ju et al. |
| 2013/0264207 | A1 | 10/2013 | Ju et al. |
| 2015/0111759 | A1 | 4/2015 | Ju et al. |
| 2015/0119259 | A1 | 4/2015 | Ju et al. |
| 2015/0197800 | A1 | 7/2015 | Ju et al. |
| 2015/0368710 | A1 | 12/2015 | Fuller et al. |
| 2016/0024570 | A1 | 1/2016 | Ju et al. |
| 2016/0024574 | A1 | 1/2016 | Ju et al. |
| 2016/0041179 | A1 | 2/2016 | Ju et al. |
| 2016/0208313 | A1 | 7/2016 | Ju et al. |
| 2016/0264612 | A1 | 9/2016 | Ju et al. |
| 2017/0058335 | A1 | 3/2017 | Tao et al. |
| 2017/0101675 | A1 | 4/2017 | Ju et al. |
| 2018/0073071 | A1 | 3/2018 | Ju et al. |
| 2018/0112257 | A1 | 4/2018 | Ju et al. |
| 2018/0201642 | A1 | 7/2018 | Ju et al. |
| 2019/0031704 | A1 | 3/2019 | Ju et al. |
| 2019/0031705 | A1 | 3/2019 | Ju et al. |
| 2019/0031706 | A1 | 3/2019 | Ju et al. |
| 2019/0085014 | A1 | 3/2019 | Ju et al. |
| 2019/0085015 | A1 | 3/2019 | Ju et al. |
| 2019/0085016 | A1 | 3/2019 | Ju et al. |
| 2019/0085388 | A1 | 5/2019 | Ju et al. |
| 2019/0092805 | A1 | 5/2019 | Ju et al. |
| 2019/0092806 | A1 | 5/2019 | Ju et al. |
| 2019/0135850 | A1 | 5/2019 | Ju et al. |
| 2019/0135851 | A1 | 5/2019 | Ju et al. |
| 2019/0136308 | A1 | 5/2019 | Ju et al. |

FOREIGN PATENT DOCUMENTS

| | | |
|---|---|---|
| WO | WO 2016/144973 | 9/2016 |
| WO | WO 2016/154215 | 9/2016 |
| WO | WO2017/058953 | 4/2017 |
| WO | WO2017/087887 | 5/2017 |
| WO | WO2017/176677 | 10/2017 |
| WO | WO2017/176679 | 10/2017 |
| WO | WO2017/205336 | 11/2017 |
| WO | WO2018/183538 | 10/2018 |

OTHER PUBLICATIONS

Amendment in Response to Restriction Requirement, filed Nov. 11, 2016 in connection with U.S. Appl. No. 14/119,846, Ju et al.

Amendment in Response to Examiner's Interview, filed Nov. 30, 2016 in connection with U.S. Appl. No. 14/119,846, Ju et al.

Notice of Allowance dated Dec. 16, 2016 in connection with U.S. Appl. No. 14/119,846, Ju et al.

Bai et al. (2003) "Photocleavage of a 2-nitrobenzyl Linker Bridging a Fluorophore to the 5' end of DNA," PNAS, vol. 100, No. 2, pp. 409-413.

Benson, S.C. et al., (1993) "Heterodimeric DNA-binding dyes designed for energy transfer: stability and applications of the DNA complexes," Nucleic Acids Res. 21:5720-5726.

Bergmann et al. (1995) "Allyl As Internucleotide Protecting Group in DNA Synthesis to be Cleaved Off by Ammonia," Tetrahedron, 51:6971-6976.

Braslavsky I.; Hebert, B.; Kartalov, E.; et al. (2003) "Sequence information can be obtained from single DNA molecules." Proc. Natl. Acad. Sci. 100 (7):3960-3964.

Canard B. et al. (1994) "DNA polymerase fluorescent substrates with reversible 3'-tags," Gene, 148:1-6.

Chee, M. et al. (1996) "Accessing genetic information with high density DNA arrays," Science 274:610-614.

Chen et al. (2010) "Reconstructed evolutionary adaptive paths give polymerases accepting reversible terminators for sequencing and SNP detection" Proc. Natl. Acad. Sci. U.S.A., 107:1948-53.

Crespo-Hernandez et al., (2000) "Part 1. Photochemical and Photophysical Studies of Guanine Derivatives: Intermediates Contributing to its Photodestruction Mechanism in Aqueous Solution and the Participation of the Electron Adduct," Photochemistry and Photobiology, 71(5):534-543.

Eid et al. (2008) "Real-time DNA sequencing from single polymerase molecule" Science 323:133-138.

Fuller et al. (2009) "The challenges of sequencing by synthesis" Nat Biotechnol 27:1013-1023.

Guo et al. (2008) "Four-Color DNA Sequencing With 3'-O-modified Nucletide Reversible Terminators and Chemically Cleavable Fluorescent Dideoxynucleotides", PNAS, 105:9145-9150.

Guo et al., (2010) "An Integrated System for DNA Sequencing by Synthesis Using Novel Nucleotide Analogues", Accounts of Chem. Res., 43:551-563.

Harris et al. (2008) "Single-molecule DNA sequencing of a viral genome" Science, 320:106-109.

Hawkins et al. (2010) "Next-generation genomics: an integrative approach" Nat. Rev. Genet. 11:476-486.

Hayawaka et al. (1993) "O-Allyl Protection of Guanine and Thymine Residues in Oligodeoxyribonucleotides," J. Org. Chem., 58:5551-5555.

Henner, W.D. et al. (1983) "Enzyme Action at 3' Termini of Ionizing Radiation-Induced DNA Strand Breaks," J. Biol. Chem. 258 (24):15198-15205.

Ju, J., Ruan C., Fuller, C.W., Glazer, A.N., and Mathies R.A. (1995) "Fluorescence energy transfer dye-labeled primers for DNA sequencing and analysis," Proc. Natl. Acad. Sci. USA 92: 4347-4351.

Ju, J. et al. (1996) "Cassette Labeling for Facile Construction of Energy Transfer Fluorescent Primers," Nuc. Acids Res. 24(6):1144-1148.

Ju, J., Glazer, A.N., and Mathies, R.A. (1996) "Energy Transfer Primers: A new Fluorescence Labeling Paradigm for DNA Sequencing and Analysis," Nature Medicine 2:246-249.

Ju, J. et al. (2006) "Four-color DNA Sequencing by Synthesis Using Cleavable Fluorescent Nucleotide Reversible Terminators," Proc. Natl. Acad. Sci. USA, 103(52):19635-40. Epub Dec. 14, 2006.

Kitamura et al. (2002) "(P (C6H5) 3) CpRu+Catalyzed Deprotection of Allyl Carboxylic Esters," J. Org. Chem., 67:4975-4977.

Kleinman, S.L. et al, Single-molecule Surface-Enhanced Raman Spectroscopy of Crystal Violet Isotopologues: Theory and Experiment, J. Am Chem Soc, 133, 4115-22 (2011).

Kloosterman et al. (1985) "The relative stability of allyl ether, allyloxycarbonyl ester and prop-2 enylidene acetal, protective groups toward Iridium, Rhodium and Palladium catalysts," Tetrahedron Letters, 26:5045-5048.

(56) References Cited

OTHER PUBLICATIONS

Kurata et al. (2001) "Fluorescent quenching-based quantitative detection of specific DNA/RNA using BODIPY® FL-labeled probe of primer," Nucleic Acids Research, vol. 29, No. 6, p. e34.

Lee, L.G., et al. (1992) "DNA sequencing with dye labeled terminators and T7 DNA polymerase effect of dyes and dNTPs on incorporation of dye terminators and probability analysis of termination fragments," Nucleic Acids Res. 20:2471-2483.

Lee L.G. et al, (1997) "New energy transfer dyes for DNA sequencing," Nucleic Acids Res. 25:2816-2822.

Meng et al. (2006) "Design and Synthesis of a Photocleavable Fluorescent Nucleotide 3'-O-Allyl-dGTP-PC-Biodipy-FL-510 as a Reversible Terminator for DNA Sequencing by Synthesis," J. Org. Chem 71:3248-3252.

Metzker, M.L. et al. (1994) "Termination of DNA synthesis by novel 3' modified deoxyribonucleoside 5' triphosphates," Nucleic Acids Res. 22: 4259-4267.

Metzker M.L. (2005) "Emerging Technologies in DNA Sequencing." Genome Res., 15:1767-1776.

Morozova, O. et al. (2009) "Applications of new sequencing technologies for transcriptome analysis" Annu Rev Genomics Hum Genet 10:135-51.

Nie, S. et al., "Probing Single Molecules and Single Nanoparticles by Surface-Enhanced Raman Scattering," Sciencee 275, 1102-6 (1997).

Park, P.J. (2009) "ChIP-seq: advantages and challenges of a maturing technology" Nat Rev Genet 10:669-680.

Pourmand N. et al. (2002) "Multiplex Pyrosequencing" Nucleic Acids Research 30(7):1-5.

Rao et al. (2001) "Four Color FRET Dye Nucleotide Terminators for DNA Sequencing," Nucleosides, Nucleotides and Nucleic Acids, 20:673-676.

Rasolonjatovo et al. (1998) "6-N-(N-Methylanthranylamido)-4-Oxo-Hexanoic Acid: A New Fluorescent Protecting Group Applicable to a New DNA Sequencing Method," Nucleosides and Nucleotides, 17:2021-2025.

Ronaghi, M. (2001) "Pyrosequencing sheds light on DNA sequencing" Genome Res., 11:3-11.

Ruparel et al. (2005) "Design and Synthesis of a 3'-O-Allyl Photocleavable Fluorescent Nucleotide as a Reversible Terminator for DNA Sequencing by Synthesis," PNAS 102(17):5932-5937.

Sarfati et al., (1995) "Synthesis of fluorescent derivatives of 3'-O-(6-aminohexanoyl)-pyrimidine nucleosides 5'-triphosphates that act as DNA polymerase substrates reversibly tagged at C-3'," JCS Perkin Trans, 1163-1171.

Seeger (1998) "Single Molecule Fluorescence: High-Performance Molecular Diagnosis and Screening," Bioforum, Git Verlag, Darmstadt, DE vol. 21, (German text).

Seo et al. (2004) "Photocleavable Fluorescent Nucleotides for DNA Sequencing on a Chip Constructed by Site-Specific Coupling Chemistry," PNAS 101(15):5488-5493.

Seo et al. (2005) "Four-Color DNA Sequencing by Synthesis on a Chip Using Photocleavable Fluorescent Nucleotides," PNAS 102(17):5926-5931.

Smith, L.M., Sanders, J.Z., Kaiser, R.J., et al. (1986) "Fluorescence Detection in Automated DNA Sequence Analysis," Nature 321:674-679.

Torimura et al. (2001) "Fluorescence-Quenching Phenomenon by Photoinduced Electron Transfer between a Fluorescent Dye and Nucleotide Base," Analytical Sciences, 17:155-160.

Turcatti et al. (2008) "A new class of cleavable fluorescent nucleotides: synthesis and optimization as reversible terminators for DNA sequencing by synthesis" Nucleic Acids Res., 36:e25.

Wada et al. (2001) "2-(Azidomethyl)benzoyl as a new protecting group in nucleosides," Tetrahedron Letters, 42:1069-1072.

Weiss (1999) "Fluorescent Spectroscopy of Single Biomolecules." Science, 283:1676.

Welch MB, Burgess K, (1999) "Synthesis of fluorescent, photolabile 3'-O-protected nucleoside triphosphates for the base addition sequencing scheme," Nucleosides and Nucleotides 18:197-201.

Wu et al. (2007) 3'-O-modified Nucleotides as Reversible Terminators for Pyrosequencing. Proc Natl Acad Sci USA 104:16462-16467.

Wu et al. (2007) "Termination of DNA synthesis by N6-alkylated, not 3'-O-alkylated, photocleavable 2'-deoxyadenosine triphosphates" Nucleic Acids Res. 35:6339-49.

Zavgorodny et al. (2000) "S,X-Acetals in Nucleoside Chemistry. III. Synthesis of 2'- and 3'-O-Azidomethyl Derivatives of Ribonucleosides" Nucleosides, Nucleotides and Nucleic Acids, 19(10-12):1977-1991.

Four-color SBS on Chip Data
- with 3'-O-Adizomethyl-dNTPs-Azido-Dye, Linear Template 3'-O-N₃-dATP 3'-O-N₃-dGTP 3'-O-N₃-dCTP 3'-O-N₃-dTTP 3'-O-N₃-dATP 3'-O-N₃-dCTP 3'-O-N₃-dGTP 3'-O-N₃-dTTP

SEQUENCE LISTING

```
<160> NUMBER OF SEQ ID NOS: 5

<210> SEQ ID NO 1
<211> LENGTH: 51
<212> TYPE: DNA
<213> ORGANISM: Artificial Sequence
<220> FEATURE:
<223> OTHER INFORMATION: Synthetic Template

<400> SEQUENCE: 1
gaggccaagt acggcgggta cgtccttgac aatgtgtaca tcaacatcac c          51

<210> SEQ ID NO 2
<211> LENGTH: 13
<212> TYPE: DNA
<213> ORGANISM: Artificial Sequence
<220> FEATURE:
<223> OTHER INFORMATION: Synthetic Primer

<400> SEQUENCE: 2
cacattgtca agg                                                    13

<210> SEQ ID NO 3
<211> LENGTH: 21
<212> TYPE: DNA
<213> ORGANISM: Artificial Sequence
<220> FEATURE:
<223> OTHER INFORMATION: Synthetic Template

<400> SEQUENCE: 3
ggttaatttg gttgttgcat g                                           21

<210> SEQ ID NO 4
<211> LENGTH: 10
<212> TYPE: DNA
<213> ORGANISM: Artificial Sequence
<220> FEATURE:
<223> OTHER INFORMATION: Synthetic Template
<220> FEATURE:
<221> NAME/KEY: misc_feature
<222> LOCATION: (5)..(10)
<223> OTHER INFORMATION: n is a, c, g, or t

<400> SEQUENCE: 4 gtcannnnnn                                                        10

<210> SEQ ID NO 5
<211> LENGTH: 11
<212> TYPE: DNA
<213> ORGANISM: Artificial Sequence
<220> FEATURE:
<223> OTHER INFORMATION: Synthetic Template
<220> FEATURE:
```

```
<221> NAME/KEY: misc_feature
<222> LOCATION: (8)..(11)
<223> OTHER INFORMATION: n is a, c, g, or t

<400> SEQUENCE: 5
actggggnnn n                                                              11
```

DNA SEQUENCING BY SYNTHESIS USING RAMAN AND INFRARED SPECTROSCOPY DETECTION

This application is a divisional of U.S. application Ser. No. 14/119,846, filed Dec. 5, 2014, now U.S. Pat. No. 9,624,539, issued Apr. 18, 2017, which is a § 371 National Stage Entry of PCT International Application No. PCT/US2012/039198, filed May 23, 2012, claiming the benefit of U.S. Provisional Application No. 61/489,191, filed May 23, 2011, each of which is incorporated herein by reference in its entirety.

This invention was made with government support under grants HG005109 and HG003582 awarded by the NIH. The government has certain rights in the invention.

Throughout this application, certain publications are referenced in parentheses. Full citations for these publications may be found immediately preceding the claims. The disclosures of these publications in their entireties are hereby incorporated by reference into this application in order to describe more fully the state of the art to which this invention relates.

REFERENCE TO SEQUENCE LISTING

This application incorporates-by-reference nucleotide and/or amino acid sequences which are present in the file named "170418_82278-AZ-PCT-US_RBR", which is 2 kilobytes in size, and which was created Apr. 18, 2017 in the IBM-PC machine format, having an operating system compatibility with MS-Windows, which is contained in the ASCII format file that was filed Apr. 18, 2017 as part of this application.

BACKGROUND OF THE INVENTION

Sequencing by Synthesis (SBS) has driven much of the "next generation" sequencing technology, allowing the field to approach the $100,000 Genome (1-4). With further improvements in nucleotide incorporation detection methods, SBS could be an engine that drives third-generation platforms leading to the reality of the "$1,000 Genome". At the same time, since non-fluorescent detection approaches are likely to decrease the cost of obtaining data by avoiding expensive cameras and imaging tools, SBS also offers the possibility of high sensitivity, leading to both longer reads and permitting single molecule sequencing, thereby removing one of the most time-consuming and biased steps, the generation and amplification of DNA templates.

Some commercial platforms have been able to achieve direct single molecule sequencing but at the expense of accuracy (e.g., a single fluorescent tag in the case of the Helicoscope tSMS™ technology, 4 different fluorophores in Pacific Biosciences' SMRT sequencing approach, or illumination of 4 different fluors by enzyme-attached quantum dots in Life Technologies SMS system) (5-7). The shortcoming in all these approaches is that their dependence upon precise timing of a "virtual" pause between each nucleotide incorporation event, especially when registering the incorporation of more than a single base. This becomes particularly pronounced with homopolymeric runs of more than about 4 bases, which are often resolved by summing the fluorescent signals, rather than attempting to measure their timing (8, 9). The use of reversible terminators overcomes this obstacle by only allowing a single base to be incorporated prior to the detection step; only after subsequent cleavage of the terminating moiety on the nucleotide, can the next one be incorporated and identified (10-13). In the case of an already established system with fluorescently tagged nucleotide reversible terminators (NRTs), because each of the nucleotides has a separate fluorescent tag, all four can be added at the same time, reducing the number of rounds of incorporation 4-fold (14, 15). It is noteworthy that this strategy has also been shown to solve the accuracy problem for pyrosequencing, used by a Roche sequencing platform, which is not a single-molecule approach (16).

SUMMARY OF THE INVENTION

A nucleoside triphosphate analogue having the structure:

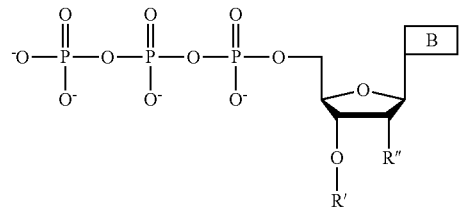

wherein B is a base and is adenine, guanine, cytosine, uracil or thymine, wherein R" is OH or H, and wherein R' is azidomethyl, a hydrocarbyl, or a substituted hydrocarbyl, which (i) preferably has one of the following structures:

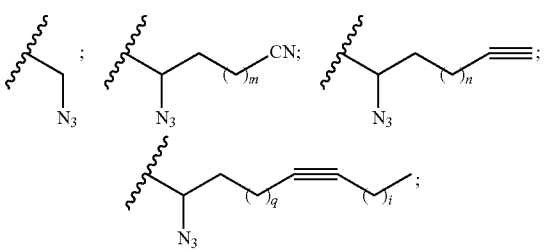

wherein m is $C_1$-$C_5$, preferably $C_1$;
n is $C_1$-$C_5$, preferably $C_1$; and
q is $C_1$-$C_5$, preferably $C_1$; and i is $C_0$-$C_4$, preferably $C_0$.
and (ii) has a Raman spectroscopy peak with wavenumber from 2000 $cm^{-1}$ to 2300 $cm^{-1}$ or a Fourier transform-infrared spectroscopy peak with wavenumber from 2000 $cm^{-1}$ to 2300 $cm^{-1}$.

In one embodiment, the nucleoside triphosphate analogue R" is H and the nucleoside triphosphate analogue is a deoxyribonucleoside triphosphate analogue. In another embodiment, the nucleoside triphosphate analogue R" is OH and the nucleoside triphosphate analogue is a ribonucleoside triphosphate analogue.

This invention also provides a polynucleotide analogue, wherein the polynucleotide analogue differs from a polynucleotide by comprising at its 3' terminus one of the following structures in place of the H atom of the 3' OH group of the polynucleotide:

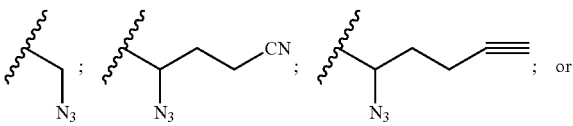

; or

-continued

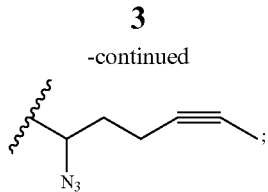

wherein the wavy line indicates the point of attachment to the 3' oxygen atom.

Further, this invention provides a composition comprising four deoxyribonucleoside triphosphate (dNTP) analogues, each dNTP analogue having the structure:

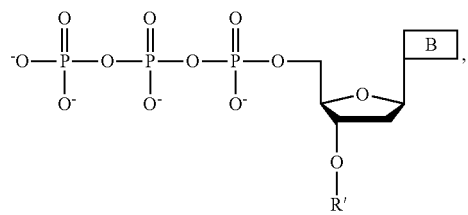

wherein B is a base and is adenine, guanine, cytosine, uracil or thymine, and wherein R' has the structure:

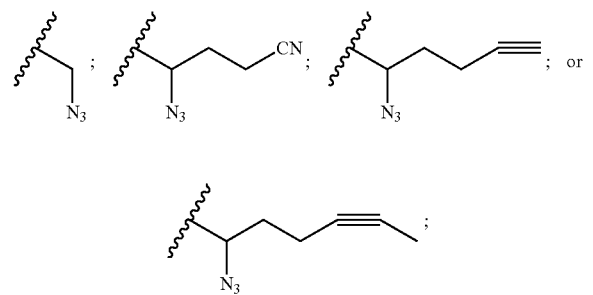

wherein the wavy line indicates the point of attachment to the 3' oxygen atom, and wherein (i) the structure of the R' group of each of the four dNTP analogues is different from the structure of the R' group of the remaining three dNTP analogues, and (ii) each of the four dNTP analogues comprises a base which is different from the base of the remaining three dNTP analogues.

Still further this invention provides a method for determining the sequence of consecutive nucleotide residues of a single-stranded DNA comprising:

(a) contacting the single-stranded DNA, having a primer hybridized to a portion thereof, with a DNA polymerase and four deoxyribonucleoside triphosphate (dNTP) analogues under conditions permitting the DNA polymerase to catalyze incorporation into the primer of a dNTP analogue complementary to a nucleotide residue of the single-stranded DNA which is immediately 5' to a nucleotide residue of the single-stranded DNA hybridized to the 3' terminal nucleotide residue of the primer, so as to form a DNA extension product, wherein (i) each of the four dNTP analogues has the structure:

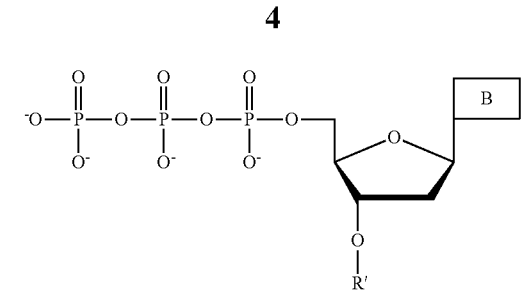

wherein B is a base and is adenine, guanine, cytosine, or thymine, (ii) each of the four dNTP analogues has an R' group which (a) is azidomethyl, or a substituted or unsubstituted hydrocarbyl group and (b) has a predetermined Raman spectroscopy peak with wavenumber of from 2000 $cm^{-1}$ to 2300 $cm^{-1}$ and which is different from the wavenumber of the Raman spectroscopy peak of the other three dNTP analogues, and (iii) each of the four dNTP analogues comprises a base which is different from the base of the other three dNTP analogues;

(b) removing dNTP analogues not incorporated into the DNA extension product;

(c) determining after step (b) the wavenumber of the Raman spectroscopy peak of the dNTP analogue incorporated in step (a) so as to thereby determine the identity of the incorporated dNTP analogue and thus determine the identity of the complementary nucleotide residue in the single-stranded DNA;

(d) treating the incorporated nucleotide analogue under specific conditions so as to replace the R' group thereof with an H atom thereby providing a 3' OH group at the 3' terminal of the DNA extension product; and (e) iteratively performing steps (a) to (d) for each nucleotide residue of the single-stranded DNA to be sequenced except that in each repeat of step (a) the dNTP analogue is (i) incorporated into the DNA extension product resulting from a preceding iteration of step (a), and (ii) complementary to a nucleotide residue of the single-stranded DNA which is immediately 5' to a nucleotide residue of the single-stranded DNA hybridized to the 3' terminal nucleotide residue of the DNA extension product resulting from a preceding iteration of step (a), so as to form a subsequent DNA extension product, with the proviso that for the last nucleotide residue to be sequenced step (d) is optional, thereby determining the identity of each of the consecutive nucleotide residues of the single-stranded DNA so as to thereby sequence the DNA.

In addition, this invention provides a method for determining the sequence of consecutive nucleotide residues of a single-stranded DNA comprising:

(a) contacting the single-stranded DNA, having a primer hybridized to a portion thereof, with a DNA polymerase and four deoxyribonucleoside triphosphate (dNTP) analogues under conditions permitting the DNA polymerase to catalyze incorporation into the primer of a dNTP analogue complementary to a nucleotide residue of the single-stranded DNA which is immediately 5' to a nucleotide residue of the single-stranded DNA hybridized to the 3' terminal nucleotide residue of the primer, so as to form a DNA extension product, wherein (i) each of the four dNTP analogues has the structure:

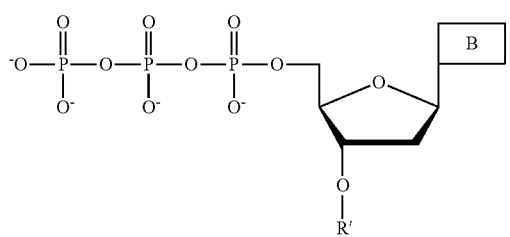

wherein B is a base and is adenine, guanine, cytosine, or thymine, (ii) each of the four dNTP analogues has an R' group which (a) is azidomethyl, or a substituted or unsubstituted hydrocarbyl group, and (b) has a predetermined Fourier transform-infrared spectroscopy peak with wavenumber of from 2000 cm$^{-1}$ to 2300 cm$^{-1}$ and which is different from the wavenumber of the Fourier transform-infrared spectroscopy peak of the other three dNTP analogues, and (iii) each of the four dNTP analogues comprises a base which is different from the base of the other three dNTP analogues;

(b) removing dNTP analogues not incorporated into the DNA extension product;

(c) determining after step (b) the wavenumber of the Fourier transform-infrared spectroscopy peak of the dNTP analogue incorporated in step (a) so as to thereby determine the identity of the incorporated dNTP analogue and thus determine the identity of the complementary nucleotide residue in the single-stranded DNA;

(d) treating the incorporated nucleotide analogue under specific conditions so as to replace the R' group thereof with an H atom thereby providing a 3' OH group at the 3' terminal of the DNA extension product; and (e) iteratively performing steps (a) to (d) for each nucleotide residue of the single-stranded DNA to be sequenced except that in each repeat of step (a) the dNTP analogue is (i) incorporated into the DNA extension product resulting from a preceding iteration of step (a), and (ii) complementary to a nucleotide residue of the single-stranded DNA which is immediately 5' to a nucleotide residue of the single-stranded DNA hybridized to the 3' terminal nucleotide residue of the DNA extension product resulting from a preceding iteration of step (a), so as to form a subsequent DNA extension product, with the proviso that for the last nucleotide residue to be sequenced step (d) is optional, thereby determining the identity of each of the consecutive nucleotide residues of the single-stranded DNA so as to thereby sequence the DNA.

Further, this invention provides a composition comprising four ribonucleoside triphosphate (rNTP) analogues, each rNTP analogue having the structure:

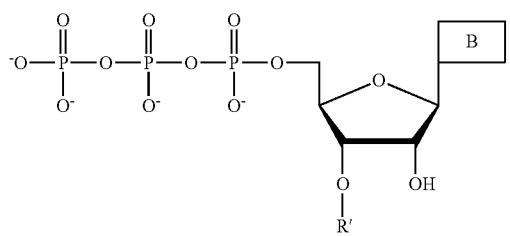

wherein B is a base and is adenine, guanine, cytosine, or uracil, and wherein R' has the structure:

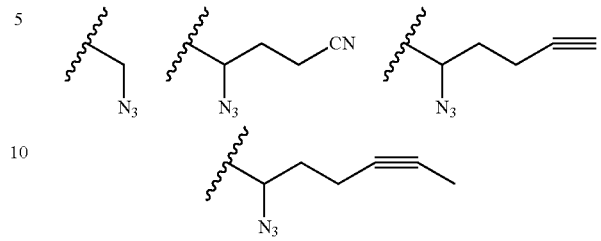

wherein the wavy line indicates the point of attachment to the 3' oxygen atom, and wherein (i) the structure of the R' group of each of the four rNTP analogues is different from the structure of the R' group of the remaining three rNTP analogues, and (ii) each of the four rNTP analogues comprises a base which is different from the base of the remaining three rNTP analogues.

This invention also provides a nucleoside triphosphate analogue having the structure:

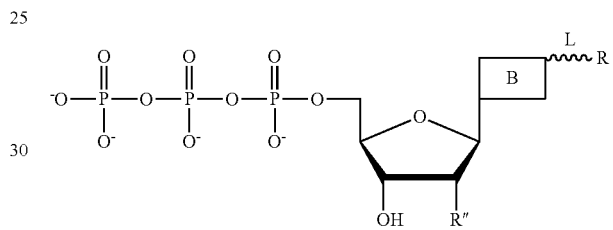

wherein the base is adenine, guanine, cytosine, uracil or thymine,
wherein R" is an OH or an H,
wherein L a cleavable linker, and
wherein R has the structure:

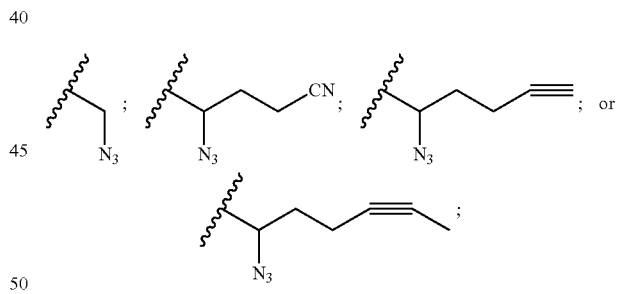

wherein the wavy line indicates the point of attachment to L.

This invention further provides a process for labeling a polynucleotide comprising: contacting the polynucleotide with a deoxyribonucleoside triphosphate analogue having the structure:

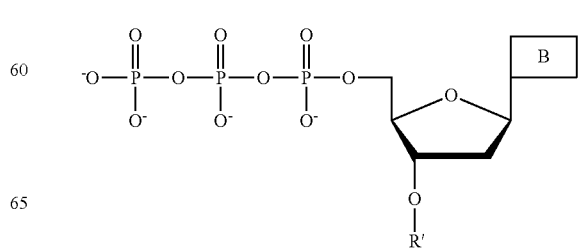

wherein B is a base and is adenine, guanine, cytosine, uracil or thymine, and wherein R' has the structure:

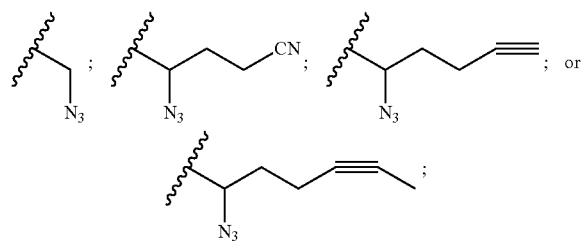

wherein the wavy line indicates the point of attachment to the 3' oxygen atom,
in the presence of a DNA polymerase under conditions permitting incorporation of the deoxyribonucleoside triphosphate analogue into the polynucleotide by formation of a phosphodiester bond between the deoxyribonucleoside triphosphate analogue and a 3' terminal of the polynucleotide so as to thereby label the polynucleotide.

This invention yet further provides a process for labeling a polynucleotide comprising: contacting the polynucleotide with a ribonucleotide triphosphate analogue having the structure:

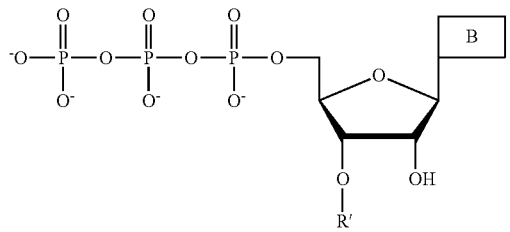

wherein B is a base and is adenine, guanine, cytosine, or uracil, and wherein R' has the structure:

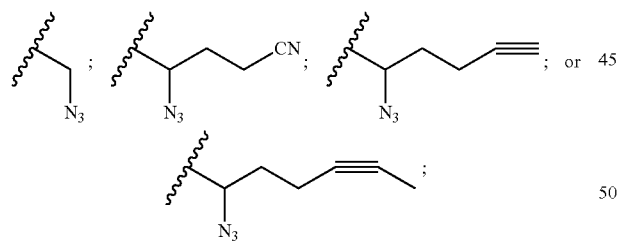

wherein the wavy line indicates the point of attachment to the 3' oxygen atom,
in the presence of an RNA polymerase under conditions permitting incorporation of the ribonucleoside triphosphate analogue into the polynucleotide by formation of a phosphodiester bond between the ribonucleoside triphosphate analogue and a 3' terminal of the polynucleotide so as to thereby label the polynucleotide.

In certain embodiments, this invention provides a method for determining the identity of a nucleotide residue within a stretch of consecutive nucleic acid residues in a single-stranded DNA comprising:
(a) contacting the single-stranded DNA, having a primer hybridized to a portion thereof such that the 3' terminal nucleotide residue of the primer is hybridized to a nucleotide residue of the single-stranded DNA immediately 3' to the nucleotide residue being identified, with a DNA polymerase and a least four deoxyribonucleoside triphosphate (dNTP) analogues under conditions permitting the DNA polymerase to catalyze incorporation into the primer of a dNTP analogue complementary to the nucleotide residue of the single-stranded DNA being identified, so as to form a DNA extension product, wherein (i) each of the four dNTP analogues has the structure:

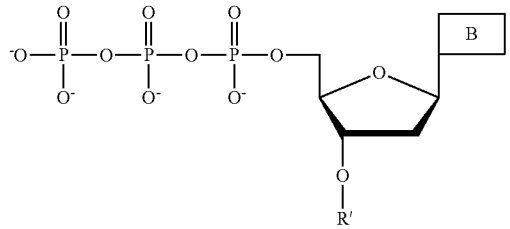

wherein B is a base and is adenine, guanine, cytosine, or thymine, (ii) each of the four dNTP analogues has an R' group which (a) is azidomethyl, or a substituted or unsubstituted hydrocarbyl group, and (b) has a predetermined Raman spectroscopy peak with wavenumber which is from 2000 $cm^{-1}$ to 2300 $cm^{-1}$, and is different from the wavenumber of the Raman spectroscopy peak of the other three dNTP analogues or has a predetermined Fourier transform-infrared spectroscopy peak with wavenumber of from 2000 $cm^{-1}$ to 2300 $cm^{-1}$ and which is different from the wavenumber of the Fourier transform-infrared spectroscopy peak of the other three dNTP analogues, and (iii) each of the four dNTP analogues comprises a base which is different from the base of the other three dNTP analogues;
(b) removing dNTP analogues not incorporated into the DNA extension product; and
(c) determining the wavenumber of the Raman spectroscopy peak or wavenumber of the Fourier transform-infrared spectroscopy peak of the dNTP analogue incorporated in step (a) so as to thereby determine the identity of the incorporated dNTP analogue and thus determine the identity of the complementary nucleotide residue in the single-stranded DNA,
thereby identifying the nucleotide residue within the stretch of consecutive nucleic acid residues in the single-stranded DNA.

In yet further embodiments this invention provides a method for determining the identity of a nucleotide residue within a stretch of consecutive nucleic acid residues in a single-stranded DNA comprising:
(a) contacting the single-stranded DNA, having a primer hybridized to a portion thereof such that the 3' terminal nucleotide residue of the primer is hybridized to a nucleotide residue of the single-stranded DNA immediately 3' to the nucleotide residue identified, with a DNA polymerase and a deoxyribonucleoside triphosphate (dNTP) analogue under conditions permitting the DNA polymerase to catalyze incorporation into the primer of the dNTP analogue if it is complementary to the nucleotide residue of the single-stranded DNA being identified, so as to form a DNA extension product, wherein (i) the dNTP analogue has the structure:

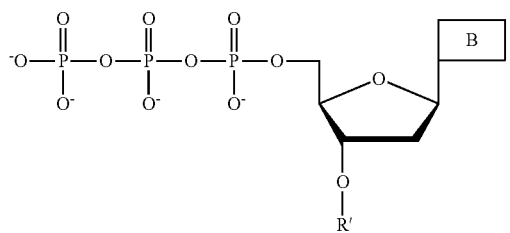

wherein B is a base and is adenine, guanine, cytosine, or thymine, and (ii) the dNTP analogue has an R' group which is azidomethyl, or a substituted or unsubstituted hydrocarbyl group and has a predetermined Raman spectroscopy peak with wavenumber which is from 2000 cm$^{-1}$ to 2300 cm$^{-1}$ or a predetermined Fourier transform-infrared spectroscopy peak with wavenumber which is from 2000 cm$^{-1}$ to 2300 cm$^{-1}$;

(b) removing dNTP analogues not incorporated into the DNA extension product; and (c) determining if the dNTP analogue was incorporated into the primer in step (a) by measuring after step (b) the wavenumber of the Raman spectroscopy peak or wavenumber of the Fourier transform-infrared spectroscopy peak of any dNTP analogue incorporated in step (a), wherein (1) if the dNTP analogue was incorporated in step (a) determining from the wavenumber of the Raman spectroscopy peak or wavenumber of the Fourier transform-infrared spectroscopy peak measured the identity of the incorporated dNTP analogue and thus determining the identity of the complementary nucleotide residue in the single-stranded DNA, and (2) wherein if the dNTP analogue was not incorporated in step (a) iteratively performing steps (a) through (c) until the complementary nucleotide residue in the single-stranded DNA is identified, with the proviso that each dNTP analogue used to contact the single-stranded DNA template in each subsequent iteration of step (a), (i) has a predetermined Raman spectroscopy peak with wavenumber which is different from the wavenumber of the Raman spectroscopy peak of every dNTP analogue used in preceding iterations of step (a) or has a predetermined Fourier transform-infrared spectroscopy peak which is different from the Fourier transform-infrared spectroscopy peak of every dNTP analogue used in preceding iterations of step (a), and (ii) comprises a base which is different from the base of every dNTP analogue used in preceding iterations of step (a), thereby identifying the nucleotide residue within the stretch of consecutive nucleic acid residues in the single-stranded DNA.

In this further embodiment, this invention provides a method for determining the identity of a nucleotide residue within a stretch of consecutive nucleic acid residues in a single-stranded DNA comprising:

(a) contacting the single-stranded DNA with four different oligonucleotide probes, (1) wherein each of the oligonucleotide probes comprises (i) a portion that is complementary to a portion of consecutive nucleotides of the single stranded DNA immediately 3' to the nucleotide residue being identified, and (ii) a 3' terminal nucleotide residue analogue comprising on its sugar a 3'-O—R' group wherein R' is (a) is azidomethyl, or a substituted or unsubstituted hydrocarbyl group and (b) has a predetermined Raman spectroscopy peak with wavenumber which is from 2000 cm$^{-1}$ to 2300 cm$^{-1}$, and which is different from the wavenumber of the Raman spectroscopy peak of the R' of the 3' terminal nucleotide residue analogue of the other three oligonucleotide probes, or has a predetermined Fourier-transform infra red spectroscopy peak with wavenumber which is from 2000 cm$^{-1}$ to 2300 cm$^{-1}$, and is different from the wavenumber of the Fourier-transform infra red peak of the R' of the 3' terminal nucleotide residue analogue of the other three oligonucleotide probes, and (iii) each of the four terminal nucleotide residue analogue comprises a base which is different from the base of the terminal nucleotide residue analogue of the other three oligonucleotide probes, and (2) under conditions permitting hybridization of the primer which is fully complementary to the portion of consecutive nucleotides of the single stranded DNA immediately 3' to the nucleotide residue being identified;

(b) removing oligonucleotide primers not hybridized to the single-stranded DNA; and (c) determining the wavenumber of the Raman spectroscopy peak or wavenumber of the Fourier-transform infra red peak of the dNTP analogue of the oligonucleotide probe hybridized in step (a) so as to thereby determine the identity of the dNTP analogue of the hybridized oligonucleotide probe and thus determine the identity of the complementary nucleotide residue in the single-stranded DNA, thereby identifying the nucleotide residue within the stretch of consecutive nucleic acid residues in the single-stranded DNA.

DETAILED DESCRIPTION OF THE INVENTION

Figure 1:
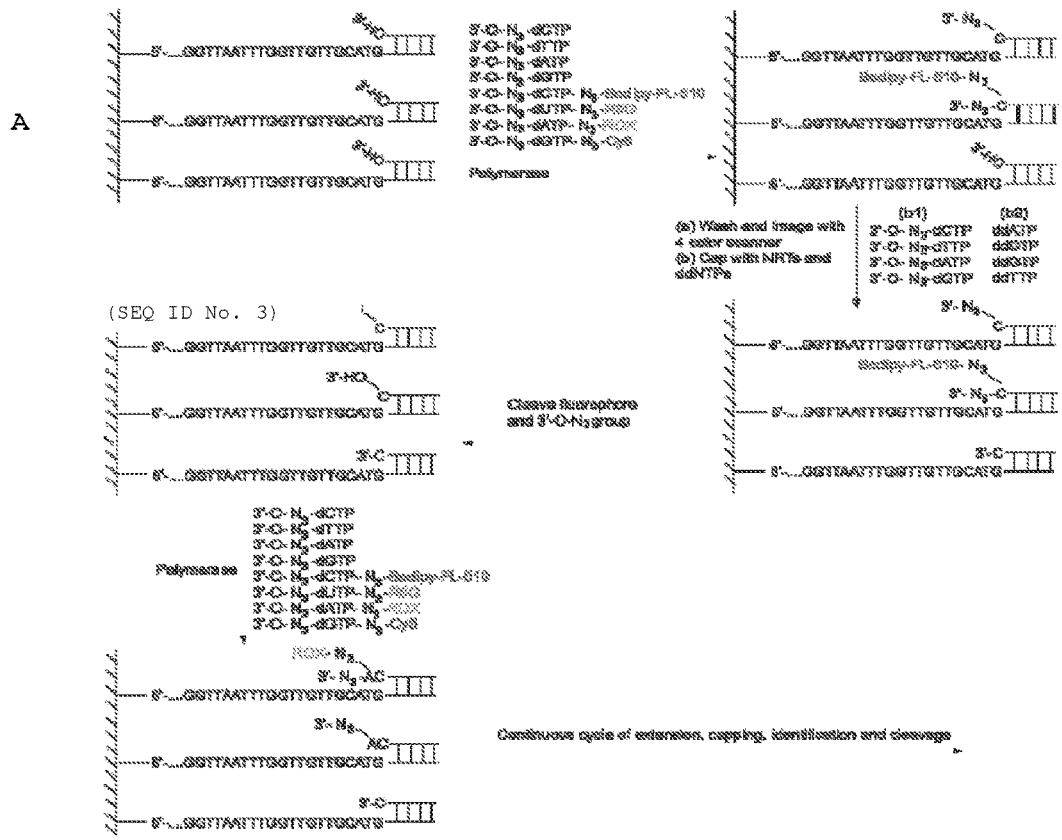
FIG. 1. Sequencing by synthesis (SBS) with nucleotides reversible terminators (NRTs). (A) The scheme for 4-color SBS with 3'-O—N$_3$-dNTP-N$_3$-dye NRTs and unlabeled NRTs. All NRTs, which are substituted with azidomethyl groups at the 3'-OH group and 4 of which have fluorophores attached via linkers also containing azidomethyl groups, are present together in the polymerase reaction. Following incorporation of the correct base and its determination by fluorescent scanning, Tris-(2-carboxyethyl)phosphine (TCEP) is added to cleave the dyes and at the same time restore the 3'-OH group for the next reaction cycle. Unlabeled NRTs, 3'-O—N$_3$-dNTPs (without attached dyes) are included in the reaction and incorporated as well between reactions to ensure that essentially all the primers have been extended (i.e., to synchronize the reactions). (B) A typical result on a surface-bound synthetic template using the 3'-O—N$_3$-dNTP-N$_3$-dye NRTs.
Figure 1:
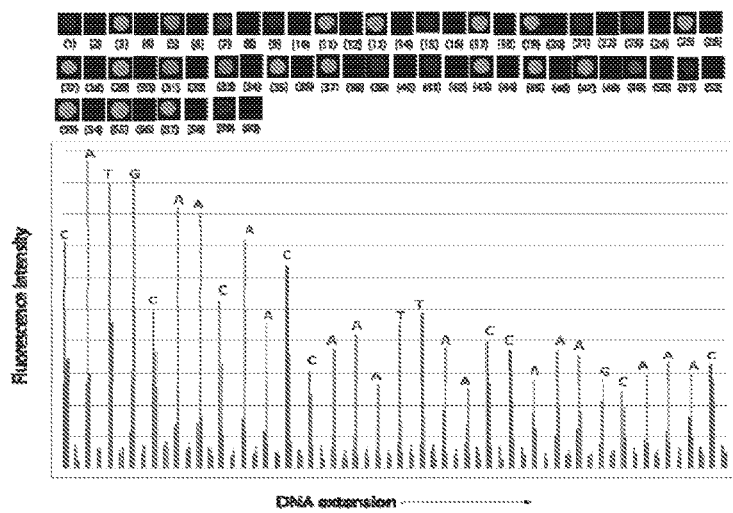

This invention provides nucleoside triphosphate analogue having the structure:

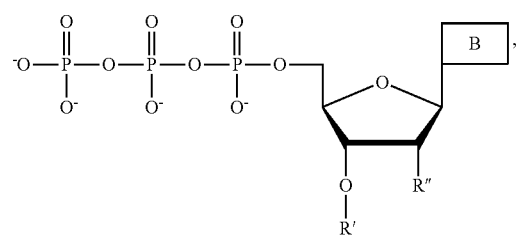

wherein B is a base and is adenine, guanine, cytosine, uracil or thymine, wherein R" is OH or H, and wherein R' is azidomethyl, a hydrocarbyl, or a substituted hydrocarbyl, which (i)

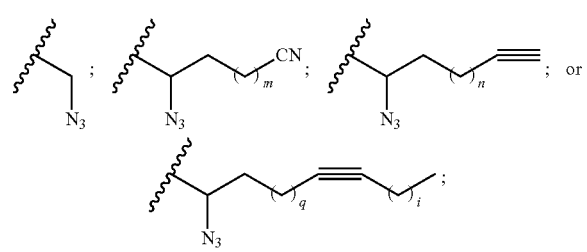

wherein m is $C_1$-$C_5$, preferably $C_1$;

n is $C_1$-$C_5$, preferably $C_1$; and q is $C_1$-$C_5$, preferably $C_1$; and i is $C_0$-$C_4$, preferably $C_0$.

and (ii) has a Raman spectroscopy peak with wavenumber from 2000 $cm^{-1}$ to 2300 $cm^{-1}$ or a Fourier transform-infrared spectroscopy peak with wavenumber of from 2000 $cm^{-1}$ to 2300 $cm^{-1}$.

In one embodiment, the invention provides a nucleoside triphosphate analogue wherein R" is H and the nucleoside triphosphate analogue is a deoxyribonucleoside triphosphate analogue. In another embodiment, the invention provides a nucleoside triphosphate analogue wherein R" is OH and the nucleoside triphosphate analogue is a ribonucleoside triphosphate analogue.

In a further embodiment of the invention the nucleoside triphosphate analogue R' has one of the following structures, wherein the wavy line indicates the point of attachment of R' to the 3' O atom:

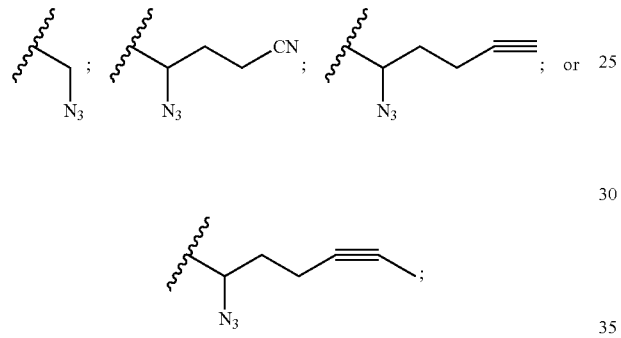

In certain embodiments of the invention the nucleoside triphosphate analogue is recognized by a DNA polymerase or by an RNA polymerase and/or R' has a Raman spectroscopy peak with wavenumber from 2100 $cm^{-1}$ to 2260 $cm^{-1}$.

This invention additionally concerns polynucleotide analogue, wherein the polynucleotide analogue differs from a polynucleotide by comprising at its 3' terminus one of the following structures in place of the H atom of the 3' OH group of the polynucleotide:

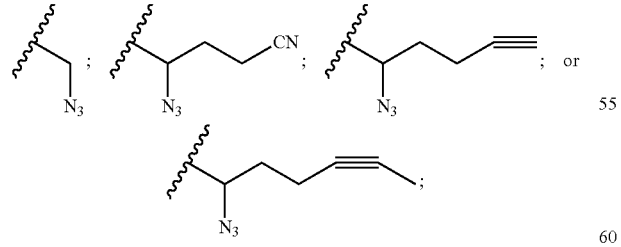

wherein the wavy line indicates the point of attachment to the 3' oxygen atom.

This invention also concerns a composition comprising four deoxyribonucleoside triphosphate (dNTP) analogues, each dNTP analogue having the structure:

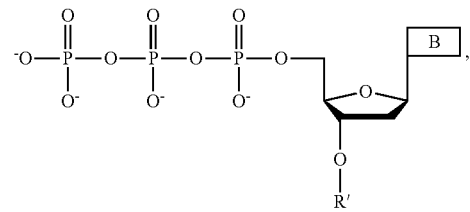

wherein B is a base and is adenine, guanine, cytosine, uracil or thymine, and wherein R' has the structure:

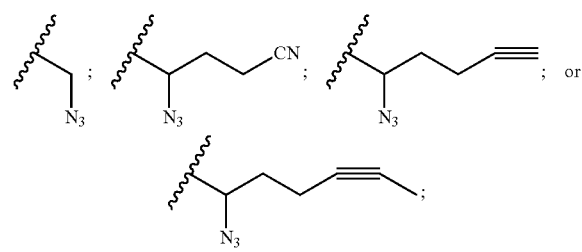

wherein the wavy line indicates the point of attachment to the 3' oxygen atom, and wherein (i) the structure of the R' group of each of the four dNTP analogues is different from the structure of the R' group of the remaining three dNTP analogues, and (ii) each of the four dNTP analogues comprises a base which is different from the base of the remaining three dNTP analogues.

In addition, this invention provides a method for determining the sequence of consecutive nucleotide residues of a single-stranded DNA comprising:

(a) contacting the single-stranded DNA, having a primer hybridized to a portion thereof, with a DNA polymerase and four deoxyribonucleoside triphosphate (dNTP) analogues under conditions permitting the DNA polymerase to catalyze incorporation into the primer of a dNTP analogue complementary to a nucleotide residue of the single-stranded DNA which is immediately 5' to a nucleotide residue of the single-stranded DNA hybridized to the 3' terminal nucleotide residue of the primer, so as to form a DNA extension product, wherein (i) each of the four dNTP analogues has the structure:

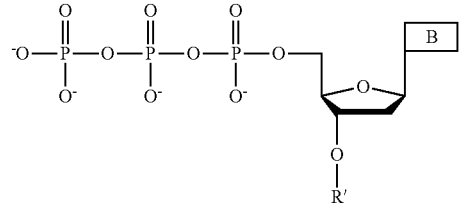

wherein B is a base and is adenine, guanine, cytosine, or thymine, (ii) each of the four dNTP analogues has an R' group which (a) is azidomethyl, or a substituted or unsubstituted hydrocarbyl group and (b) has a predetermined Raman spectroscopy peak with wavenumber of from 2000 $cm^{-1}$ to 2300 $cm^{-1}$ and which is different from the wavenumber of the Raman spectroscopy peak of the other three dNTP analogues, and (iii) each of the four dNTP analogues comprises a base which is different from the base of the other three dNTP analogues;
(b) removing dNTP analogues not incorporated into the DNA extension product;
(c) determining after step (b) the wavenumber of the Raman spectroscopy peak of the dNTP analogue incorporated in step (a) so as to thereby determine the identity of the incorporated dNTP analogue and thus determine the identity of the complementary nucleotide residue in the single-stranded DNA;
(d) treating the incorporated nucleotide analogue under specific conditions so as to replace the R' group thereof with an H atom thereby providing a 3' OH group at the 3' terminal of the DNA extension product; and
(e) iteratively performing steps (a) to (d) for each nucleotide residue of the single-stranded DNA to be sequenced except that in each repeat of step (a) the dNTP analogue is (i) incorporated into the DNA extension product resulting from a preceding iteration of step (a), and (ii) complementary to a nucleotide residue of the single-stranded DNA which is immediately 5' to a nucleotide residue of the single-stranded DNA hybridized to the 3' terminal nucleotide residue of the DNA extension product resulting from a preceding iteration of step (a), so as to form a subsequent DNA extension product, with the proviso that for the last nucleotide residue to be sequenced step (d) is optional,
thereby determining the identity of each of the consecutive nucleotide residues of the single-stranded DNA so as to thereby sequence the DNA.

Further, this invention provides a method for determining the sequence of consecutive nucleotide residues of a single-stranded DNA comprising:
(a) contacting the single-stranded DNA, having a primer hybridized to a portion thereof, with a DNA polymerase and four deoxyribonucleoside triphosphate (dNTP) analogues under conditions permitting the DNA polymerase to catalyze incorporation into the primer of a dNTP analogue complementary to a nucleotide residue of the single-stranded DNA which is immediately 5' to a nucleotide residue of the single-stranded DNA hybridized to the 3' terminal nucleotide residue of the primer, so as to form a DNA extension product, wherein (i) each of the four dNTP analogues has the structure:

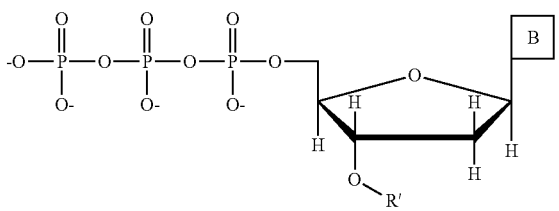

wherein B is a base and is adenine, guanine, cytosine, or thymine, (ii) each of the four dNTP analogues has an R' group which (a) is azidomethyl, or a substituted or unsubstituted hydrocarbyl group and (b) has a predetermined Fourier transform-infrared spectroscopy peak with wavenumber of from 2000 cm$^{-1}$ to 2300 cm$^{-1}$ and which is different from the wavenumber of the Fourier transform-infrared spectroscopy peak of the other three dNTP analogues, and (iii) each of the four dNTP analogues comprises a base which is different from the base of the other three dNTP analogues;

(b) removing dNTP analogues not incorporated into the DNA extension product;
(c) determining after step (b) the peak Fourier transform-infrared spectroscopy wavenumber of the dNTP analogue incorporated in step (a) so as to thereby determine the identity of the incorporated dNTP analogue and thus determine the identity of the complementary nucleotide residue in the single-stranded DNA;
(d) treating the incorporated nucleotide analogue under specific conditions so as to replace the R' group thereof with an H atom thereby providing a 3' OH group at the 3' terminal of the DNA extension product; and
(e) iteratively performing steps (a) to (d) for each nucleotide residue of the single-stranded DNA to be sequenced except that in each repeat of step (a) the dNTP analogue is (i) incorporated into the DNA extension product resulting from a preceding iteration of step (a), and (ii) complementary to a nucleotide residue of the single-stranded DNA which is immediately 5' to a nucleotide residue of the single-stranded DNA hybridized to the 3' terminal nucleotide residue of the DNA extension product resulting from a preceding iteration of step (a), so as to form a subsequent DNA extension product, with the proviso that for the last nucleotide residue to be sequenced step (d) is optional,
thereby determining the identity of each of the consecutive nucleotide residues of the single-stranded DNA so as to thereby sequence the DNA.

In an embodiment of the instant methods the dNTP analogues have a Raman spectroscopy peak with wavenumber of from 2100 cm$^{-1}$ to 2260 cm$^{-1}$. In an embodiment of the instant methods the wavenumber of the Fourier transform-infrared spectroscopy peak is determined by irradiating the incorporated dNTP analogue with grazing angle infra-red light. In an embodiment of the instant methods the peak Raman spectroscopy wavenumber is determined by irradiating the incorporated dNTP analogue with 532 nm, 633 nm, or 785 nm light. In an embodiment of the instant methods at least one of the primer or the single-stranded DNA is attached to a solid surface. In an embodiment of the instant methods the Raman spectroscopy is surface-enhanced Raman spectroscopy (SERS). In an embodiment of the process the polynucleotide is attached to a solid surface. In an embodiment of the process the solid surface is metal or is coated with metal or is impregnated with metal. In an embodiment of the process the solid surface is porous alumina impregnated with silver or gold. In an embodiment of the process the porous alumina solid surface is in the form of a nanotube. In an embodiment of the instant methods in the dNTP analogues R' has a structure chosen from the following:

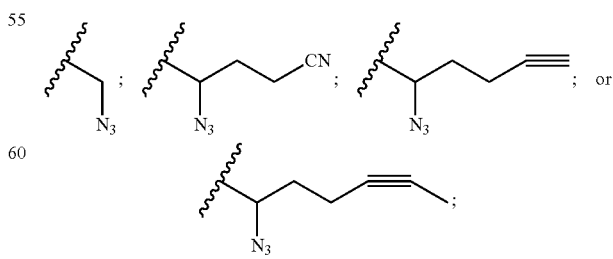

wherein the wavy line indicates the point of attachment to the 3' oxygen atom.

In certain embodiments of the methods of this invention the dNTP analogues each have the structure:

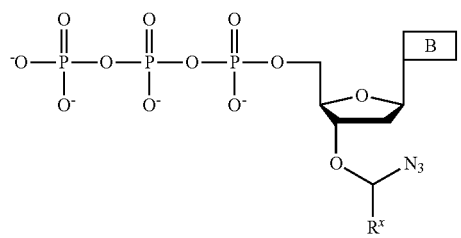

where $R^x$ is, independently, a C1-C5 cyanoalkyl, a C1-C5 alkyl, a C2-C5 alkenyl, or a C2-C5 alkynyl, which is substituted or unsubstituted.

In some embodiment of the methods of this invention, in step (d) the incorporated nucleotide analogue is treated with a specific chemical agent so as to replace the R' group thereof with an H atom thereby providing a 3' OH group at the 3' terminal of the DNA extension product. In other embodiments of the methods, in step (d) the incorporated nucleotide analogue is treated with Tris (2-carboxyethyl) phosphine (TCEP) so as to replace the R' group thereof with an H atom thereby providing a 3' OH group at the 3' terminal of the DNA extension product.

Further this invention concerns a composition comprising four ribonucleoside triphosphate (rNTP) analogues, each rNTP analogue having the structure:

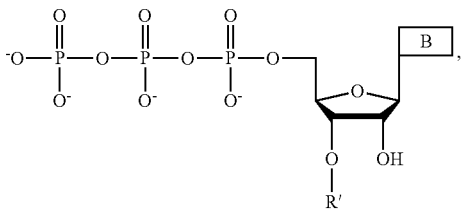

wherein B is a base and is adenine, guanine, cytosine, or uracil, and wherein R' has the structure:

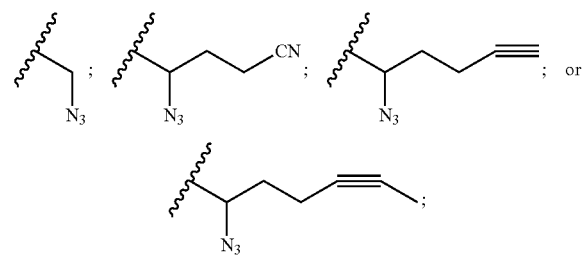

wherein the wavy line indicates the point of attachment to the 3' oxygen atom, and wherein (i) the structure of the R' group of each of the four rNTP analogues is different from the structure of the R' group of the remaining three rNTP analogues, and (ii) each of the four rNTP analogues comprises a base which is different from the base of the remaining three rNTP analogues.

In some embodiments the invention provides a nucleoside triphosphate analogue having the structure:

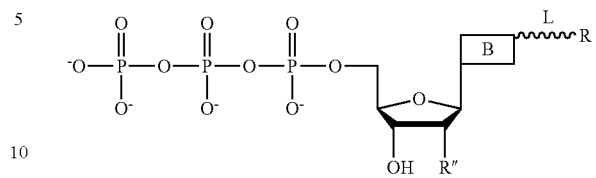

wherein the base is adenine, guanine, cytosine, uracil or thymine,
wherein R" is an OH or an H,
wherein L a cleavable linker, and
wherein R has the structure:

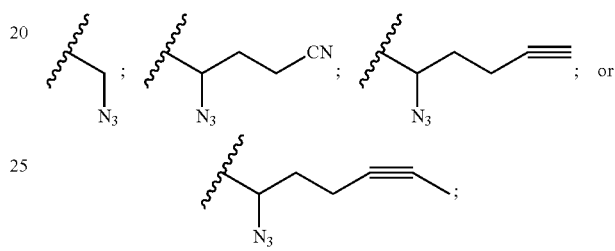

wherein the wavy line indicates the point of attachment to L.

In certain embodiments of the nucleoside triphosphate analogue, L is a single covalent bond. In some embodiments L comprises one or more photocleavable covalent bonds. In other embodiment R" is H and the nucleoside triphosphate analogue is a deoxyribonucleoside triphosphate analogue. Yet still other embodiments R" is OH and the nucleoside triphosphate analogue is a ribonucleoside triphosphate analogue.

This invention also concerns a process for labeling a polynucleotide comprising: contacting the polynucleotide with a deoxyribonucleoside triphosphate analogue having the structure:

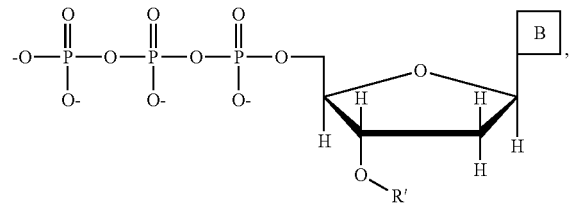

wherein B is a base and is adenine, guanine, cytosine, uracil or thymine, and wherein R' has the structure:

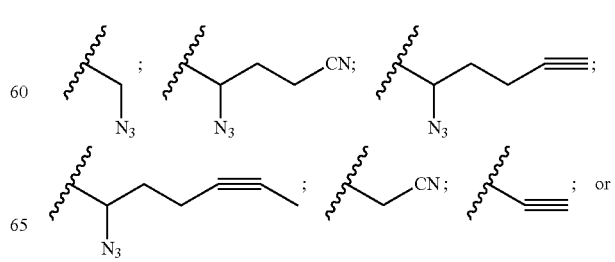

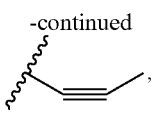

wherein the wavy line indicates the point of attachment to the 3' oxygen atom,
in the presence of a DNA polymerase under conditions permitting incorporation of the deoxyribonucleoside triphosphate analogue into the polynucleotide by formation of a phosphodiester bond between the deoxyribonucleoside triphosphate analogue and a 3' terminal of the polynucleotide so as to thereby label the polynucleotide.

In certain embodiment of this process, the polynucleotide is a deoxyribonucleic acid. In other embodiment of the process, the deoxyribonucleic acid is a primer. In still other embodiments of the process, the DNA polymerase is 9° N polymerase or a variant thereof, E. Coli DNA polymerase I, Bacteriophage T4 DNA polymerase, Sequenase, Taq DNA polymerase or 9° N polymerase (exo-)A485L/Y409V.

This invention yet further provides a process for labeling a polynucleotide comprising: contacting the polynucleotide with a ribonucleoside triphosphate analogue having the structure:

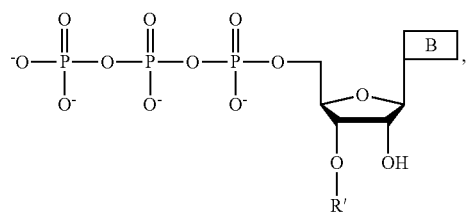

wherein B is a base and is adenine, guanine, cytosine, or uracil, and wherein R' has the structure:

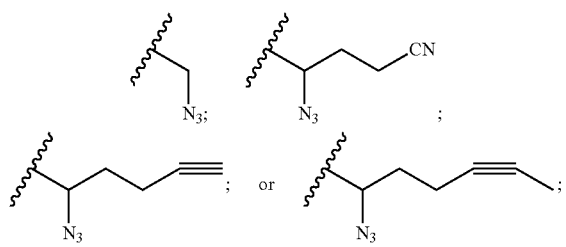

wherein the wavy line indicates the point of attachment to the 3' oxygen atom,
in the presence of an RNA polymerase under conditions permitting incorporation of the ribonucleoside triphosphate analogue into the polynucleotide by formation of a phosphodiester bond between the ribonucleoside triphosphate analogue and a 3' terminal of the polynucleotide so as to thereby label the polynucleotide.

In embodiments of this process, the polynucleotide is a ribonucleic acid. In certain embodiment of the process, the polymerase is Bacteriophage SP6, T7 or T3 RNA polymerases. In other embodiment of the process, the polynucleotide is attached to a solid surface. In certain embodiment of the process, the solid surface is metal or is coated with metal or is impregnated with metal. In more specific embodiments of the process, the solid surface is porous alumina impregnated with silver or gold; or is a porous alumina solid surface in the form of a nanotube.

In certain embodiment of the process, the single-stranded DNA is amplified from a sample of DNA prior to step (a).

In some embodiments of the process the single-stranded DNA is amplified by a polymerase chain reaction.

This invention also concerns a method for determining the identity of a nucleotide residue within a stretch of consecutive nucleic acid residues in a single-stranded DNA comprising:

(a) contacting the single-stranded DNA, having a primer hybridized to a portion thereof such that the 3' terminal nucleotide residue of the primer is hybridized to a nucleotide residue of the single-stranded DNA immediately 3' to the nucleotide residue being identified, with a DNA polymerase and a least four deoxyribonucleoside triphosphate (dNTP) analogues under conditions permitting the DNA polymerase to catalyze incorporation into the primer of a dNTP analogue complementary to the nucleotide residue of the single-stranded DNA being identified, so as to form a DNA extension product, wherein (i) each of the four dNTP analogues has the structure:

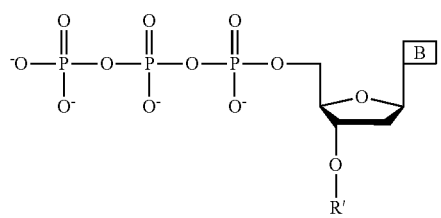

wherein B is a base and is adenine, guanine, cytosine, or thymine, (ii) each of the four dNTP analogues has an R' group which (a) is azidomethyl, or a substituted or unsubstituted hydrocarbyl group and (b) has a predetermined Raman spectroscopy peak with wavenumber which is from 2000 $cm^{-1}$ to 2300 $cm^{-1}$, and is different from the wavenumber of the Raman spectroscopy peak of the other three dNTP analogues or has a predetermined Fourier transform-infrared spectroscopy peak with wavenumber of from 2000 $cm^{-1}$ to 2300 $cm^{-1}$ and which is different from the wavenumber of the Fourier transform-infrared spectroscopy peak of the other three dNTP analogues, and (iii) each of the four dNTP analogues comprises a base which is different from the base of the other three dNTP analogues;

(b) removing dNTP analogues not incorporated into the DNA extension product; and (c) determining the wavenumber of the Raman spectroscopy peak or wavenumber of the Fourier transform-infrared spectroscopy peak of the dNTP analogue incorporated in step (a) so as to thereby determine the identity of the incorporated dNTP analogue and thus determine the identity of the complementary nucleotide residue in the single-stranded DNA, thereby identifying the nucleotide residue within the stretch of consecutive nucleic acid residues in the single-stranded DNA.

Yet further this invention concerns a method for determining the identity of a nucleotide residue within a stretch of consecutive nucleic acid residues in a single-stranded DNA comprising:

(a) contacting the single-stranded DNA, having a primer hybridized to a portion thereof such that the 3' terminal nucleotide residue of the primer is hybridized to a nucleotide residue of the single-stranded DNA immediately 3' to the nucleotide residue to be identified, with a DNA polymerase and a deoxyribonucleoside triphosphate (dNTP) analogue under conditions permitting the DNA polymerase to catalyze incorporation into the primer of the dNTP analogue if it is complementary to the nucleotide residue of the single-stranded DNA being identified, so as to form a DNA extension product, wherein (i) the dNTP analogue has the structure:

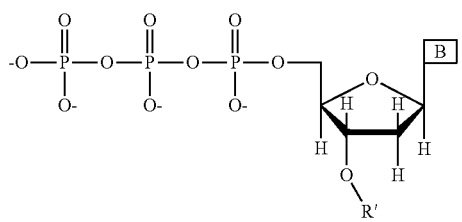

wherein B is a base and is adenine, guanine, cytosine, or thymine, and (ii) the dNTP analogue has an R' group which is azidomethyl, or a substituted or unsubstituted hydrocarbyl group and has a predetermined Raman spectroscopy peak with wavenumber which is from 2000 cm$^{-1}$ to 2300 cm$^{-1}$ or a predetermined Fourier transform-infrared spectroscopy peak with wavenumber which is from 2000 cm$^{-1}$ to 2300 cm$^{-1}$;

(b) removing dNTP analogues not incorporated into the DNA extension product; and (c) determining if the dNTP analogue was incorporated into the primer in step (a) by measuring after step (b) the wavenumber of the Raman spectroscopy peak or wavenumber of the Fourier transform-infrared spectroscopy peak of any dNTP analogue incorporated in step (a), wherein (1) if the dNTP analogue was incorporated in step (a) determining from the wavenumber of the Raman spectroscopy peak or wavenumber of the Fourier transform-infrared spectroscopy peak measured the identity of the incorporated dNTP analogue and thus determining the identity of the complementary nucleotide residue in the single-stranded DNA, and (2) wherein if the dNTP analogue was not incorporated in step (a) iteratively performing steps (a) through (c) until the complementary nucleotide residue in the single-stranded DNA is identified, with the proviso that each dNTP analogue used to contact the single-stranded DNA template in each subsequent iteration of step (a), (i) has a predetermined Raman spectroscopy peak whose wavenumber is different from the wavenumber of the Raman spectroscopy peak of every dNTP analogue used in preceding iterations of step (a) or has a predetermined Fourier transform-infrared spectroscopy peak which is different from the Fourier transform-infrared spectroscopy peak of every dNTP analogue used in preceding iterations of step (a), and (ii) comprises a base which is different from the base of every dNTP analogue used in preceding iterations of step (a), thereby identifying the nucleotide residue within the stretch of consecutive nucleic acid residues in the single-stranded DNA.

Still further, this invention concerns a method for determining the identity of a nucleotide residue within a stretch of consecutive nucleic acid residues in a single-stranded DNA comprising:

(a) contacting the single-stranded DNA with four different oligonucleotide probes, (1) wherein each of the oligonucleotide probes comprises (i) a portion that is complementary to a portion of consecutive nucleotides of the single stranded DNA immediately 3' to the nucleotide residue being identified, and (ii) a 3' terminal nucleotide residue analogue comprising on its sugar a 3'-O—R' group wherein R' is (a) is azidomethyl, or a substituted or unsubstituted hydrocarbyl group and (b) has a predetermined Raman spectroscopy peak with wavenumber which is from 2000 cm$^{-1}$ to 2300 cm$^{-1}$, and which is different from the wavenumber of the Raman spectroscopy peak of the R' of the 3' terminal nucleotide residue analogue of the other three oligonucleotide probes, or has a predetermined Fourier-transform infra red spectroscopy peak with wavenumber which is from 2000 cm$^{-1}$ to 2300 cm$^{-1}$, and is different from the wavenumber of the Fourier-transform infra red peak of the R' of the 3' terminal nucleotide residue analogue of the other three oligonucleotide probes, and (iii) each of the four terminal nucleotide residue analogue comprises a base which is different from the base of the terminal nucleotide residue analogue of the other three oligonucleotide probes, and (2) under conditions permitting hybridization of the primer which is fully complementary to the portion of consecutive nucleotides of the single stranded DNA immediately 3' to the nucleotide residue being identified;

(b) removing oligonucleotide primers not hybridized to the single-stranded DNA; and (c) determining the wavenumber of the Raman spectroscopy peak or wavenumber of the Fourier-transform infra red peak of the dNTP analogue of the oligonucleotide probe hybridized in step (a) so as to thereby determine the identity of the dNTP analogue of the hybridized oligonucleotide probe and thus determine the identity of the complementary nucleotide residue in the single-stranded DNA, thereby identifying the nucleotide residue within the stretch of consecutive nucleic acid residues in the single-stranded DNA.

In some embodiments of the invention, the dNTP analogues or R' groups have a Raman spectroscopy peak with wavenumber of from 2100 cm$^{-1}$ to 2260 cm$^{-1}$. In certain embodiments, the wavenumber of the Raman spectroscopy peak is determined by irradiating the incorporated dNTP analogue with 532 nm, 633 nm, or 785 nm light. In some embodiments, at least one of the primer, probes, or the single-stranded DNA is attached to a solid surface. In select embodiments, the Raman spectroscopy is surface-enhanced Raman spectroscopy. In some such embodiments, the dNTP analogue R' has the structure:

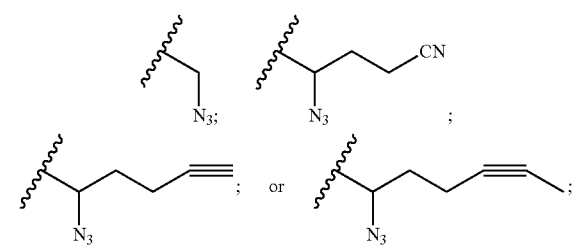

wherein the wavy line indicates the point of attachment to the 3' oxygen atom.

In other embodiments of the invention the dNTP analogues each have the structure:

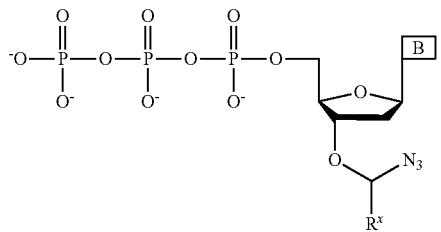

where $R^x$ is a C1-C5 cyanoalkyl, a C1-C5 alkyl, a C2-C5 alkenyl, or a C2-C5 alkynyl, which is substituted or unsubstituted.

As used herein, "alkyl" includes both branched and straight-chain saturated aliphatic hydrocarbon groups having the specified number of carbon atoms and may be unsubstituted or substituted. Thus, C1-Cn as in "C1-Cn alkyl" includes groups having 1, 2, . . . , n–1 or n carbons in a linear or branched arrangement. For example, a "C1-C5 alkyl" includes groups having 1, 2, 3, 4, or 5 carbons in a linear or branched arrangement, and specifically includes methyl, ethyl, n-propyl, isopropyl, n-butyl, t-butyl, and pentyl As used herein, "alkenyl" refers to a non-aromatic hydrocarbon group, straight or branched, containing at least 1 carbon to carbon double bond, and up to the maximum possible number of non-aromatic carbon-carbon double bonds may be present, and may be unsubstituted or substituted. For example, "C2-C5 alkenyl" means an alkenyl group having 2, 3, 4, or 5, carbon atoms, and up to 1, 2, 3, or 4, carbon-carbon double bonds respectively. Alkenyl groups include ethenyl, propenyl, and butenyl.

The term "alkynyl" refers to a hydrocarbon group straight or branched, containing at least 1 carbon to carbon triple bond, and up to the maximum possible number of non-aromatic carbon-carbon triple bonds may be present, and may be unsubstituted or substituted. Thus, "C2-C5 alkynyl" means an alkynyl group having 2 or 3 carbon atoms and 1 carbon-carbon triple bond, or having 4 or 5 carbon atoms and up to 2 carbon-carbon triple bonds. Alkynyl groups include ethynyl, propynyl and butynyl.

The term "substituted" refers to a functional group as described above such as an alkyl, or a hydrocarbyl, in which at least one bond to a hydrogen atom contained therein is replaced by a bond to non-hydrogen or non-carbon atom, provided that normal valencies are maintained and that the substitution(s) result(s) in a stable compound. Substituted groups also include groups in which one or more bonds to a carbon(s) or hydrogen(s) atom are replaced by one or more bonds, including double or triple bonds, to a heteroatom. Non-limiting examples of substituents include the functional groups described above, and for example, N, e.g. so as to form —CN.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

In choosing the compounds of the present invention, one of ordinary skill in the art will recognize that the various substituents, i.e. $R_1$, $R_2$, etc. are to be chosen in conformity with well-known principles of chemical structure connectivity.

It is understood that where chemical groups are represented herein by structure, the point of attachment to the main structure is represented by a wavy line.

In the compound structures depicted herein, hydrogen atoms, except on ribose and deoxyribose sugars, are generally not shown. However, it is understood that sufficient hydrogen atoms exist on the represented carbon atoms to satisfy the octet rule.

As used herein, and unless stated otherwise, each of the following terms shall have the definition set forth below.
A—Adenine;
C—Cytosine;
G—Guanine;
T—Thymine;
U—Uracil;
DNA—Deoxyribonucleic acid;
RNA—Ribonucleic acid;
FTIR—Fourier-transform infrared.

"Nucleic acid" shall mean, unless otherwise specified, any nucleic acid molecule, including, without limitation, DNA, RNA and hybrids thereof. In an embodiment the nucleic acid bases that form nucleic acid molecules can be the bases A, C, G, T and U, as well as derivatives thereof. Derivatives of these bases are well known in the art, and are exemplified in PCR Systems, Reagents and Consumables (Perkin Elmer Catalogue 1996-1997, Roche Molecular Systems, Inc., Branchburg, N.J., USA).

"Solid substrate" shall mean any suitable medium present in the solid phase to which a nucleic acid or an agent may be affixed. Non-limiting examples include chips, beads, nanopore structures and columns. In an embodiment the solid substrate can be present in a solution, including an aqueous solution, a gel, or a fluid.

"Hybridize" shall mean the annealing of one single-stranded nucleic acid to another nucleic acid based on the well-understood principle of sequence complementarity. In an embodiment the other nucleic acid is a single-stranded nucleic acid. The propensity for hybridization between nucleic acids depends on the temperature and ionic strength of their milieu, the length of the nucleic acids and the degree of complementarity. The effect of these parameters on hybridization is well known in the art (see Sambrook J, Fritsch E F, Maniatis T. 1989. Molecular cloning: a laboratory manual. Cold Spring Harbor Laboratory Press, New York.). As used herein, hybridization of a primer sequence, or of a DNA extension product, to another nucleic acid shall mean annealing sufficient such that the primer, or DNA extension product, respectively, is extendable by creation of a phosphodiester bond with an available nucleotide or nucleotide analogue capable of forming a phosphodiester bond.

As used herein, unless otherwise specified, a base which is "different from" another base or a recited list of bases shall mean that the base has a different structure from the other base or bases. For example, a base that is "different from" adenine, thymine, and cytosine would include a base that is guanine or a base that is uracil.

In some embodiments of the invention, vibrational spectroscopy is used to detect the presence of incorporated nucleotide analogues. Vibrational spectroscopy is a spectrographic analysis where the sample is illuminated with incident radiation in order to excite molecular vibrations. Vibrational excitation, caused by molecules of the sample absorbing, reflecting or scattering a particular discrete amount of energy, is detected and can be measured. The two major types of vibrational spectroscopy are infrared (usually FTIR) and Raman. If FTIR is employed, then the IR spectra of the nucleotide analogues are measured (for example of the nucleotide analogues and in the methods described herein) If Raman is employed, then the Raman spectra of the nucleotide analogues is measured (for example of the nucleotide analogues and in the methods described herein).

In certain embodiments, the single-stranded DNA, RNA, primer or probe is bound to the solid substrate via 1,3-dipolar azide-alkyne cycloaddition chemistry. In an embodiment the DNA, RNA, primer or probe is bound to the solid substrate via a polyethylene glycol molecule. In an embodiment the DNA, RNA, primer or probe is alkyne-labeled. In an embodiment the DNA, RNA, primer or probe is bound to the solid substrate via a polyethylene glycol molecule and the solid substrate is azide-functionalized. In an embodiment the DNA, RNA, primer or probe is immobilized on the solid substrate via an azido linkage, an alkynyl linkage, or biotin-streptavidin interaction. Immobilization of nucleic acids is described in Immobilization of DNA on Chips II, edited by Christine Wittmann (2005), Springer Verlag, Berlin, which is hereby incorporated by reference. In an embodiment the DNA is single-stranded DNA. In an embodiment the RNA is single-stranded RNA.

In other embodiments, the solid substrate is in the form of a chip, a bead, a well, a capillary tube, a slide, a wafer, a filter, a fiber, a porous media, a porous nanotube, or a column. This invention also provides the instant method, wherein the solid substrate is a metal, gold, silver, quartz, silica, a plastic, polypropylene, a glass, or diamond. This invention also provides the instant method, wherein the solid substrate is a porous non-metal substance to which is attached or impregnated a metal or combination of metals. The solid surface may be in different forms including the non-limiting examples of a chip, a bead, a tube, a matrix, a nanotube. The solid surface may be made from materials common for DNA microarrays, including the non-limiting examples of glass or nylon. The solid surface, for example beads/micro-beads, may be in turn immobilized to another solid surface such as a chip.

In one embodiment, the solid surface is a SERS-prepared surface designed specifically for detection of a label nucleotide. The surface may include one or more nanoplasmonic antenna, wherein the nanoplasmonic antenna may be a nanoplasmonic bowtie antenna. In one embodiment, the nanoplasmonic bowtie antenna comprises crossed-bowtie structure in which one pair of triangles couples to incident field, while another pair of triangles couples to Raman scattered field in an orthogonal polarization. It is also contemplated that the nanoplasmonic antenna may be an array of antennas. In addition, the nanoplasmonic antenna may include DNA functionalized sites, and may have a gap size range from 50 nm to 8 nm. In another embodiment, a DNA polymerase is immobilized within the gap.

In another embodiment, the surface comprises a DNA origami scaffold or an array of DNA origami scaffolds. It is also contemplated that the DNA origami scaffold further comprising a primer molecules positioned between Au and Ag nanoparticles and nanorods located at specified binding sites.

In a further embodiment, the surface comprises plasmonic crystals or an array of plasmonic structures. For example, the plasmonic structures may be periodic TiO—Au—TiO structures.

Also disclosed herein is a process for producing the solid surface of any one of claims 50-63, which process comprising:
a) performing a first lithography step to etch into substrate;
b) depositing Ag or Al with a Ti cap by electron beam evaporation and lifting off the substrate;
c) passivating the solid surface with a CVD oxidation layer;
d) depositing hexamethyl-disilazane (HMDS);
e) performing a second lithography step to define a primer adhesion site; and
f) removing HMDS, so as to produce the surface enhanced Raman scattering (SERS) solid surface.

In various embodiments the nucleic acid samples, DNA, RNA, primer or probe are separated in discrete compartments, wells or depressions on a surface.

In this invention methods are provided wherein about 1000 or fewer copies of the nucleic acid sample, DNA, RNA, primer or probe, are bound to the solid substrate. This invention also provides the instant invention wherein $2 \times 10^7$, $1 \times 10^7$, $1 \times 10^6$ or $1 \times 10^4$ or fewer copies of the nucleic acid sample, DNA, RNA, primer or probe are bound to the solid substrate.

In some embodiments, the immobilized nucleic acid sample, DNA, RNA, primer or probe is immobilized at a high density. This invention also provides the instant invention wherein over or up to $1 \times 10^7$, $1 \times 10^8$, $1 \times 10^9$ copies of the nucleic acid sample, DNA, RNA, primer or probe, are bound to the solid substrate.

In other embodiments of the methods and/or compositions of this invention, the DNA is single-stranded. In an embodiment of the methods or of the compositions described herein, the RNA is single-stranded.

In certain embodiments, UV light is used to photochemically cleave the photochemically cleavable linkers and moieties. In an embodiment, the photocleavable linker is a 2-nitrobenzyl moiety. In an embodiment of the processes and methods described herein monochromatic light is used to irradiate Raman-label-containing nucleotide analogues (e.g. incorporated into a primer or DNA extension product) so as to elicit a signal measurable by Raman spectroscopy. In one such embodiment, the laser is a 532 nm, 633 nm, or 785 nm laser. In another such embodiment, near infra-red light is used to irradiate Raman-label-containing nucleotide analogues. In certain embodiments of the processes and methods of this invention near infra-red light is used to irradiate Raman-label-containing polynucleotide analogues.

Methods for production of cleavably capped and/or cleavably linked nucleotide analogues are disclosed in U.S. Pat. No. 6,664,079, which is hereby incorporated by reference.

A "nucleotide residue" is a single nucleotide in the state it exists after being incorporated into, and thereby becoming a monomer of, a polynucleotide. Thus, a nucleotide residue is a nucleotide monomer of a polynucleotide, e.g. DNA, which is bound to an adjacent nucleotide monomer of the polynucleotide through a phosphodiester bond at the 3' position of its sugar and is bound to a second adjacent nucleotide monomer through its phosphate group, with the exceptions that (i) a 3' terminal nucleotide residue is only bound to one adjacent nucleotide monomer of the polynucleotide by a phosphodiester bond from its phosphate group, and (ii) a 5' terminal nucleotide residue is only bound to one adjacent nucleotide monomer of the polynucleotide by a phosphodiester bond from the 3' position of its sugar.

Because of well-understood base-pairing rules, determining the wavenumber of the Raman spectroscopy peak or wavenumber of the FTIR peak of a dNTP analogue incorporated into a primer or DNA extension product, and thereby the identity of the dNTP analogue that was incorporated, permits identification of the complementary nucleotide residue in the single stranded polynucleotide that the primer or DNA extension product is hybridized to. Thus, if the dNTP analogue that was incorporated has a unique wavenumber in the Raman spectroscopy peak identifying it as comprising an adenine, a thymine, a cytosine, or a guanine, then the complementary nucleotide residue in the single stranded DNA is identified as a thymine, an adenine, a guanine or a cytosine, respectively. The purine adenine (A) pairs with the pyrimidine thymine (T). The pyrimidine cytosine (C) pairs with the purine guanine (G). Similarly, with regard to RNA, if the dNTP analogue that was incorporated comprises an adenine, a uracil, a cytosine, or a guanine, then the complementary nucleotide residue in the single stranded RNA is identified as a uracil, an adenine, a guanine or a cytosine, respectively.

Incorporation into an oligonucleotide or polynucleotide (such as a primer or DNA extension strand) of a dNTP analogue means the formation of a phosphodiester bond between the 3' carbon atom of the 3' terminal nucleotide residue of the polynucleotide and the 5' carbon atom of the dNTP analogue resulting in the loss of pyrophosphate from the dNTP analogue.

As used herein, a deoxyribonucleoside triphosphate (dNTP) analogue, unless otherwise indicated, is a dNTP having substituted in the 3'-OH group of the sugar thereof, in place of the H atom of the 3'-OH group, or connected via a linker to the base thereof, a chemical group which has Raman spectroscopy peak with wavenumber of from 2000 $cm^{-1}$ to 2300 $cm^{-1}$ or FTIR peak wavenumber of from 2000 $cm^{-1}$ to 2300 $cm^{-1}$ and which does not prevent the dNTP analogue from being incorporated into a polynucleotide, such as DNA, by formation of a phosphodiester bond. Similarly, a deoxyribonucleotide analogue residue is deoxyribonucleotide analogue which has been incorporated into a polynucleotide and which still comprises its chemical group having a Raman spectroscopy peak with wavenumber of from 2000 $cm^{-1}$ to 2300 $cm^{-1}$ or FTIR peak with wavenumber of from 2000 $cm^{-1}$ to 2300 $cm^{-1}$. In a preferred embodiment of the deoxyribonucleoside triphosphate analogue, the chemical group is substituted in the 3'-OH group of the sugar thereof, in place of the H atom of the 3'-OH group. In a preferred embodiment of the deoxyribonucleotide analogue residue, the chemical group is substituted in the 3'-OH group of the sugar thereof, in place of the H atom of the 3'-OH group. In an embodiment the chemical group has a Raman spectroscopy peak with wavenumber of from 2000 $cm^{-1}$ to 2300 $cm^{-1}$.

As used herein, a ribonucleoside triphosphate (rNTP) analogue, unless otherwise indicated, is an rNTP having substituted in the 3'-OH group of the sugar thereof, in place of the H atom of the 3'-OH group, or connected via a linker to the base thereof, a chemical group which has a Raman spectroscopy peak with wavenumber of from 2000 $cm^{-1}$ to 2300 $cm^{-1}$ or FTIR peak with wavenumber of from 2000 $cm^{-1}$ to 2300 $cm^{-1}$ and which does not prevent the rNTP analogue from being incorporated into a polynucleotide, such as RNA, by formation of a phosphodiester bond. Similarly, a ribonucleotide analogue residue is ribonucleotide analogue which has been incorporated into a polynucleotide and which still comprises its chemical group having a Raman spectroscopy peak with wavenumber of from 2000 $cm^{-1}$ to 2300 $cm^{-1}$ or FTIR peak with wavenumber of from 2000 $cm^{-1}$ to 2300 $cm^{-1}$. In a preferred embodiment of the ribonucleoside triphosphate analogue, the chemical group is substituted in the 3'-OH group of the sugar thereof, in place of the H atom of the 3'-OH group. In a preferred embodiment of the ribonucleotide analogue residue, the chemical group is substituted in the 3'-OH group of the sugar thereof, in place of the H atom of the 3'-OH group. In an embodiment the chemical group has a Raman spectroscopy peak with wavenumber of from 2000 $cm^{-1}$ to 2300 $cm^{-1}$.

A Raman spectroscopy system, as can be used in the methods described herein, typically comprises an excitation source (such as a laser, including a laser diode in appropriate configuration, or two or more lasers), a sample illumination system and light collection optics, a wavelength selector (such as a filter or spectrophotometer), and a detection apparatus (such as a CCD, a photodiode array, or a photomultiplier). Interference (notch) filters with cut-off spectral range of ±80-120 cm−1 from the laser line can be used for stray light elimination. Holographic gratings can be used. Double and triple spectrometers allow taking Raman spectra without use of notch filters. Photodiode Arrays (PDA) or a Charge-Coupled Devices (CCD) can be used to detect Raman scattered light. In an embodiment, surface enhanced Raman spectroscopy (SERS) is used which employs a surface treated with one or more of certain metals known in the art to cause SERS effects. In an embodiment the surface is a surface to which the polynucleotide, single-stranded DNA, single-stranded RNA, primer, DNA extension strand or oligonucleotide probe of the methods described herein is attached. Many suitable metals are known in the art. In an embodiment the surface is electrochemically etched silver or treated with/comprises silver and/or gold colloids with average particle size below 20 nm. The wavenumber of the Raman spectroscopy peak of an entity is identified by irradiating the entity with the excitation source, such as a laser, and collecting the resulting Raman spectrum using a detection apparatus. The wavenumber of the Raman spectroscopy peak is determined from the Raman spectrum. In an embodiment, the spectrum measured is from 2000 $cm^{-1}$ to 2300 $cm^{-1}$ and the wavenumber of the Raman spectroscopy peak is the peak wavenumber within that spectrum. In an embodiment the spectrum measured is a sub-range of 2000 $cm^{-1}$ to 2300 $cm^{-1}$ and the Raman spectroscopy peak wavenumber is the peak wavenumber within that spectrum sub-range.

FTIR systems as can be used with the FTIR methods described herein are well-known in the art, for example grazing angle FTIR.

Where a range of values is provided, unless the context clearly dictates otherwise, it is understood that each intervening integer of the value, and each tenth of each intervening integer of the value, unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding (i) either or (ii) both of those included limits are also included in the invention.

All combinations of the various elements described herein are within the scope of the invention. All sub-combinations of the various elements described herein are also within the scope of the invention.

This invention will be better understood by reference to the Experimental Details which follow, but those skilled in the art will readily appreciate that the specific experiments detailed are only illustrative of the invention as described more fully in the claims which follow thereafter.

Experimental Details

Here an enhanced high-sensitivity, high-resolution detection system, Surface-Enhanced Raman Scattering (SERS), which takes advantage of unique 3'-O-azidomethyl-modified nucleotide reversible terminators (3'-O—$N_3$-NRTs), is used for SBS. The SERS detection sensitivity can approach single molecule level.[17] Thus SERS-SBS is able to provide a high-throughput and high-sensitivity SBS approach, which complements fluorescent SBS and pyrosequencing. The methods and compositions described herein below can be alternatively be used for FTIR-based detection, mutatis mutandis. As seen in the results herein, a library of tags have been identified with Raman peaks in the region of 200-2300 $cm^{-1}$, preferably 2100-2250 $cm^{-1}$, where DNA and proteins have no Raman peaks. It is also demonstrated that using the azidomethyl group is excellent in terms of sensitivity.

Because these 3'-O—$N_3$-NRTs do not require the attachment of fluorescent tags, their cost of synthesis is substantially less than those that do. They are much smaller than their counterparts with fluorescent tags, which increase their incorporation efficiency by DNA polymerase. After cleavage, the $N_3$ is completely destroyed yielding no Raman signal at ~2100 $cm^{-1}$. In addition, the extended chain is identical to natural DNA. Many current approaches for SBS require the use of modified nucleotides that leave short remnants of the linkers that were used to attach the fluorescent tags; as these build up in the extended DNA chains, they are more and more likely to alter the DNA structure so as to impede further nucleotide incorporation. Finally, the conditions for removal of the azidomethyl group to allow the next cycle of incorporation and detection is well established, and has been shown to be compatible with DNA stability (15, 18).

SERS-SBS is a unique approach that to our knowledge has not been tested for DNA sequencing outside of our laboratory. There are several innovative aspects all accomplished by the use of 3'-O—$N_3$-NRTs in this sequencing strategy: (1) a ready mode of detection available in the Surface-Enhanced Raman Scattering technique; (2) a means of overcoming errors, particularly in reading through homopolymer stretches, thanks to the presence of the reversible terminating group; (3) the elimination of the problem of fluorescence background; (4) increased processivity of the enzyme reaction thanks to the absence of any modifications on the previously incorporated nucleotides; (5) relatively low cost of synthesis compared to fluorescently tagged nucleotides; and (6) ease of removal of the azidomethyl moiety with established and DNA-compatible chemistry (TCEP cleavage of the azidomethyl group restores the —OH). Further innovation in the use of the SERS technique is achieved by its high sensitivity and excellent resolution.

A further innovation is the use of a library of different nucleotides with distinct chemical side groups on the azidomethyl moiety, one for each of the 4 bases. These are chosen so as to generate unique or multiple Raman band shifts and therefore unique signatures for each base, analogous to 4-color DNA sequencing. Identification of which analogues can perform these functions and be incorporated by a polymerase is critical.

Thus, a major innovation here is a technology that includes both cost and throughput advantages with the goal of achieving the $1000 genome, but also doing this at high sensitivity, and increasing the number of DNA molecules that can be sequenced in parallel. It is apparent that the same molecules can be utilized as well for non-genomic sequencing, such as direct RNA-Seq. In fact, the use of the SERS approach, with the azidomethyl moiety located instead at positions that do not cause termination, is compatible with other approaches, including exonuclease-based sequencing.

DNA Sequencing by Synthesis Using Reversible Terminators with Cleavable Fluorescent Tags:

Over the last 10 years, a wide variety of chemistries and technologies to support the sequencing by synthesis (SBS) strategy have been developed. This includes the use of fluorescent and mass tags to reveal the specific incorporation of nucleotides containing each of the 4 bases, various surface attachment strategies to enable solid-phase SBS, and sophisticated hybrid strategies (mixed dNTP/NRT strategies to maximize length, pyrosequencing with NRTs, a novel walking and sequencing strategy using the SBS platform) (10, 14-16, 22-26). Since much of this work has been published, here only the basic approach is briefly described with some specific examples.

Upon examining X-ray diffraction-based models of the interactions of a DNA template, DNA primer, and an incoming dNTP at the reaction center of DNA polymerase (28), it became apparent that only a few sites on the nucleotide were sufficiently free of steric hindrance and ionic interference to support the attachment of side groups and still permit the polymerase reaction to occur with good efficiency and specificity. By attaching small cleavable chemical groups to the 3'-OH site on the sugar, and larger fluorescent or mass tags to the bases via cleavable linkers, libraries of molecules were created that could temporarily stop the incorporation of additional nucleotides, and provide a specific means of identifying the incorporated nucleotide. Subsequently, both the blocking group and the tags could be removed by chemical or photocleavage reactions, in preparation for the next round of DNA incorporation (10, 14, 18). Among the variety of 3'-OH modifications tested, three were followed with particular avidity, based on their efficiency of incorporation, ease of cleavage with agents that were not damaging to the DNA, and specificity. These included the 2-nitrobenzyl group which could be removed by exposure to near-UV light (23) the allyl group which could be cleaved via a Pd-catalyzed reaction (14) and the azidomethyl group which is cleavable by treatment under mild conditions with Tris-(2-carboxyethyl)phosphine (TCEP) (15). For attachment of the fluorescent labels, an assortment of linkers that also incorporated these three groups allowing cleavage by the same means were generated.

In FIG. 1, the approach with a set of 4 nucleotides possessing both cleavable tags and cleavable blocking groups is shown, using for simplicity the class of compounds containing an azido group at the 3'-OH and within the linker to the fluorophores (18). As shown, after an initial polymerase reaction, the hybridized primer is extended by a nucleotide complementary to the next available base in the template DNA. Because of the presence of the blocking group, the reaction is terminated at that position, and because of its specific fluorescent tag, the base can be determined. Subsequently, TCEP is added to cleave both the blocking group and the fluorescent tag, at which point the stage is set for the next round of sequencing (incorporation-detection-cleavage). Both short and longer flexible linkers have been utilized to attach the fluors, which upon cleavage leave a smaller remnant. This is important as these remnants may have a cumulative effect on the structure of the growing DNA chain that will eventually make it difficult for the polymerase to recognize it as a good substrate for further reactions, thereby placing a ceiling on the potential read length. Also shown in FIG. 1 is the use of an intermediate synchronization step in which NRTs without attached dyes are added; these are more efficiently incorporated than the labeled NRTs, and allow incomplete ("lagging") reactions from the prior step to "catch up".

In another approach, a hybrid between the massively parallel possibilities of SBS and the long sequence reads enabled by Sanger sequencing, 3'-O-modified nucleotide reversible terminators and much smaller amounts of chemically cleavable fluorescent dideoxynucleosides (ddNTPs) which permanently terminate the reaction have been utilized at the same time (15). The principle is that sufficient signal is obtained from the labeled permanent terminators, even though the small percent of strands into which they are incorporated are lost from future reactions. In the meantime, the reversible terminators are available to drive subsequent steps, and because the free 3'-OH groups are regenerated in each round, and there are no remnant-leaving linkers on these NRTs, the reactions should progress smoothly. By varying the ratios of the labeled ddNTPs and the unlabeled NTPs in each round, longer sequencing reads than with NRTs with attached dyes have been achieved.

DNA Sequencing by Synthesis Using 3'-azidomethyl Modified NRTs and Infrared Spectroscopic (IR) Detection.

Figure 2:
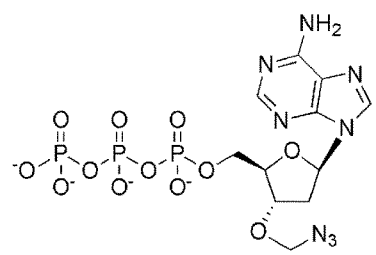
FIG. 2. A set of four 3'-O-azidomethyl nucleotide reversible terminators that can be used for SBS with solution and solid substrate Raman and SERS detection.
Figure 2:
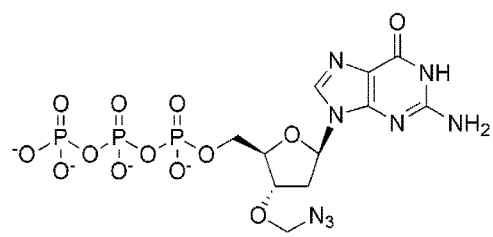
Figure 2:
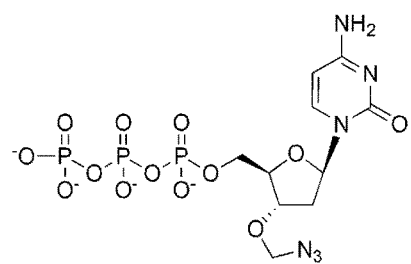
Figure 2:
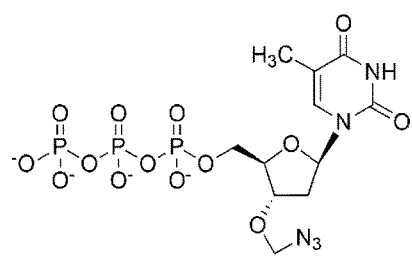
Figure 3:
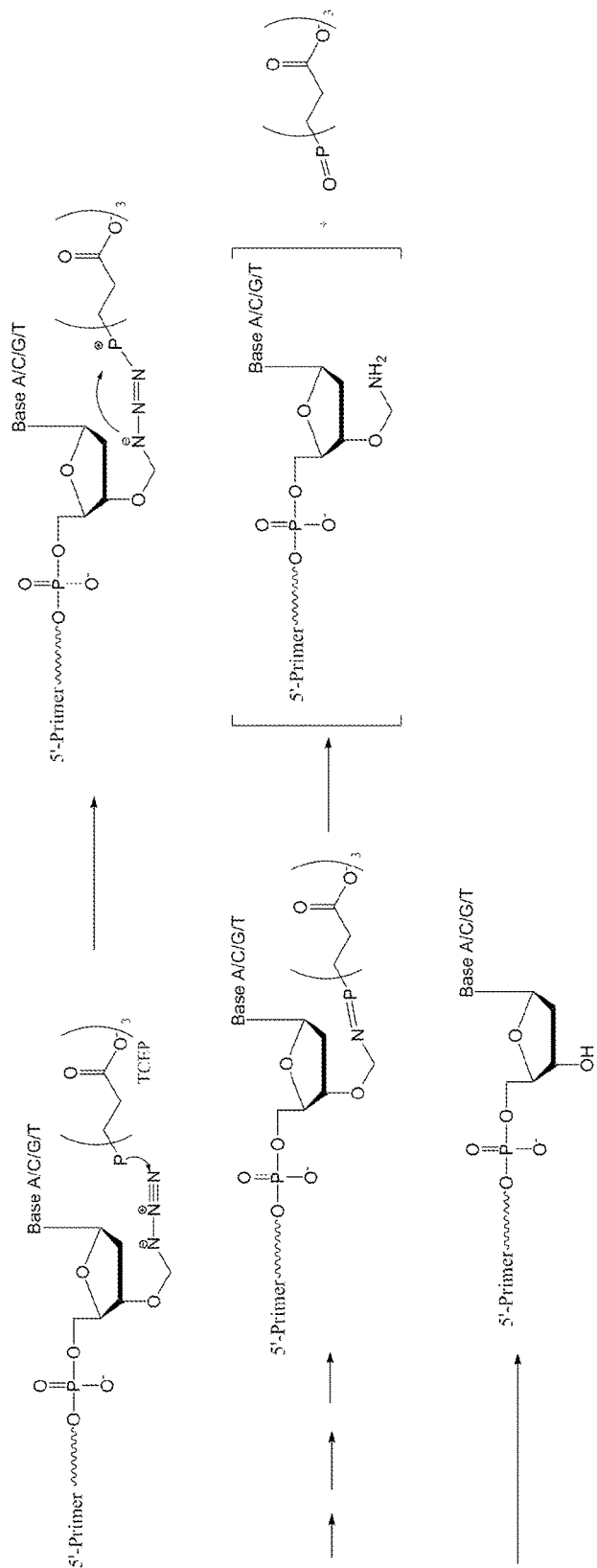
FIG. 3. Mechanism of 3'-O-azidomethyl cleavage by Tris-(2-carboxyethyl)phosphine (TCEP) to regenerate the 3'-OH.
Figure 4:
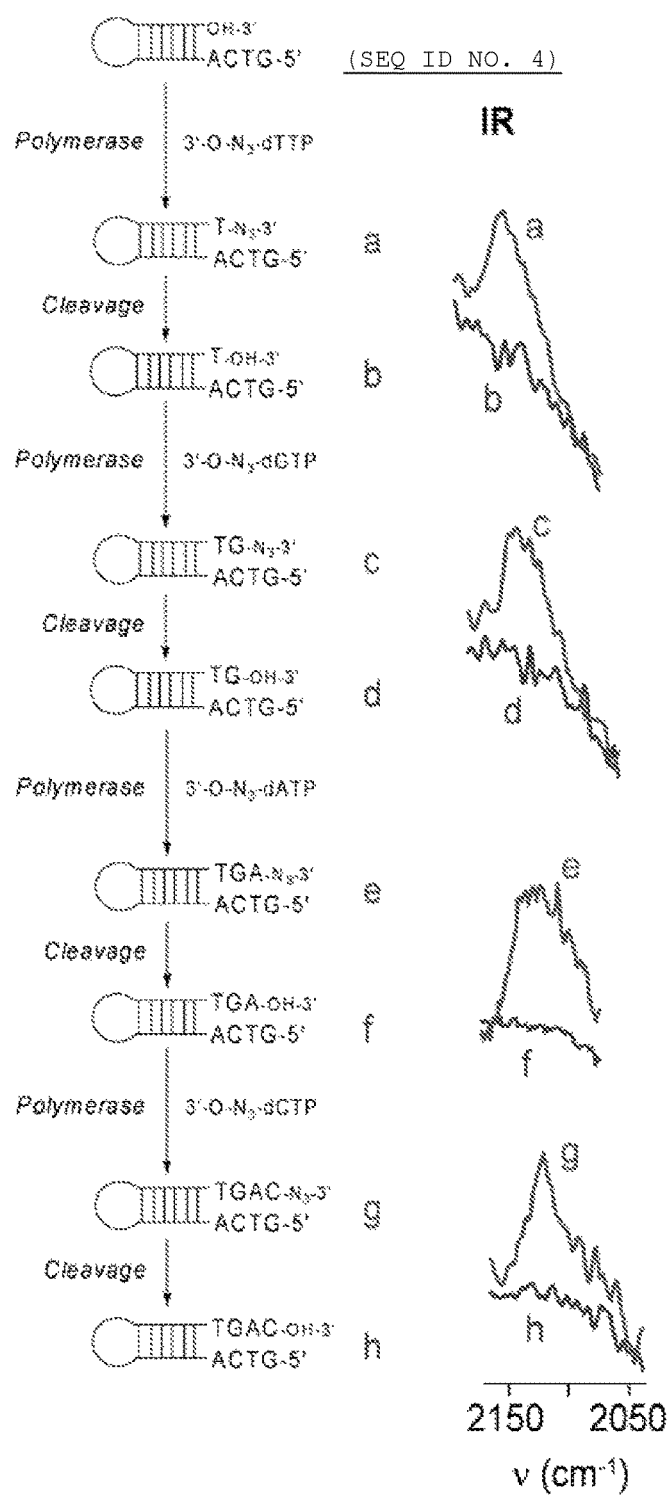
FIG. 4. Experimental scheme of continuous IR-SBS using 3'-azidomethyl modified NRTs (Left) and the Fourier-transform infrared (FTIR) spectra (Right) of the products from each step (light gray, N$_3$ IR signal on the DNA extension products; dark gray, IR signal of the DNA extension products with the azidomethyl group removed). Only the portion of the FTIR spectrum in the range from 2150 cm$^{-1}$ to 2050 cm$^{-1}$ (from left to right) is shown, the azide (N$_3$) peak appearing at 2115 cm$^{-1}$.

Here the unique infrared absorbance at 2115 cm$^{-1}$ of the azido group ($N_3$) in the 3'-azidomethyl modified NRTs (FIG. 2) is disclosed for DNA sequence detection. In this approach, the incorporation of the 3'-azidomethyl modified NRTs into the growing strand of DNA temporarily terminates the polymerase reaction. Instead of engineering a fluorescent dye as a reporter group on the bases, or detecting the released pyrophosphate, here the azidomethyl capping moiety on the 3'-OH serves double duty: as the reversible termination group (FIG. 3), and also as the reporter group to indicate the incorporation of the complementary base. The infrared spectrum for the azido ($N_3$) group (~2115 cm$^{-1}$) is strong and unique while none of the groups in DNA have IR signals in this region. Thus, $N_3$ serves as an IR label for DNA sequencing by synthesis (SBS) (FIG. 4). Compared with pyrosequencing, IR-SBS using 3'-azidomethyl modified NRTs has the following advantages: (1) Throughput is much higher than pyrosequencing, because the $N_3$ tag is directly attached on the DNA, which allows a higher density of DNA templates to be attached on a solid surface without any cross talk; (2) All the growing strands in IR-SBS are natural DNA molecules and sequence determination is a direct detection approach; in contrast, pyrosequencing is an indirect detection method; (3) the sequencing device can be miniaturized as it only requires a narrow spectral region around 2100 cm$^{-1}$.

Because the $N_3$ group in the 3'-azidomethyl modified NRTs also has a Raman band at ~2100 cm$^{-1}$, Surface-enhanced Raman scattering (SERS) of the $N_3$ group can be used for an SERS-SBS approach. The SERS detection sensitivity can approach single molecule level (17). Thus SERS-SBS is able to provide a high-throughput and high-sensitivity SBS approach, which complements fluorescent SBS and pyrosequencing.

DNA Sequencing by Synthesis Using 3'-azidomethyl Modified NRTs and Raman Detection.

Figure 5:
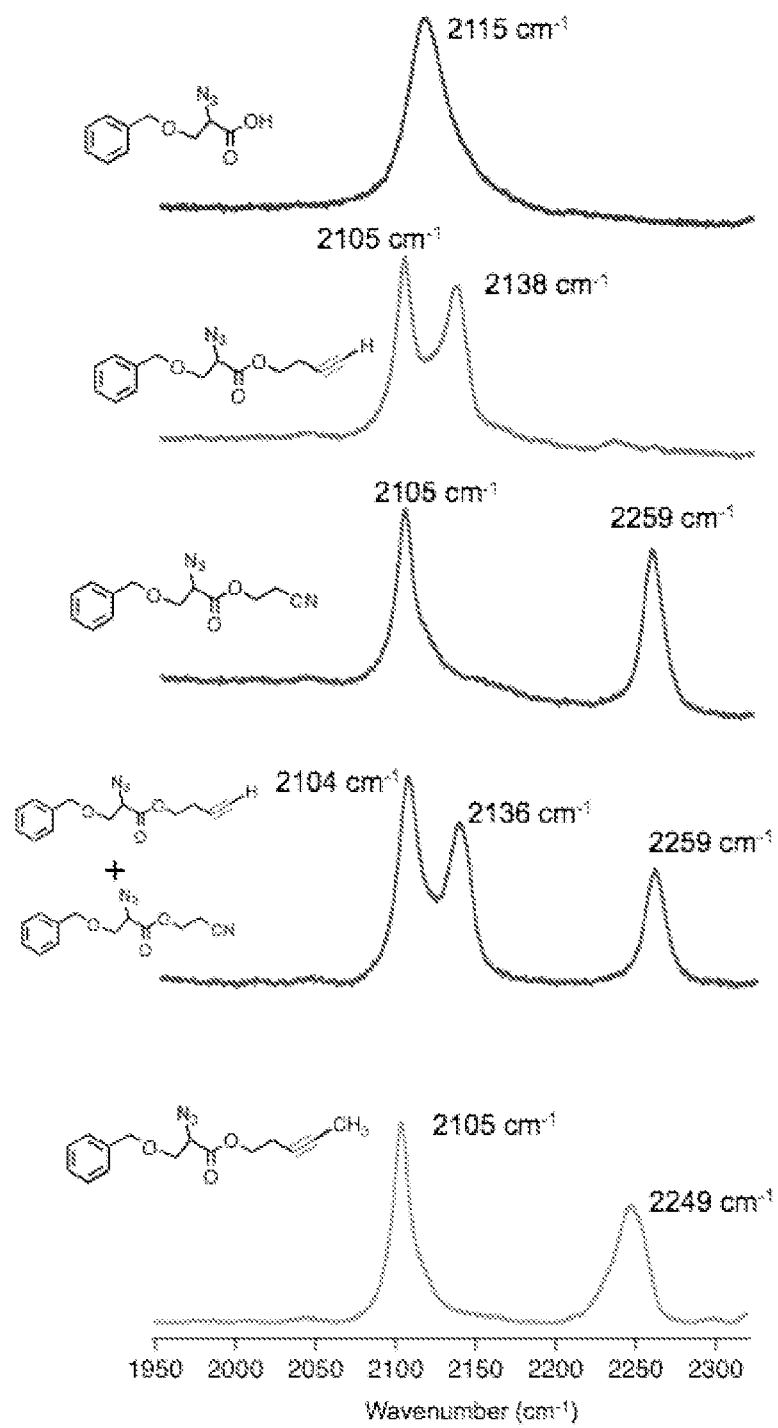
FIG. 5. Raman spectra of 4 chemical tags from 2100 cm$^{-1}$ to 2260 cm$^{-1}$, where DNA and protein have no Raman peaks. The four tags (—N$_3$, —CN, —C≡C—H, and —C≡C—CH$_3$) with strong Raman peaks at 2105 cm$^{-1}$ (—N₃), 2138 cm⁻¹ (—C≡CH), 2249 cm⁻¹ (—C≡C—CH₃), 2259 cm⁻¹ (—CN) are used to label A, C, G, and T in the "4-signal" Raman SBS.

As an initial test of the potential of the Raman detection with SBS, four model compounds were selected with 4 different Raman tags (—$N_3$, —CN, —C≡CH, and —C≡C—$CH_H$) as shown in FIG. 5. As seen in the spectra, appropriate fairly sharp Raman peaks with each of these compounds were obtained. The $N_3$ peak appears at ~2105 cm$^{-1}$, the alkyne peak at ~2138 cm$^{-1}$, the methyl-substituted alkyne peak at ~2249 cm$^{-1}$, and the cyano peak at ~2259 cm$^{-1}$. Importantly, in compounds with two different tags and in compound mixtures, all the expected peaks appear and at near equal stoichiometry at the appropriate wavenumber, where DNA and protein have no Raman peaks.

Surfaced Enhanced Raman Scattering (SERS) of Model Compounds.

Figure 6:
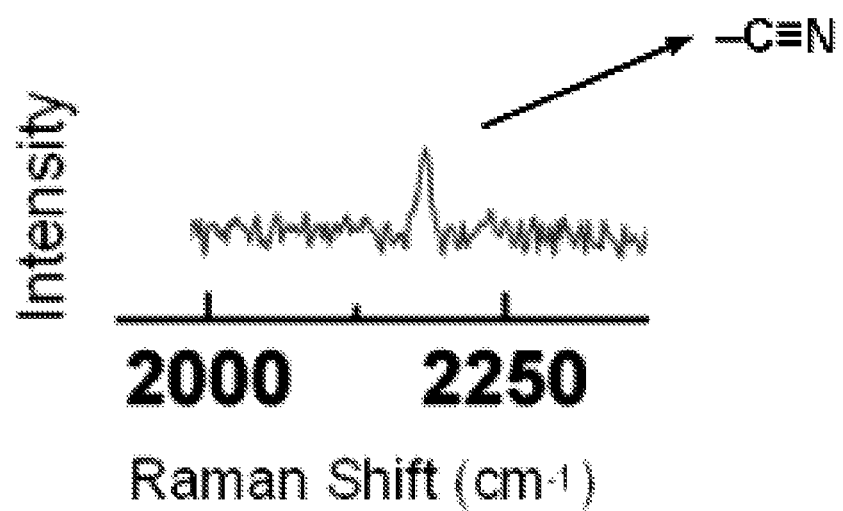
FIG. 6. SERS spectra of RH800, showing single molecule SERS events for the cyano (—C≡N) group.

SERS has been shown to be able to detect a variety of molecules at the single molecule level. For example, recent reports provide evidence that single molecular detection (SMD) is strongly linked to localized surface plasmonic resonance (LSPR) supporting nanostructures; single molecule Raman detection of a cyano group (—C≡N) in Rhodamine 800 (FIG. 6) (33); and single-molecule surface-enhanced Raman spectroscopy of crystal violet obtaining an overall enhancement of 2.6×10$^9$ from eight SM-SERS events (34). In addition, it has been shown that <100 molecules were detectable using urchin-like silver nanowire as SERS substrate and 10$^{-16}$ M surface adsorbed Rhodamine 6G (30).

Raman and SERS Experiments.

Figure 7:
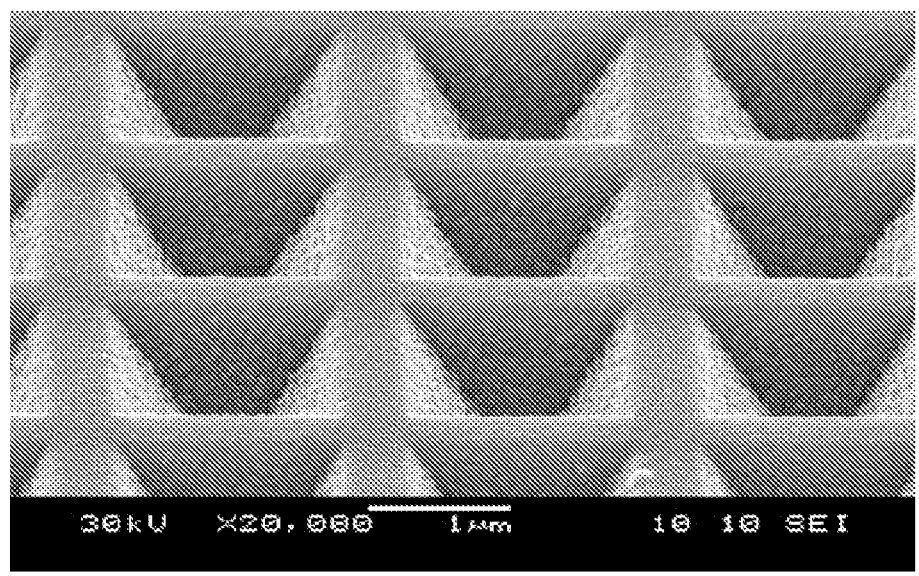
FIG. 7. Scanning electron micrograph of Au-coated, lithographically patterned Klarite substrate.

Test compounds synthesized (2-azido-3-(benzyloxy)propanoic acid (C1) containing an azido (—$N_3$) group and 2-cyanoethyl 2-azido-3-(benzyloxy)propanoate (C2) containing both an $N_3$ and cyano (—C≡N) moiety (FIG. 5)) were dissolved in methanol and diluted. An aliquot was applied to a SERS substrate or glass slide for measurement. An aluminum reference surface was used as a control. The Klarite (Renishaw Diagnostics, Ltd.) substrate consisting of a 4 mm×4 mm nano-patterned SERS active area in which Au was layered in an inverted pyramid array (FIG. 7) was used as the SERS surface. Typically, five measurements were obtained across each substrate surface.

Characterization of SERS Enhancement Factors.

Raman signals of the C1 and C2 adsorbed samples were measured and compared with the aluminum reference substrate. The analytical enhancement factor (AEF) was defined as:

$$AEF = \frac{I_{SERS}/c_{SERS}}{I_{RS}/c_{RS}}$$

where:
$I_{SERS}$=SERS signal intensity
$I_{RS}$=Raman signal intensity of aluminum reference
$c_{SERS}$=analyte solution concentration under non-SERS condition
$c_{RS}$=analyte concentration on SERS substrate Results of Model Raman Tag Measurements.

Figure 8:
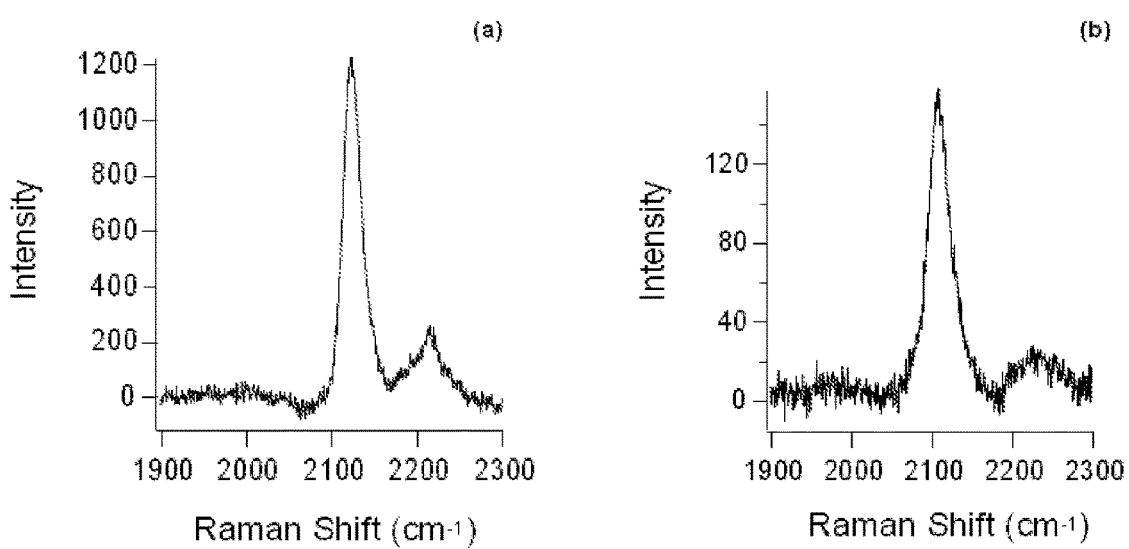
FIG. 8. Experimental high enhancement factor for azido (—N₃) chemical tag. (a) Typical Raman spectra of 1 μM solution coated on Klarite substrate and the corresponding reference Raman spectra of 100 mM solution coated on aluminum (b).

Using various analyte dilutions, an area-average SERS enhancement of ~8×10$^5$ ($N_3$ compound) and ~5×10$^5$ (CN compound) were achieved over the entire SERS-active area. The averaged and background removed Raman peaks for the azido compound is shown in FIG. 8 for both Klarite (red) and aluminum reference (blue). The resulted EF was close to the defined theoretical maximum of ~10$^6$. The results may be further improved using a nanoengineering approach to create optimal SERS surfaces or plasmonic systems.

Figure 24:
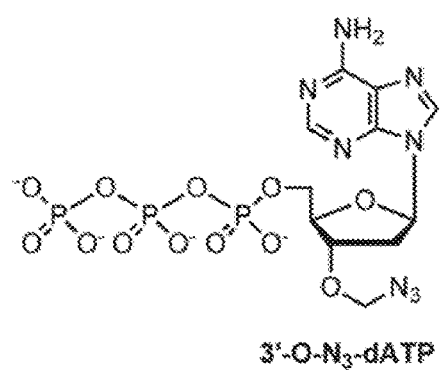
FIG. 24. Structures of the nucleotide reversible terminators, 3'-O—N₃-dATP, 3'-O—N₃-dTTP, 3'-O—N₃-dGTP, and 3'-O—N₃-dCTP.
Figure 24:
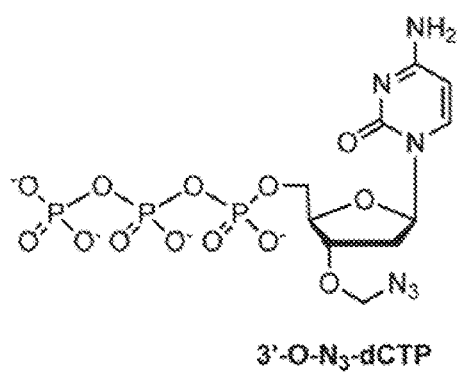
Figure 24:
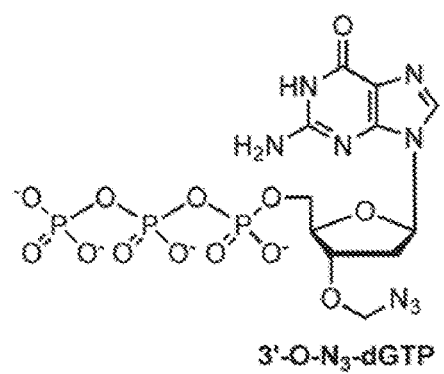
Figure 24:
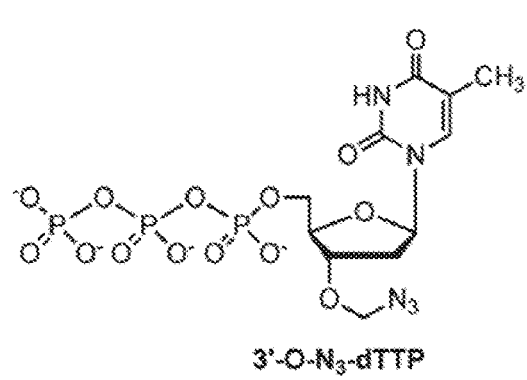

Successful DNA SBS using SERS with a commercially available structured gold surface and a synthetic template and primer has been shown. In this SERS-SBS approach, the 3'-OH groups of the reporter nucleotides are capped with an azidomethyl moiety (15), as shown in FIG. 24, to temporarily terminate the polymerase reaction after incorporation. Instead of engineering a fluorescent dye as a reporter group on the bases, here the same azidomethyl capping moiety serves as the reporter group to indicate the incorporation of a base complementary to that in the template into a growing DNA chain. The azide group is ideally suited as a Raman reporter group, because of its distinct Raman shift at 2080-2170 cm$^{-1}$, a spectral region where DNA, proteins and most other molecules do not elicit signals.

Because these 3'-O-azidomethyl-dNTPs (3'-O—N$_3$-dNTPs) do not require the attachment of fluorescent tags, their cost of synthesis is substantially lower. They are much smaller than their counterparts with fluorescent tags, which increase their incorporation efficiency by DNA polymerase. In addition, the extended chain is identical to natural DNA, unlike many current SBS approaches, which require the use of modified nucleotides that leave short remnants of the linkers used to attach the fluorescent tags; as these build up in the extended DNA chains, they are increasingly likely to alter DNA structure and impede further nucleotide incorporation. After cleavage, the N$_3$ is completely destroyed yielding no Raman signal at ~2125 cm$^{-1}$. Finally, the method for removal of the azidomethyl group to allow the next cycle of incorporation and detection is well established and has been shown to be highly compatible with DNA stability (15).

Figure 9:
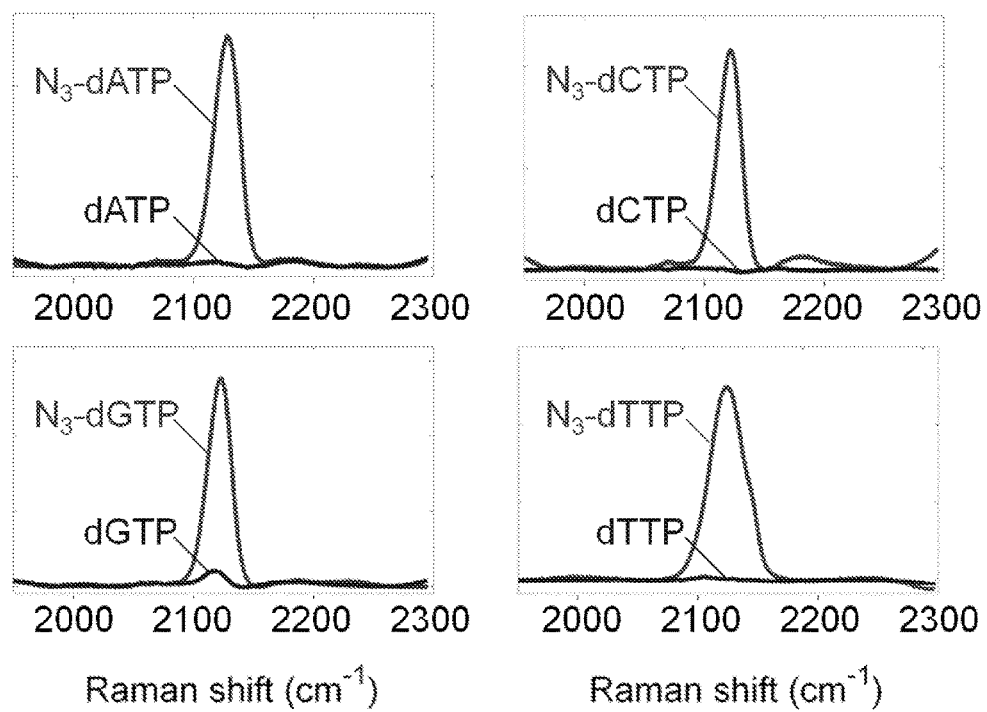
FIG. 9. Raman signal of 3'-O—N₃-dNTPs (N₃-dNTPs) (red) and natural dNTPs (blue). In all 4 cases, there is a 10²-fold signal increase at the expected Raman shift of ~2125 cm⁻¹ due to the N₃ group.

Before proceeding with the SBS experiment, the four 3'-O-azidomethyl-modified nucleotides are shown to generate appropriate Raman signals relative to the natural nucleotides. These serve to mimic the nucleotides incorporated into the growing strand of DNA before and after TCEP cleavage, respectively. Indeed, the four 3'-O—N$_3$-dNTPs display enhanced Raman scattering at ~2125 cm$^{-1}$ on Klarite SERS substrates, while the natural dNTPs produce only a background signal (FIG. 9).

Figure 10:
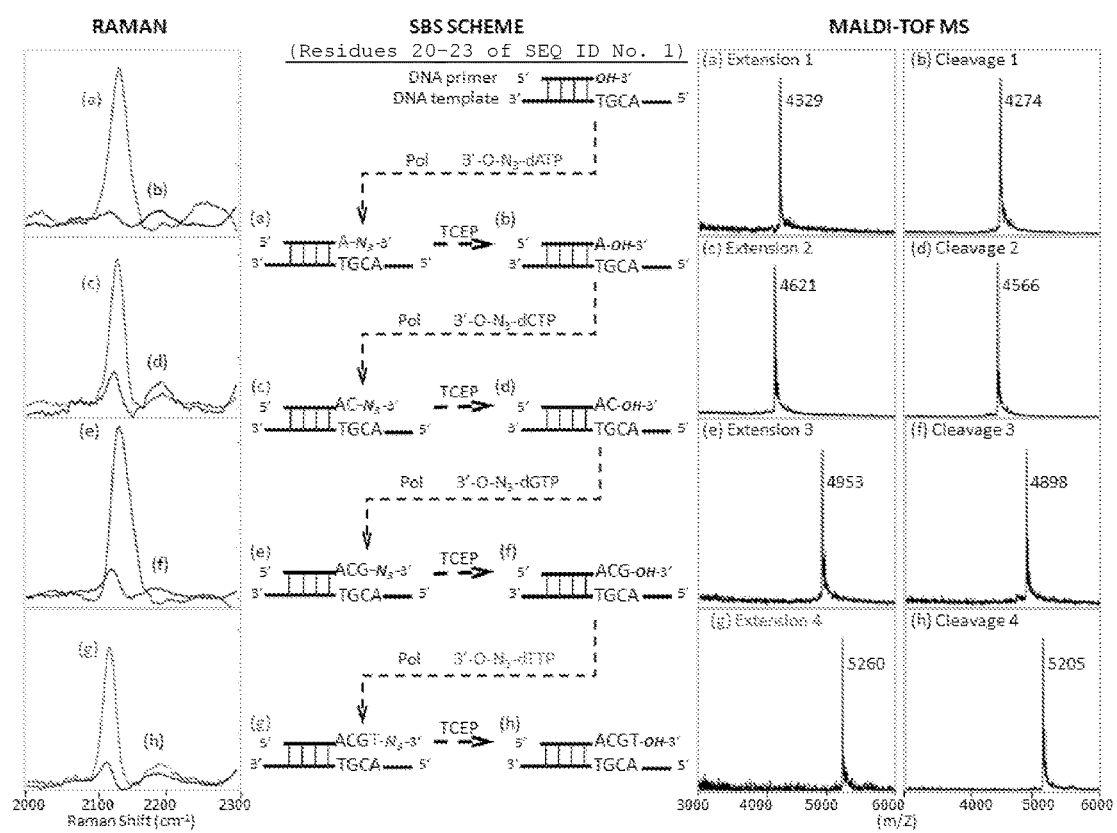
FIG. 10. Scheme of continuous DNA sequencing by synthesis (middle) using reversible terminators, 3'-O—N₃-dNTPs, with Raman (left) and MALDI-TOF MS spectra (right) obtained at each step. Only the 2000-2300 cm⁻¹ Raman interval is shown, the azide peak appearing at Raman shift ~2125 cm⁻¹. Pol=DNA polymerase.

Consecutive incorporation, detection and cleavage of each of the four nucleotides bearing 3'-O-azidomethyl blocking groups (N$_3$) using a template and linear primer is successful. The approach took advantage of a template-primer combination in which the next four nucleotides to be added were A, C, G and T. As shown in FIG. 10 (middle), a 3'-O-azidomethyl modified complementary base could be incorporated into a 13-mer primer annealing to a 51-mer DNA template. After removing all the reaction components by HPLC, the appearance of Raman spectra around 2125 cm$^{-1}$ indicated the incorporation of 3'-O—N$_3$-dNTPs into the DNA strand. Treatment with a 100 mM TCEP (tris(2-carboxyethyl)phosphine) solution was able to remove the azidomethyl group and regenerate the 3'-OH of the DNA primer, after which incorporation could be initiated for the next cycle. The experiment was initiated with the 13-mer primer annealed to a DNA template. When the first complementary base, 3'-O—N$_3$-dATP, was used in the polymerase reaction (FIG. 10, middle), the Raman spectra of the extended DNA template clearly showed a Raman shift at ~2125 cm$^{-1}$ which can be assigned to the azide stretch (FIG. 10a, left); the expected 4329 Da extension product was confirmed by MALDI-TOF MS (FIG. 10a, right). This is strong evidence that the modified nucleotide was incorporated into the DNA primer. After TCEP treatment to remove the azidomethyl group and HPLC purification, the Raman peak around 2125 cm$^{-1}$ largely disappeared, and cleavage was confirmed by an MS peak at 4274 Da (FIG. 10b). The newly formed free 3'-OH containing primers were then used in a second polymerase cycle where 3'-O—N$_3$-dCTP was added. The Raman spectra again revealed a peak at ~2125 cm$^{-1}$, and MS gave a 4621 Da peak, indicating incorporation of 3'-O—N$_3$-dCTP in this cycle (FIG. 10c); disappearance of the Raman peak after TCEP treatment and an MS peak at 4566 Da proved the removal of the azidomethyl group (FIG. 10d). FIG. 10e showed the third incorporation of 3'-O—N$_3$-dGTP into this primer to resume the N$_3$-dependent Raman signal and the disappearance of this signal after TCEP cleavage is indicated in FIG. 10f. Finally, 3'-O—N$_3$-dTTP was incorporated in the polymerase reaction in the fourth cycle, as shown in FIG. 10g, indicated by the reappearance of the N$_3$ Raman signal, and FIG. 10h shows the disappearance of this peak after azidomethyl group removal by TCEP. Again, appropriate masses were obtained by MALDI-TOF-MS for the 3$^{rd}$ and 4$^{th}$ incorporation and cleavage reactions.

DNA sequencing by synthesis using surface-enhanced Raman spectroscopy has been shown. The azidomethyl group at the 3'-OH position of the nucleotides can temporarily terminate the polymerase reaction after they are incorporated and treatment with TCEP can efficiently remove the azidomethyl group from the 3'-OH. Meanwhile, the uniqueness of the azide peak in Raman spectra makes it an excellent reporter group during SBS. Once the complementary base was incorporated into the DNA strand, a Raman peak appeared around 2125 cm$^{-1}$, otherwise, this portion of the spectrum was at background level. This method of DNA sequencing is realized with only minor nucleotide modifications. The nucleobases are intact and the DNA primer remains in its natural form as it's elongated during SBS, therefore, a longer readlength would be achieved. Though each reaction was carried out in solution and then purified and spotted on separate Klarite chips, SBS experiments can also follow continuous incorporation and cleavage on the same chip. Additionally, integration of nanoplasmonic systems together with site specific molecular interactions to yield reproducible and optimal signal enhancement can be achieved by attaching either the DNA or the polymerase to the SERS surface, permitting washing away of unreacted nucleotides and other reactants.

The high spectral quality and reproducibility of the DNA extension product spectra, which are clearly distinguishable from the Raman spectra of the cleavage products, may be used to develop a robust solid-state platform for measuring SERS signals resulting from the polymerase extension of specific oligonucleotides in SBS reactions. Furthermore, with different Raman scattering groups bearing unique spectral signatures on each of the four nucleotides, one can overcome the need to add them one at a time.

Experimental Procedures

SERS Detection of Nucleotides

The four 3'-O-azidomethyl-modified nucleotides (FIG. 24) were synthesized according to the procedure described previously (4). Each was dissolved in water to form a 100 µM solution, then a 2 µL aliquot was deposited onto individual Klarite SERS (Renishaw Diagnostics, UK) substrates and dried in ambient air to obtain a uniform molecular deposition for Raman measurements. Equivalent amounts of the natural deoxynucleotides were deposited on 4 separate SERS substrates in the same way.

Sequencing by Synthesis (SBS) Reactions

Polymerase extension reactions each consisted of 20 pmol of a synthetic 51-mer DNA template (5'-GAGGCCAAG-TACGGCGGGTACGTCCTTGACAATGTGTACAT-CAACATCACC-3'), 60 pmol of primer (5'-CACATTGT-CAAGG-3') or a previously extended and TCEP-cleaved product, 100 pmol of a single nucleotide reversible terminator (3'-O—N$_3$-dATP, 3'-O—N$_3$-dCTP, 3'-O—N$_3$-dGTP, or 3'-O—N$_3$-dTTP) (4), 1× ThermoPol reaction buffer (New England Biolabs, MA), 2 unit Therminator™ III DNA polymerase and deionized H$_2$O in a total volume of 20 µL.

Reactions were conducted in a thermal cycler (MJ Research, MA). After initial incubation at 94° C. for 20 sec, the reaction was performed for 36 cycles at 80° C. for 20 sec, 45° C. for 40 sec and 65° C. for 90 sec.

After the reaction, a small portion of the DNA extension product was desalted using a C18 ZipTip column (Millipore, Mass.) and analyzed by MALDI-TOF MS (ABI Voyager, DE). The remaining product was concentrated further under vacuum and purified by reverse phase HPLC on an XTerra MS C18 2.5 µm 4.6 mm×50 mm column (Waters, Mass.) to obtain the pure extension product (retention time ~29 min). Mobile phase: A, 8.6 mM triethylamine/100 mM 1,1,1,3,3, 3-Hexafluoro-2-propanol (HFIP) in water (pH 8.1); B, methanol. Elution was performed at 40° C. with a 0.5 mL/min flow rate, and with 88% A/12% B to 65.5% A/34.5% B linear gradient for 90 min, then 100% B isocratic for another 20 min. The purified product was used in the subsequent extension reaction.

Figure 25:
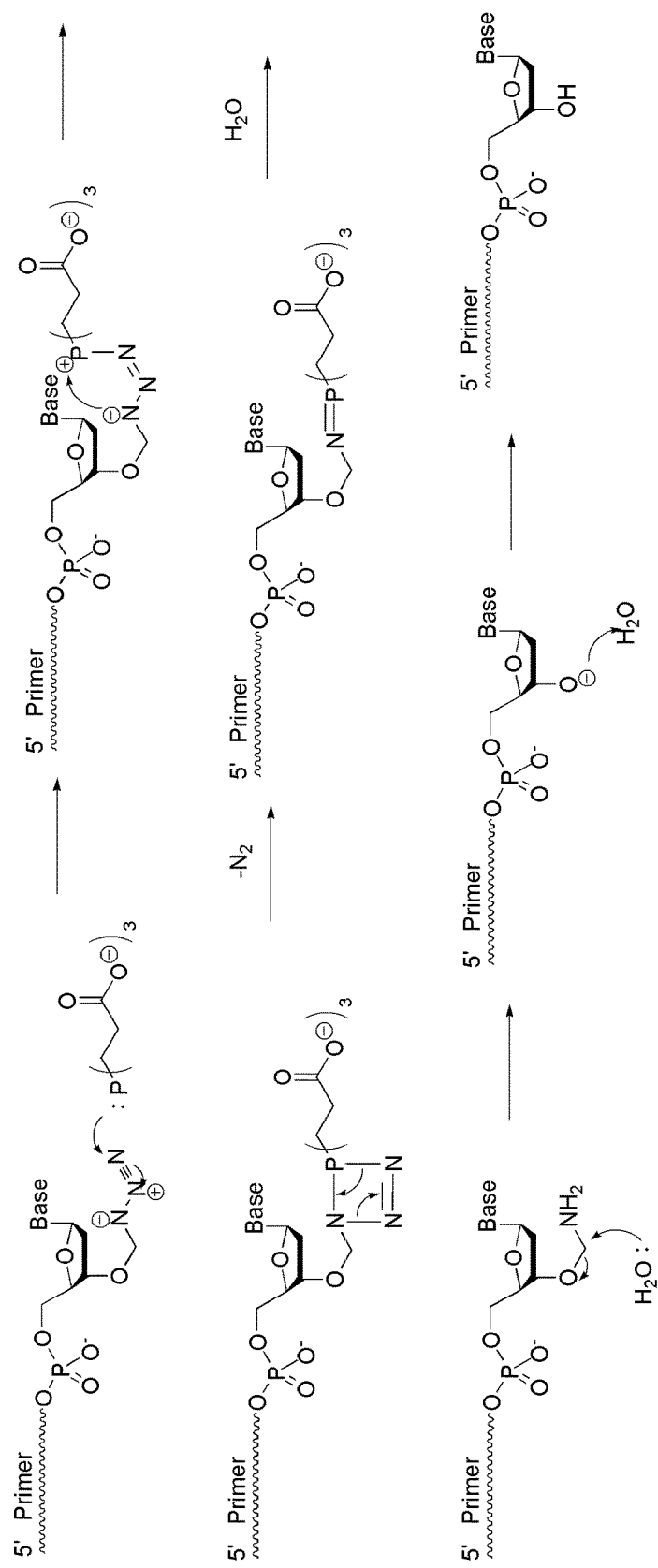
FIG. 25. Mechanisms to cleave the 3'-O-azidomethyl group from the DNA extension products with TCEP to regenerate the 3'-OH group.
Figure 26:
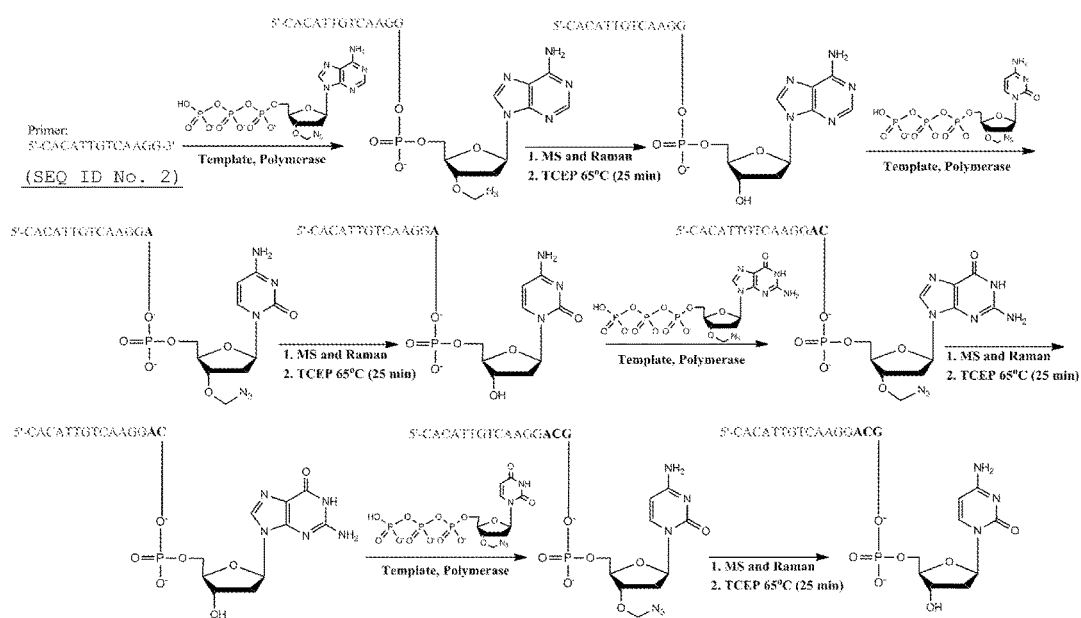
FIG. 26. Polymerase DNA extension reaction using 3'-O—N₃-dNTPs as reversible terminators.

Cleavage reactions were carried out by dissolving 100 pmol extension products in 10 µL of 100 mM Tris(2-carboxyethyl)phosphine (TCEP) solution (pH 9.0), and incubating at 65° C. for 25 min to remove the azidomethyl groups. Following dilution in 1 mL deionized $H_2O$ and desalting in an Amicon Ultra-0.5 centrifugal filter unit with Ultracel-3 membrane (Millipore), 2 µL was used to obtain the MALDI-TOF mass spectrum. Each cleavage product was used as primer in the subsequent extension reaction. The mechanism of this cleavage reaction is shown in FIG. 25. The third and the fourth extensions were carried out in a similar manner by using the previously extended and cleaved product as the primer. Four consecutive nucleotide additions are shown in FIG. 26.

SERS Detection of SBS Products

Raman spectra of the newly purified DNA extension and cleavage products were acquired with a drop coating method, in which an aliquot was deposited and dried in ambient air to obtain a uniform layer. A 3 µL aliquot of the 100 µM DNA extension products was deposited onto a Klarite SERS-active substrate (Renishaw Diagnostics); similarly, 30 pmol of cleavage products with 10 pmol spiked-in template were spotted. The added DNA was included for compatibility with the extension products, and to more closely mimic a continuous extension and cleavage reaction carried out on the same substrate.

Description of SERS Substrates

Gold-coated Klarite SERS-active substrates were purchased from Renishaw Diagnostics. The 6 mm×10 mm chip (consisting of a 4 mm×4 mm patterned region and an unpatterned Au reference area) was adhered to a standard microscope slide (25 mm×75 mm) at the foundry. The active area contains an array of micro-scaled inverted pyramids with 1.5 µm well diameter, 2 µm pitch and 1 µm depth coated with a 20 nm chrome adhesion layer below a 400 µm gold layer. Klarite slides were used only once and the storage container was opened just prior to measurement to reduce possible surface contamination.

Instrumentation

All Raman/SERS spectra were recorded using a Jobin-Yvon LabRam ARAMIS Raman microscope (Horiba, Japan) in a standard backscattering configuration with a 785 nm excitation laser. The laser beam was focused onto the sample using a 50× long working-distance (NA=0.5) dry objective (Nikon, Japan). All spectra were obtained with an exposure time of 10 sec, 5 accumulations per spot and at 34 mW laser power before the objective.

Analysis of Spectral Data

Due to potential non-uniformity of analyte deposition, a data set of N spectra (in this case, typically N=10) acquired at randomly selected regions on the same substrate was obtained. Data are presented as background removed averages of such a data set. Spectra were processed using the Savitzky-Golay fourth derivative method (window size of 25 data points), which can effectively reduce or eliminate possible false correlations resulting from a constant offset or broadband background (36, 37).

Experiments

Nucleotide reversible terminators (NRTs), 3'-O-azidomethyl derivatives of each of the four nucleotides, and a new set of compounds based on the 3'-O-azidomethyl nucleotides but further modified to produce additional Raman signals were designed. The Raman spectra of the set of azidomethyl-derivatized NRTs are characterized, as free nucleotides and when part of DNA chains, before and after cleavage of the $N_3$ group. New SERS substrates specially designed for detecting the Raman tag-containing nucleotides used in these studies are developed. SBS is conducted on surface-immobilized DNA templates using the 3'-$N_3$-NRTs and detection by Raman. A set of 4 NRTs possessing 4 unique Raman signatures are tested, one for each of the four bases of DNA; and analyzed as free nucleotides and when incorporated into DNA, before and after cleavage of the Raman detectable groups. Surface-enhanced signals are utilized, for instance the use of silver or gold nanoparticle-impregnated porous alumina surfaces (nanotubes) (29-31) attached to the sequencing chips, in order to achieve high-sensitivity detection. The system for sequencing of both surface-attached synthetic and library-derived DNA molecules will be tested.

Preparation of a Set of Nucleotides Containing 3'-O-azidomethyl Modifications and Testing Them for SBS in Solution with Raman and SERS Detection A set of 3'-O-azidomethyl derivatives of each of the four nucleotides has previously been synthesized (15). These are recognized as substrates for SBS by 9° N DNA polymerase (exo-) A485L/Y409V (New England Biolabs) with modified buffer conditions. It has been shown that these NRTs can be used to conduct SBS reactions without the use of context information-based background subtraction (15). These NRTs have been used successfully for carrying out primer walking reactions during SBS, offering the potential to substantially increase the current sequencing read length of SBS. In the past these NRTs have either been used in combination with fluorescent nucleotides, or have been further modified with cleavable linkers containing fluorescent tags. Though fluorescence measurements are highly sensitive, with the possibility of single molecule detection, they are plagued by background issues. Any fluorescent labels that have not been cleaved and efficiently washed away from the flow cells in which reactions and fluorescent scanning occur, can interfere with the ability to obtain clear readings in subsequent sequencing cycles.

Recognizing this limitation of fluorescence measurements and appreciating that the $N_3$ group produces a strong Raman signal at ~2100 $cm^{-1}$ where DNA and protein have no Raman peaks, use of the non-fluorescently labeled 3'-O-azidomethyl nucleotides for DNA sequencing with Raman detection is tested. The azido linkage is easily and completely cleaved by incubation with Tris-(2-carboxyethyl) phosphine (TCEP) under aqueous conditions (FIG. 3), leaving DNA intact. In addition, the cleavage reaction completely destroys the $N_3$ group, leading to no background Raman signal. After this cleavage, the 3'-OH group is restored, and there is no chemical remnant of the blocking group; this is important as accumulation of even small modifications on each nucleotide can affect the curvature and other structural properties of the growing DNA chain, potentially interfering with subsequent nucleotide incorporation, leading to earlier termination and shorter sequence reads than would otherwise be obtained.

(a) Generation of 3'-O-azidomethyl-dNTPs:

The protocol for synthesis of these NRTs has previously been described in detail.[15] In brief, the 5'-position and active amino groups on the nucleoside bases are protected, and the 3'-OH group is methylthiomethylated, reacted with sulfuryl chloride, and then with sodium azide to generate the 3'-O-azidomethyl group.

(b) Solution Raman Scattering Measurement:

Initially, the 3'-O-azidomethyl nucleotides (3'-$N_3$-NRTs) are tested, characterized by MS and NMR for quality assurance, in solution. Sufficient concentrations are used to obtain detailed spectra with azido-dependent Raman shifts in the expected range (~2100 cm$^{-1}$) for each of the four nucleotides. For comparison, standard dNTPs or ddNTPs, lacking this Raman label, are used. Having established these conditions, single-base extension reactions are performed as well as 2-4 cycle SBS reactions with solution-based Raman detection using synthetic templates and primers. The dsDNA extended with these NRTs generates the expected Raman signal, which is eliminated upon cleavage with TCEP under aqueous conditions, and re-established with each round of SBS. Templates comprising each of the complementary bases and repeated bases are used to determine both SBS specificity and complete termination of the reaction by the NRTs. Washed aliquots taken after each step of the SBS reactions are collected, concentrated, and subjected to Raman detection.

(c) Surface-Enhanced Raman Scattering (SERS) Measurement:

Various methods of surface enhanced Raman scattering can increase signals by up to 14 orders of magnitude.[29-32] Nucleotides are captured on alumina nanotube porous surfaces containing aggregated metal nanoparticles (Au or Ag) to enhance the signals and measured by Raman spectrometry following literature procedures (29-31). All four molecules should display a strong band at 2100 cm$^{-1}$. In contrast, dNTPs used as controls have no signal at this wavenumber.

(d) Solution-Based SBS with SERS Detection:

After testing the nucleotides themselves, single-base extension reactions are conducted in solution, allowing specific incorporation of each of the four nucleotides, after which the extended DNA chains are adsorbed to the alumina-Ag or alumina-Au surfaces under non-denaturing conditions for SERS recording. In the same way, NRT-extended molecules treated with TCEP are adsorbed to the surfaces and SERS measured. This is similar in principle to the solution-based assays for nucleotides using MALDI-TOF MS.

Figure 11:
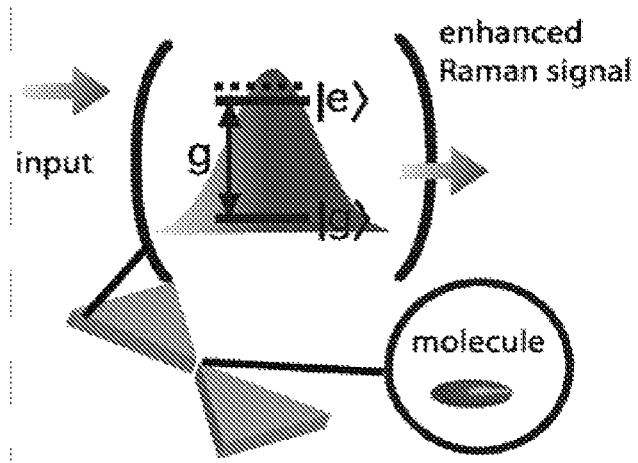
FIG. 11. a) Concept for nanoantennae-enhanced SERS: the plasmonic cavity increases the optical field excitation by more than 100 times, while enhancing the scattering rate by nearly an order of magnitude. b) SEM of sub-10 nm gap made by e-beam lithography.
Figure 11:
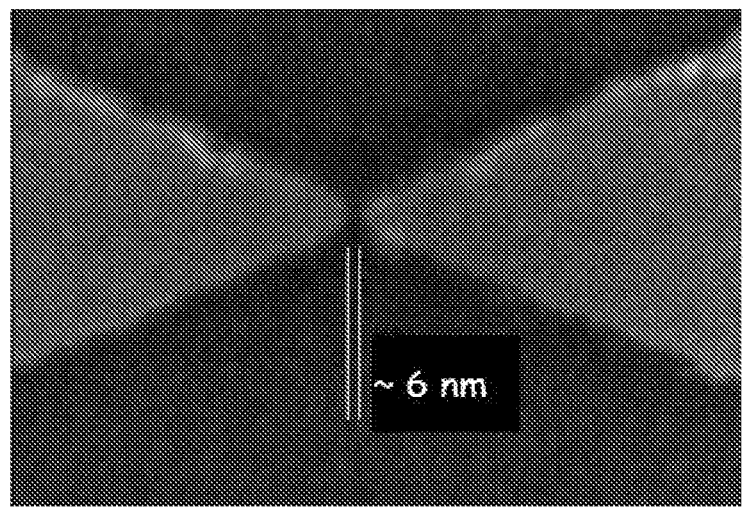

Producing SERS-Prepared Surfaces Designed Specifically for Detection of the Labeled Nucleotides (a) Nanoplasmonic Antenna Arrays for SERS-SBS In recent years, there have been several reports of significant Raman signal enhancement at the single molecule level due to plasmonic coupling to nearby nanostructures (33-35, 38-41). The work was done using roughened surfaces, metal films or discontinuous metal islands deposited on surfaces, colloidal powders, aqueous sols, and beads or scaffolds decorated with noble-metal colloids. These approaches had limited control over the nanostructure geometry and no control over the location of the analyte molecule relative to the plasmonic hot spots. More recent approaches have produced regularly ordered periodic particle arrays for generating promising SERS sensors. Li et al. used nanoimprint lithography (NIL) to form arrays of vertical posts which were coated with Au. The posts were coated with Au, and nanogaps formed on the sidewalls of the posts where traces of Au served as hot spots (42). They achieved impressively high area-average SERS enhancement of 1.2× 10$^9$ and good large-area uniformity; this approach can be even more powerful if one could control the formation of the metallic nanoislands on the sidewalls of the posts. A more controlled approach to localized plasmonic enhancement uses bowtie nano-antennae (43-45). Nanoantennae can enhance room-temperature fluorescence emission from a single molecule >1000 times more than molecules not coupled to the bowtie. This enhancement is the result of a roughly two-orders of magnitude concentration of the incident excitation field inside a ~20 nm$^3$ gap, together with an enhancement of the molecule's quantum yield by nearly an order of magnitude due to the Purcell effect. The Purcell effect results from an increased Rabi frequency, g, between the emitter and the bowtie optical mode, as shown in FIG. 11. This coupled bowtie nanoantenna-molecule system forms an efficient interface between far-field optics and molecular excited state and plasmonic excitations.

Described herein is a robust, solid-state platform for measuring the SERS signal resulting from the polymerase extension of specific oligonucleotides in SBS reactions. The platform integrates nanoplasmonic bowtie antennae together with site specific biomolecular interactions to yield reproducible and optimal signal enhancement. We combine plasmonic modeling, advanced nanofabrication, selective biochemical surface functionalization and photophysical analysis to design, build and measure arrays of nanoplasmonic antennae incorporating DNA functionalized sites. Initially, focus is on optimizing the SERS signal from few-molecule assemblies, to obtain robust, reproducible signals with minimum scatter. Next, to reduce background from the pump laser by using a new type of crossed-bowtie structure in which one pair of triangles couples to the incident field, while the other pair couples to the Raman scattered field in an orthogonal polarization. This cross-polarized design could enable SERS without the need for a high-resolution spectrometer or other spectral filters.

(b) Plasmonic Nanoantennae Design

Figure 12:
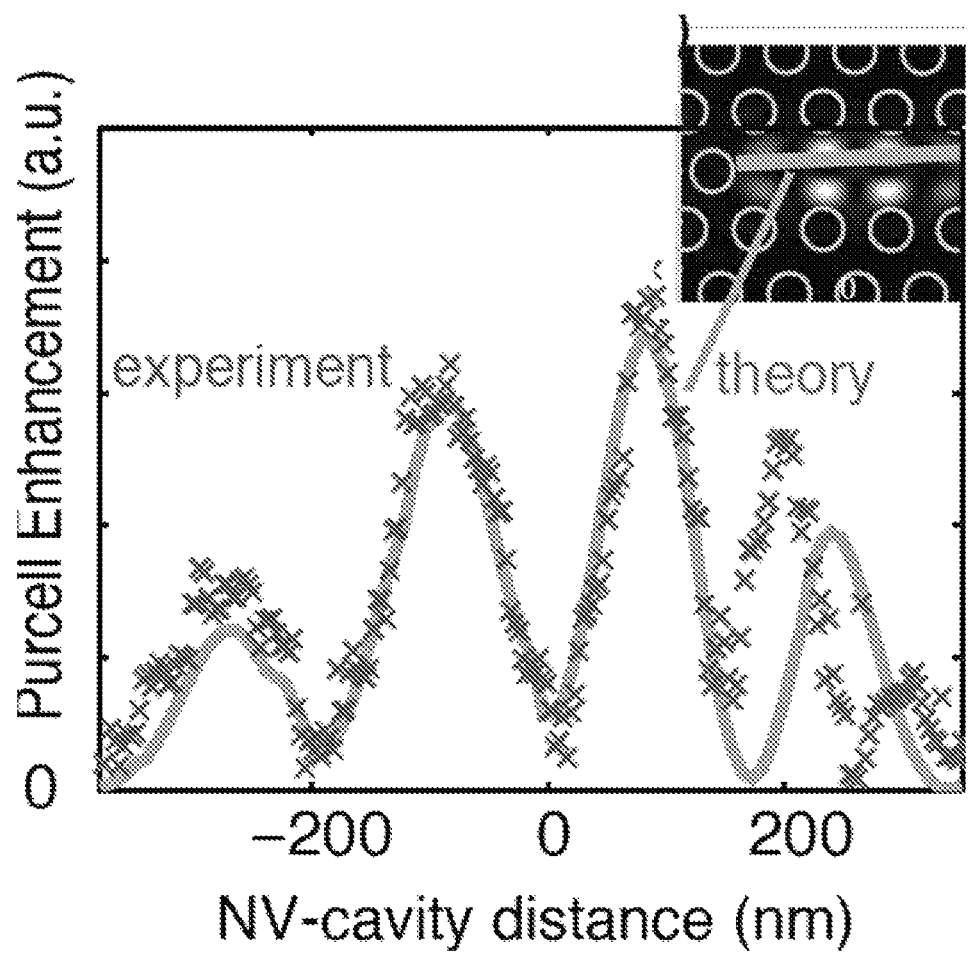
FIG. 12. Spatially resolved coupling between a single nitrogen vacancy color center and an optical mode of a planar photonic crystal nanocavity, showing the spatially resolved Purcell effect in a solid.

To determine the optimal nanoantenna design, a variety of issues has to be addressed: the molecule is deterministically positioned, using a nanopositioning stage, to understand the position dependence of surface-enhanced Raman scattering near the bowtie gap. In similar recent experiments with dielectric cavities, a single emitter was used to trace out the spatially resolved Purcell enhancement with 3-nm precision (46), as shown in FIG. 12. To maximize the Raman signal, bowtie resonator designs are optimized with resonances in the red, corresponding to the NRTs.

(c) Nanofabrication and Surface Functionalization

Figure 13:
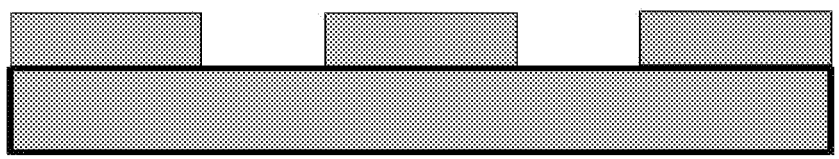
FIG. 13. Process for forming bowtie antenna structures with selective placement of DNA within the gap. a) E-beam lithography and development. b) Deposition of spacer, Ag and Ti, followed by liftoff. c) SiO₂ deposition by CVD, followed by HMDS. d) Second lithography to define adhesion sites for DNA primer. e) Primer assembly.
Figure 13:
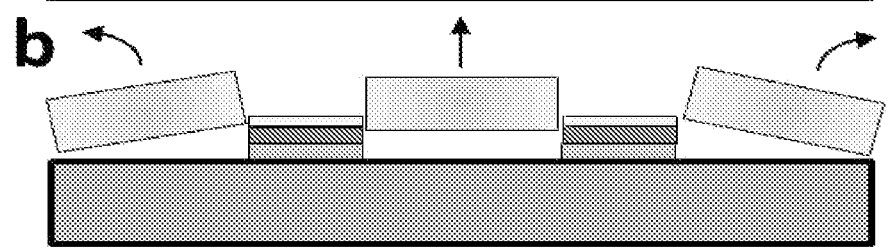
Figure 13:
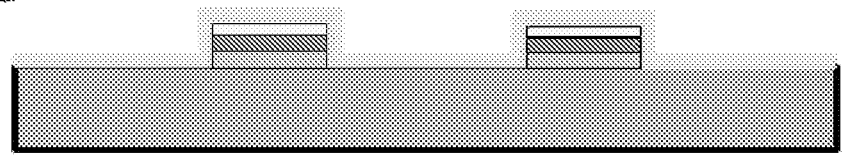
Figure 13:
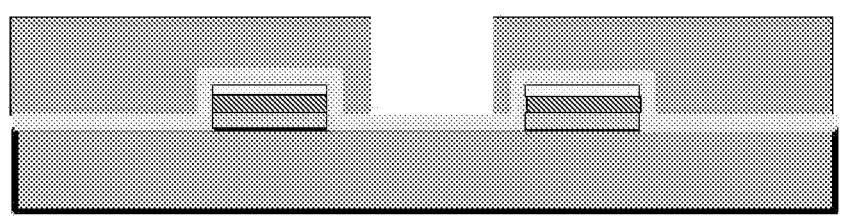
Figure 13:
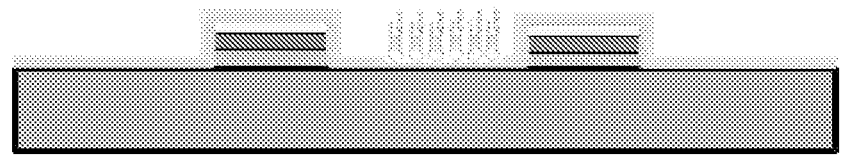

By combining advanced nanofabrication with selective biomolecular surface functionalization, one could create functional surfaces with control to the single-molecule level (47-53). Here, arrays of bowtie nanoantennae with gap sizes ranging from ~50 nm to 8 nm are fabricated. The surface is selectively functionalized within the gap to control primer concentration and thus the number of SBS reactions within each gap, as shown in FIG. 11a. The antenna structures are patterned by electron beam lithography at 80-100 keV. In addition, resist processes allow one to reproducibly achieve sub-10 nm resolution (FIG. 11b). The processes rely on low temperature ultrasonic development and rinse of low molecular weight PMMA, which prevents swelling and promotes high contrast (54, 55). Ag or Al are deposited with a thin protective Ti cap by electron beam evaporation. The bowties may be raised off the substrate surface by etching slightly into the substrate or depositing a thin (few nm) spacer prior to metal deposition. After liftoff, the structures are passivated with a thin CVD oxide layer, followed by deposition of HMDS (hexamethyl-disilazane, which repels DNA). A second lithography step defines primer adhesion sites, with PMMA once again as a resist. Following development, an $O_2$ reactive ion etch removes HMDS in the patterned regions, exposing the oxide, rendering it hydrophilic, allowing the primer to adsorb only in the exposed area, thereby control the concentration and number of molecules within the gap. The process is shown in FIG. 13.

Figure 14:
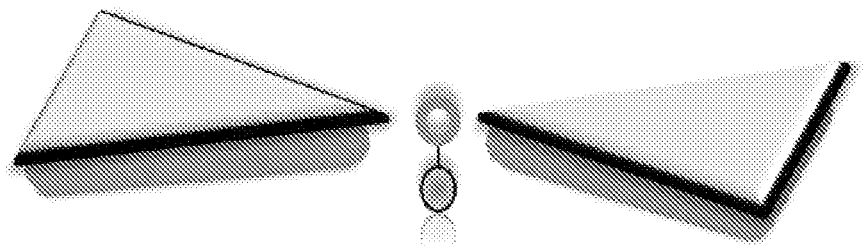
FIG. 14. Bowtie antenna with DNA polymerase bound to a patterned nanodot centered in the hotspot.

This design may be subject to the "moving target" problem, the situation where the Raman active NRTs extend beyond the optimal enhancement field as the hybridizing strand elongates. As one does not know a priori how severe this problem is in practice, one can monitor the SERS signal as a function of strand length. If the signal decays significantly, to modify the surface functionalization to immobilize polymerase molecules within the bowtie gap using a process developed for controlling the placement of individual peptides and proteins on nanolithographically patterned nanodots with dimensions as small as 4 nm or less (50, 56). A single nanodot (or nanodot cluster) is lithographically patterned within the bowtie gap. DNA polymerase is bound to the nanodot, as shown in FIG. 14, using an amine-based linkage. This fixes the hybridization site to within the optimal enhancement zone of the bowtie antenna, independent of the length of the DNA.

Figure 15:
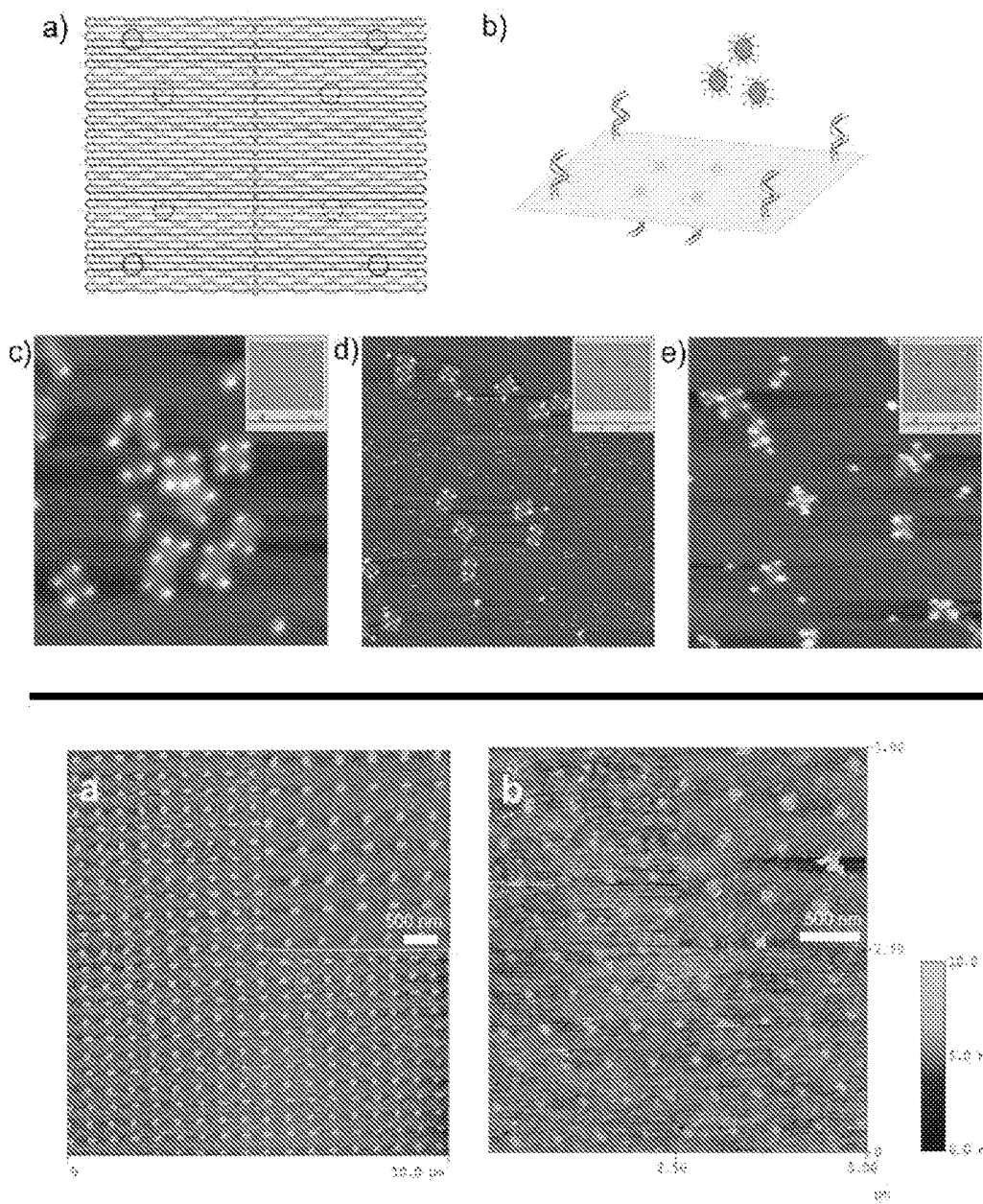
FIG. 15. Top: Au nanoparticle binding to DNA origami. Many different configurations are possible. Bottom: Lithographically directed placement of origami scaffolds (left: rectangles; right: triangles).

Another technique to reliably place a single primer molecule within a plasmonic hot spot with reliable control over all dimensions may be used to achieve single-molecule probing. This technique relies on the use of DNA origami (57). We have recently developed processes to place 5 nm Au nanoparticles at prescribed locations on origami scaffolds (FIG. 15a) by integrating sticky end binding strands into programmed staple locations within the origami framework to which nanoobjects functionalized with complementary sticky ends can bind. This can place objects as close as 2 nm apart (58), and to place origami scaffolds at lithographically determined locations on a substrate using nanoimprint lithography (59), as shown in FIG. 15b. Thus, construct arrays of origami scaffolds upon which Au and Ag nanoparticles and nanorods are placed at specified binding sites a few nanometers apart and position a primer molecule between them is possible. This platform could provide a reliable measure of SERS enhancement at the single molecule level.

Figure 16:
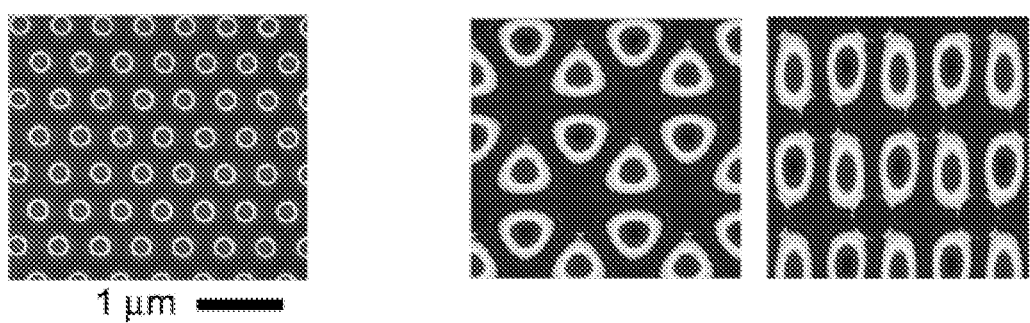
FIG. 16. Left: Plasmonic crystal consisting of a patterned TiO—Au—TiO layer on InP. Right: Resonant plasmonic mode for coupling to molecules on the metal surface.

Use of "plasmonic crystals", arrayed plasmonic structures that are coupled to show band formation, is contemplated, by employ periodic TiO—Au—TiO structures (FIG. 16) for enhanced light generation and extraction from InP-based quantum wells (60). The emission rate enhancement of molecules coupled to such structures could reach a factor of 50, more than what may be possible with bowtie antennae.

Experiments on spatially resolved plasmon-molecule coupling are conducted using scanning confocal microscopy setups. Using a set of tunable continuous-wave and picosecond pulsed lasers, operating in the range of 405-900 nm, one is able to optimally excite the plasmonic structure, while positioning the molecule with nm resolution. These experiments enable one to understand the physics governing the coupling between single emitters and localized and periodic plasmonic field concentrators, providing the fundamental knowledge needed to develop more efficient plasmon-enhanced SERS devices. By applying techniques from solid state cavity quantum electrodynamics (QED) to plasmonic nano-cavities (61-63) to efficiently pump and collect from single molecules coupled to the bowtie structures, a new range of quantum optical interfaces for interacting with single molecules in a controllable fashion can be developed.

Conducting Surface-Bound SBS Reactions with SERS Detection

Figure 17:
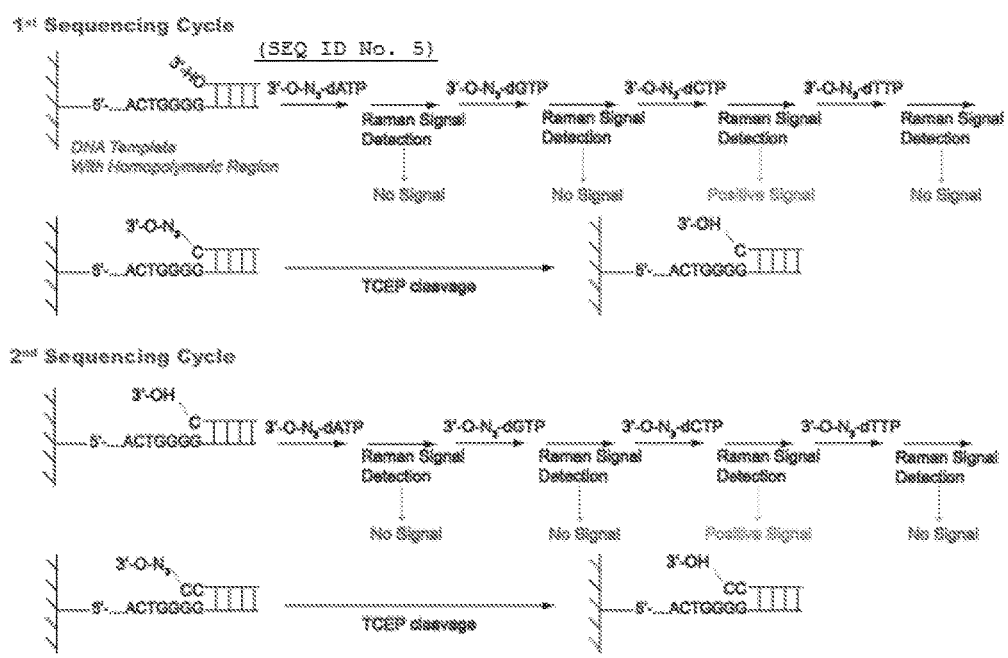
FIG. 17. An overall scheme for SERS-SBS with 3'-O-azidomethyl dNTPs. Surface-attached templates are extended with NRTs, added one at a time. If there is incorporation, a Raman signal (~2105 cm⁻¹) due to the N₃ group is detected. After cleavage of the blocking group with TCEP, the next cycle is initiated. Because the NRTs force the reactions to pause after each cycle, the lengths of homopolymers are determined with precision.

Synthetic templates and PCR products are covalently attached to SERS-prepared surfaces, and hybridized with primers. Single-base extension reactions are conducted with each of the four 3'-O—$N_3$-NRTs, adding them one by one. The overall scheme is shown in FIG. 17. In this way, the incorporation specificity is measured by virtue of the Raman signal. After cleavage and re-recording of the Raman spectrum, a second and third cycle of SBS is conducted. Templates are designed to include 2 of each base in a row, as a way of confirming that the NRTs are completely terminating the reactions. Lagging reactions due to incomplete removal of the azidomethyl groups are observed for.

There are several possibilities for attaching DNA to SERS surfaces. In a non-limiting example, the DNA is covalently linked to a carboxy-modified silica slide using an NHS ester, after which the alumina and gold coating is administered to the slide. Other chemistries are also possible, beginning with $NH_2$ or biotinylated surfaces. Depending on how much of the surface is coated, the opposite order of addition (SERS coating first, DNA attachment second) can be utilized. An alternative approach is to attach the DNA directly to silver nanoparticles (32).

A major advantage of the SERS-SBS approach is its high sensitivity and simplicity. The dilution of samples to the limit of adequate and consistent signal capture permits evaluation of the method. This permits direct mRNA sequencing, avoiding the biases inherent in cDNA synthesis and amplification in digital transcriptome analysis (RNA-Seq).

A strong Raman signal is obtained with SERS for individual NRTs, NRTs that are part of DNA chains, and in surface-bound SBS reactions with these NRTs. Of course, because the same band is obtained for each of these molecules, it is necessary to add the nucleotides one by one.

Figure 18:
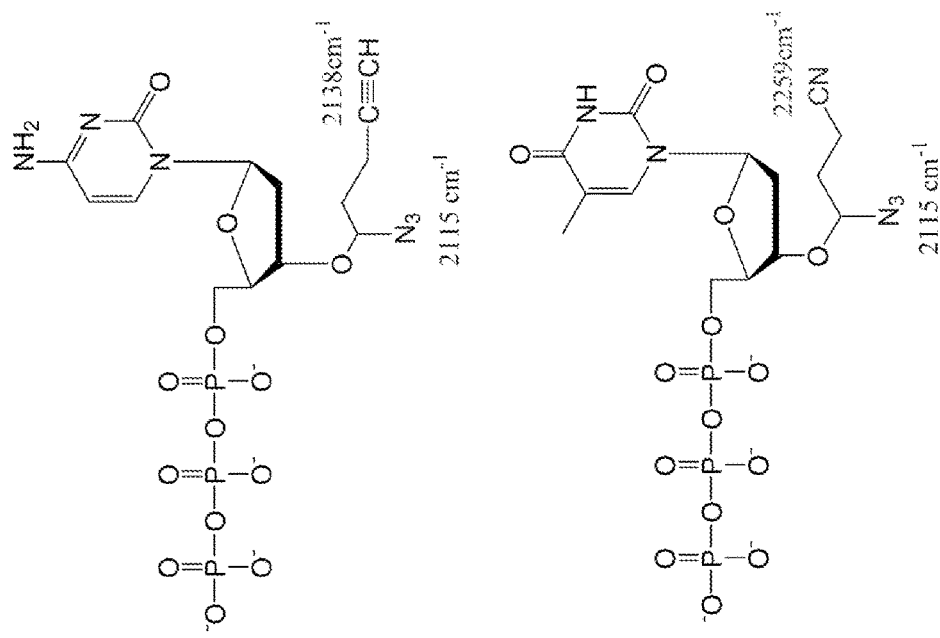
FIG. 18. Four modified nucleotide reversible terminators with distinct 3'-O-Raman tags for use in the design and synthesis of novel NRTs with 4 distinct SERS signatures to perform SERS-SBS. Their Raman peaks are also indicated.
Figure 18:
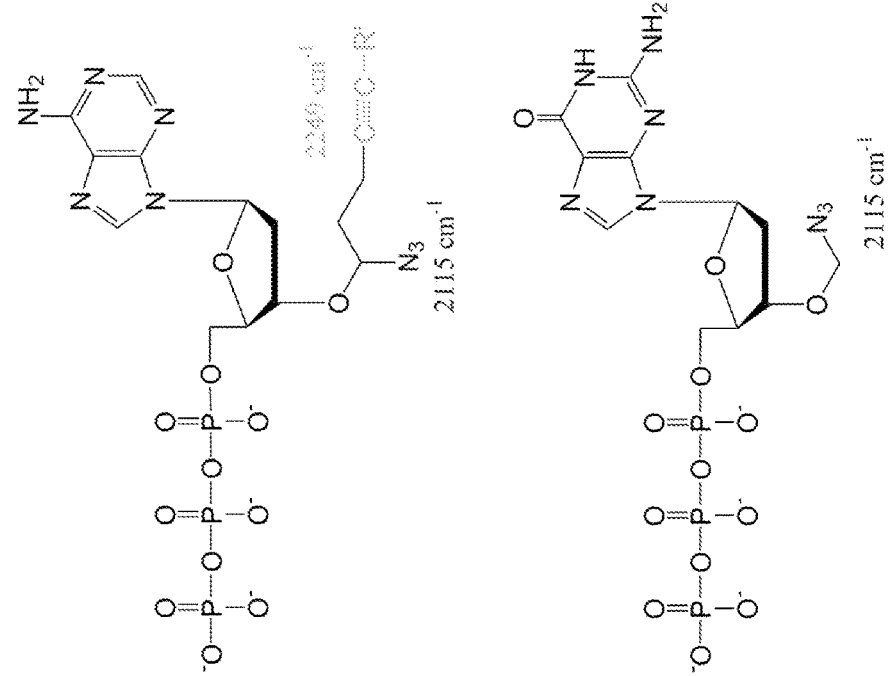
Figure 19:
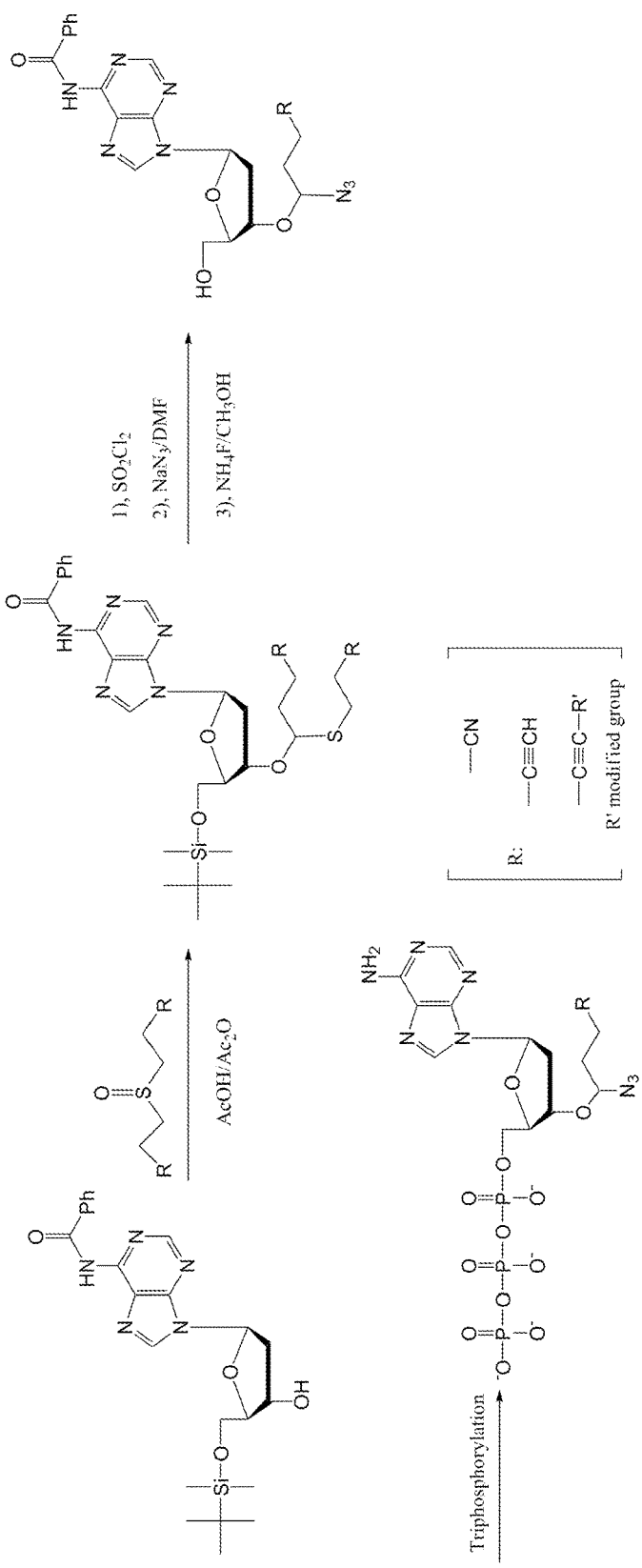
FIG. 19. Generalized synthetic scheme for NRTs shown in FIG. 7. This is a straightforward modification of the protocol used to produce the 3'-O-azidomethyl-NRTs for use in SBS in solution with Raman and SERS detection. In brief, 5'-protected 2'-deoxynucleosides are treated with disubstituted ethyl sulfoxide and acetic anhydride/acetic acid to produce, via a Pummerer rearrangement, intermediates that then react with sulfuryl chloride and sodium azide to afford 3'-azidomodified nucleoside derivatives.
Figure 20:
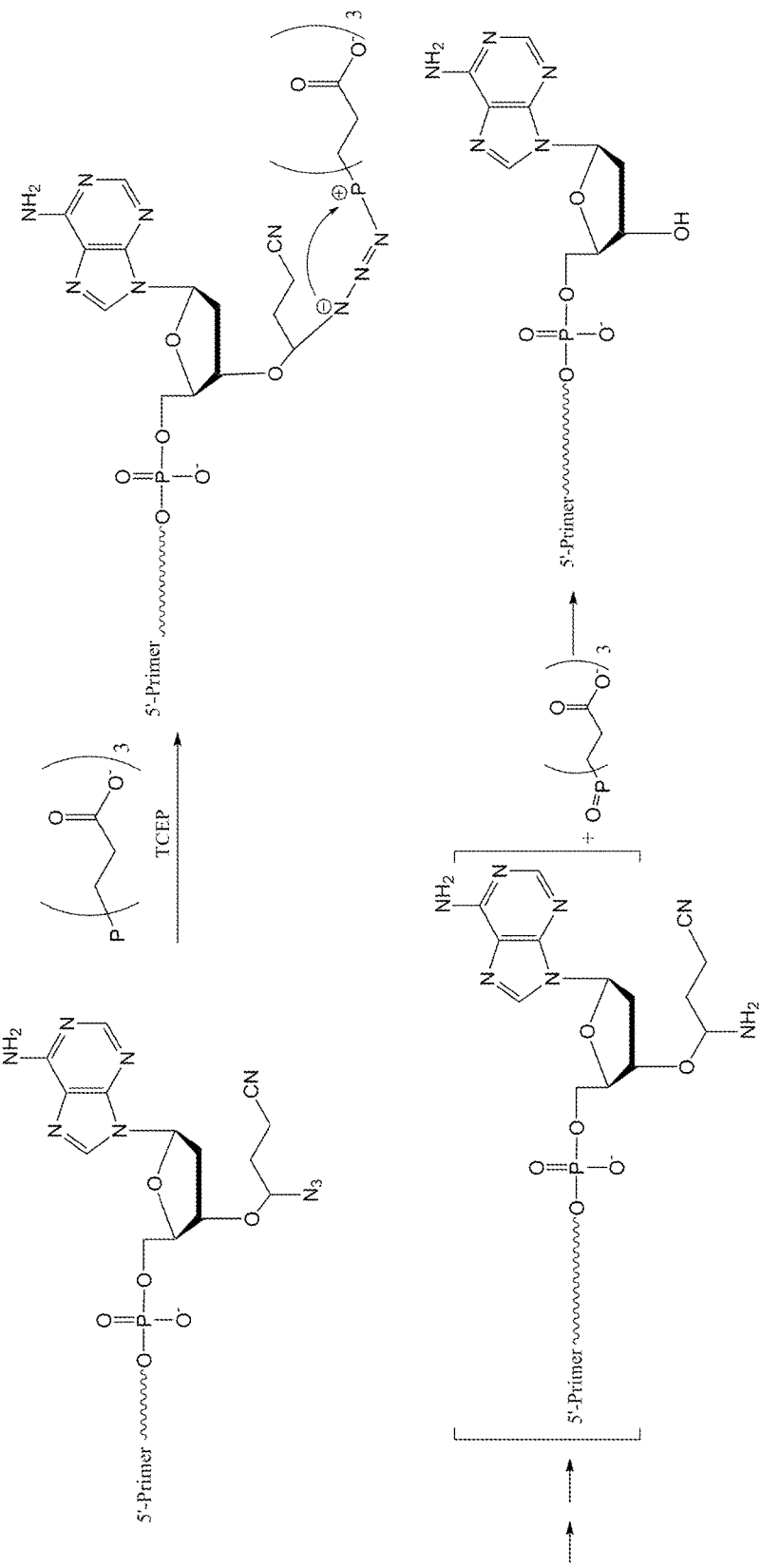
FIG. 20. Mechanism of cleavage of the 3' group of an incorporated nucleotide analogue (adenine base) as depicted in FIG. 7. A similar scheme operates for all the Raman tags attached to the 3'-OH group. Note the reversion to the 3'-OH and destruction of the N₃ group.
Figure 21:
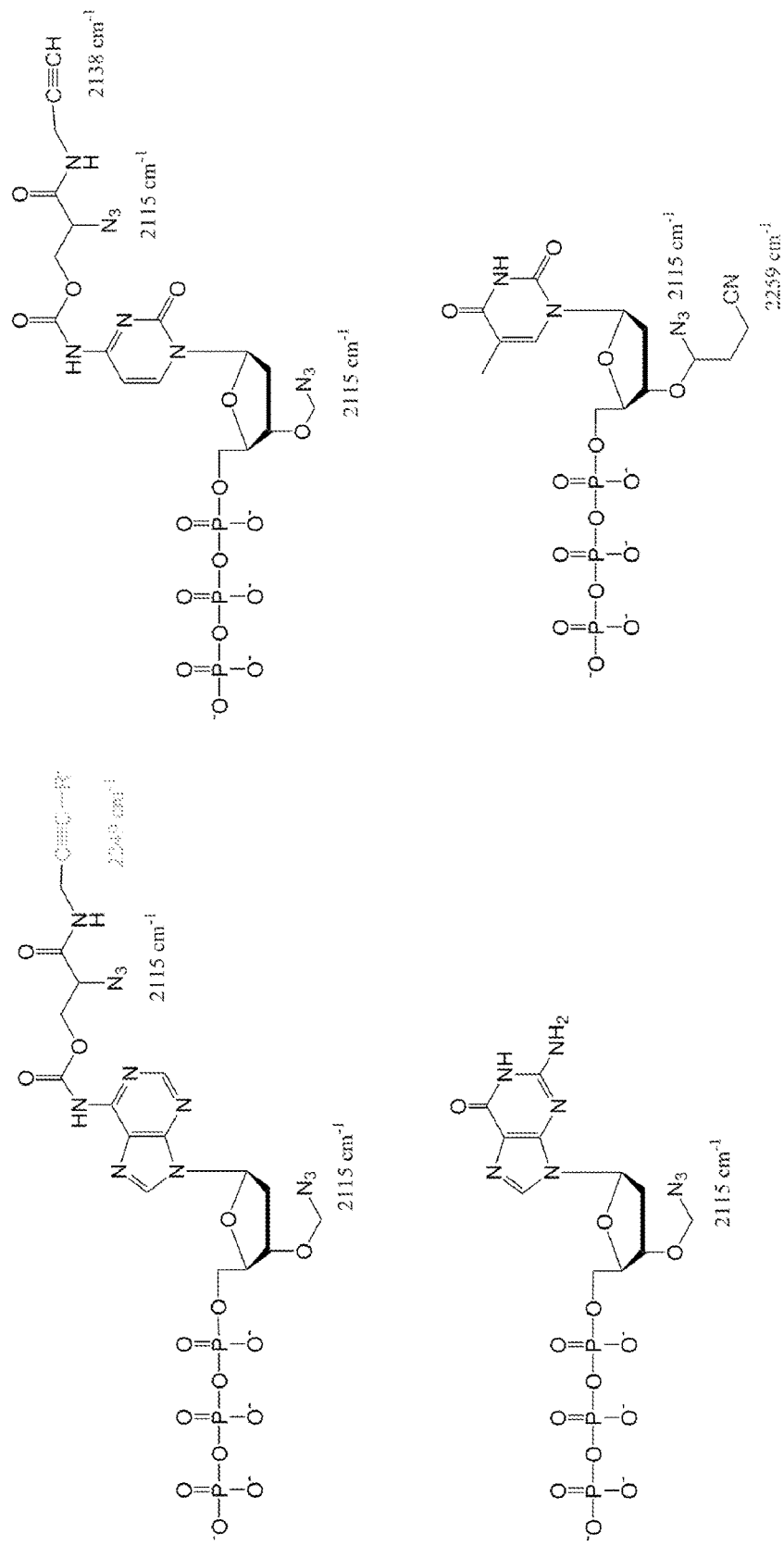
FIG. 21. Alternative NRTs with distinct Raman tags placed either on the base via NH₂ groups on A and C, or at the 3'-OH of the sugar for G and T. In the case of the A and C analogs at the top of the figure, treatment with TCEP removes both the substitution on the base and at the 3'-OH position at the same time, resulting in restoration of intact dATP and dCTP.
Figure 22:
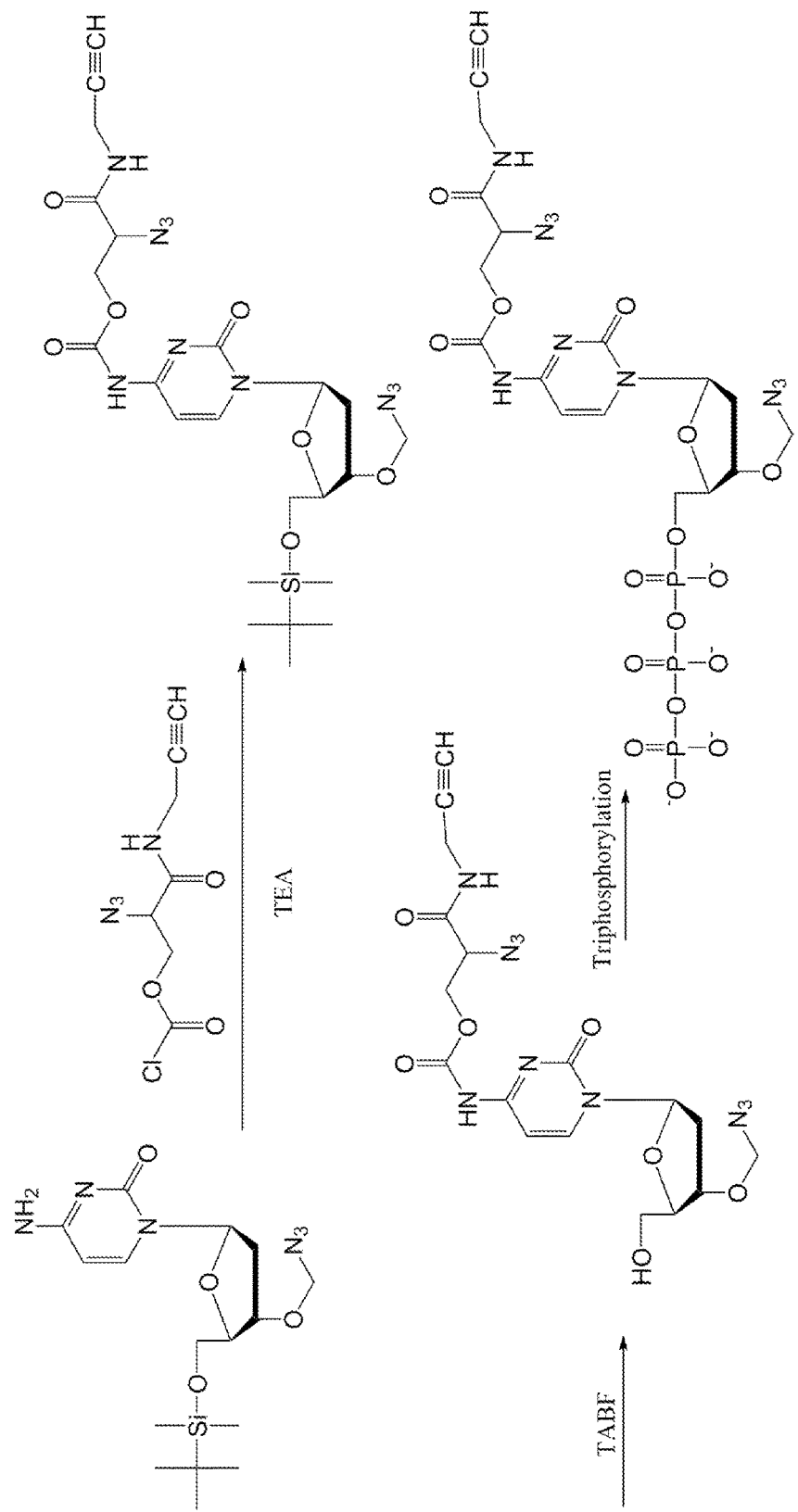
FIG. 22. Synthetic scheme for generation of the C analog substituted via the amino group on the base with a tag displaying two Raman peaks due to the presence of both an N₃ and alkyne group.

Design and Synthesis of Novel NRTs with 4 Distinct SERS Signatures to Perform SERS-SBS To overcome the major limitation of the approach described above, i.e. the need to add each of the NRTs, one by one, due to their each producing an identical Raman peak, three additional nucleotides are synthesized with distinct Raman signatures; thus providing a set of four unique Raman tags, one for each of the four bases of DNA. There are two options. First, in the simplest and most elegant design, the molecules are generated by attaching chemical groups with distinct SERS signatures directly to the 3'-OH group. In this way, they serve at the same time as reversible termination groups and Raman tags. The NRTs in this category are depicted in FIG. 18, and a simplified synthetic scheme for generating such compounds is presented in FIG. 19. Each contains the azido peak at ~2100 $cm^{-1}$, but in addition they display bands at 2150-2250 depending on the additional groups included (cyano, alkyne, etc.). Most 3'-OH modifications in this size range are well accepted by the mutant polymerases used for SBS with 3'-$N_3$-NRTs. Efficient cleavage of the blocking groups and their associated tags is accomplished with aqueous TCEP. The cleavage mechanism destroys the $N_3$ group and restores the 3'-OH, as shown in FIG. 20. Second, the new Raman signaling groups can be attached to the base via an azidomethyl or other cleavable group that does not leave a chemical modification after cleavage. In this variation, it is preferred to have a separate reversible blocking group on the 3'-OH. If necessary, a combination of both approaches can be utilized to achieve the desired set of four distinct Raman signatures as illustrated in FIG. 21. A synthetic scheme for the modified cytosine shown at the upper right in FIG. 21 is presented in FIG. 22. All molecules are characterized during and after synthesis by standard approaches (MS, NMR, IR, SERS, etc.) to assess purity and product yield.

Figure 23:
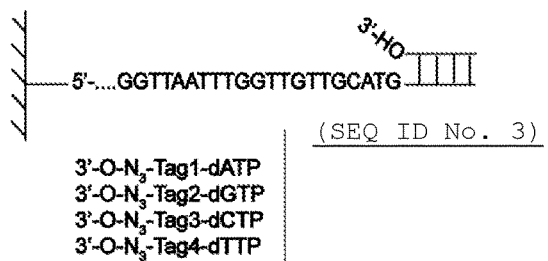
FIG. 23. Overall design of SERS-SBS for 4 mixed nucleotides with four different Raman signatures. A specific NRT complementary to the next base in the covalently attached template added by polymerase to the hybridized primer is decoded via its Raman signature. After cleavage of the 3'-O-tag by TCEP, the next cycle can ensue. Note that all 4 NRTs have an azido peak, but in addition 3 of the NRTs have a second discriminating peak. The Raman signatures are shown in FIG. 5.
Figure 23:
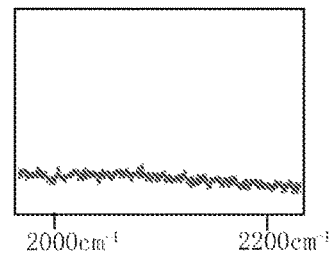
Figure 23:
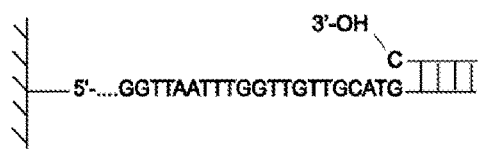
Figure 23:
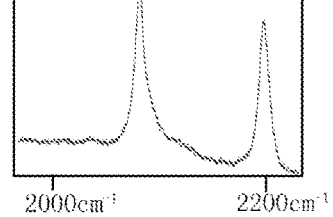
Figure 23:
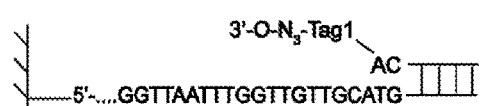
Figure 23:
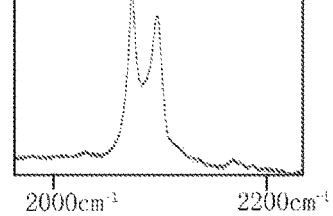

SBE reactions and cleavage in solution are conducted, and aliquots of the reaction mixture are adsorbed after incorporation and after cleavage to SERS-prepared surfaces for recording Raman spectra in the same way as described above. However, in this case, all four NRTs can be added at the same time, as indicated in FIG. 23, since the unique signature of each indicates the appropriate incorporation. Covalent attachment of synthetic templates to SERS-prepared surfaces, and hybridization of primers permits single-base extension reactions, with all four 3'-O—N$_3$-NRTs. After cleavage and re-recording of the Raman spectrum, a second and third cycle of SBS is performed. Templates include 2 of each base in a row, as a way of confirming that the NRTs are completely terminating the reactions. Extensive cycles of SBS can be performed with SERS detection. DNA sample dilution is performed to quantify ultra-high sensitivity detection limits. Subsequently, bridge PCR is used to amplify a known DNA template on the SERS surface disclosed herein and the 4-color Raman NRTs to test the read length and performance of the SERS-SBS system. The successful completion of this process lays a solid foundation for the development of a routine SERS-SBS system.

Real-World Next-Generation Sequencing Libraries Used to Compare SERS-SBS

Whole-genome sequencing can be obtained by first obtaining long sequencing reads on synthetic templates, and then sequencing a small library (e.g., a BAC shotgun library or a shotgun library derived from a bacterial genome). DNA placed at several thousand positions per slide is sufficient. In an embodiment, a thick layer with drilled wells can be used that can incorporate either DNA-attached beads, or wherein DNA is directly spotted, attached and amplified as necessary. These "masks" are attached to the surface of alumina nanotube-coated slides to which gold or silver particles are applied. In the simplest approach that avoids issues of DNA attachment to the alumina-coated slides themselves, single molecules of DNA are amplified on beads by emulsion PCR and individual beads are inserted into the drilled wells. The flow cell permits adequate wash-through of reagents while not allowing the beads to escape. SBS is carried out under conditions established above. Methods of attachment of DNA have been indicated above also.

REFERENCES

1. Hawkins, R. D., Hon, G. C., Ren, B. (2010) Next-generation genomics: an integrative approach. *Nat. Rev. Genet.* 11:476-486.
2. Morozova, O., Hirst, M., Marra, M. A. (2009) Applications of new sequencing technologies for transcriptome analysis. *Annu Rev Genomics Hum Genet* 10:135-51.
3. Park, P. J. (2009) ChIP-seq: advantages and challenges of a maturing technology. *Nat Rev Genet* 10:669-680.
4. Fuller, C. W., Middendorf, L. R., Benner, S. A., Church, G. M., Harris, T., Huang, X., Jovanovich, S. B., Nelson, J. R., Schloss, J. A., Schwartz, D. C., Vezenov, D. V. (2009) The challenges of sequencing by synthesis. *Nat Biotechnol* 27:1013-1023.
5. Harris, T. D., Buzby, P. R., Babcock, H., et al. (2008) Single-molecule DNA sequencing of a viral genome. *Science,* 320:106-109.
6. Eid, J., Fehr, A., Gray, J., et al. (2008) Real-time DNA sequencing from single polymerase molecule. *Science* 323:133-138.
7. http://www.lifetechnologies.com/news-gallery/press-releases/2010/life-technologies-unveils-single-molecule-sequencing-technology.html
8. Ronaghi, M., Uhlen, M. and Nyren P. (1998) A sequencing method based on real-time pyrophosphate. *Science,* 281:364-365.
9. Ronaghi, M. (2001) Pyrosequencing sheds light on DNA sequencing. *Genome Res.,* 11:3-11.
10. Ju, J., Li, Z., Edwards, J., Itagaki, Y. (2003) Massive parallel method for decoding DNA and RNA. U.S. Pat. No. 6,664,079.
11. Chen, F., Gaucher, E. A., Leal, N. A., Hutter, D., Havemann, S. A., Govindarajan, S., Ortlund, E. A., Benner, S. A. (2010) Reconstructed evolutionary adaptive paths give polymerases accepting reversible terminators for sequencing and SNP detection. *Proc. Natl. Acad. Sci. U.S.A.,* 107:1948-53.
12. Turcatti, G., Romieu, A., Fedurco, M., Tairi, A-P. (2008) A new class of cleavable fluorescent nucleotides: synthesis and optimization as reversible terminators for DNA sequencing by synthesis. *Nucleic Acids Res.,* 36:e25.
13. Wu, W., Stupi, B. P., Litosh, V. A., Mansouri, D., Farley, D., Morris, S., Metzker, S., Metzker, M. L. (2007) Termination of DNA synthesis by N6-alkylated, not 3'-O-alkylated, photocleavable 2'-deoxyadenosine triphosphates. *Nucleic Acids Res.,* 35:6339-49.
14. Ju, J., Kim, D. H., Bi, L., Meng, Q., Bai, X., Li, Z., Li, X., Marma, M. S., Shi, S., Wu, J., Edwards, J. R., Romu, A., Turro, N. J. (2006) Four-color DNA sequencing by synthesis using cleavable fluorescent nucleotide reversible terminators. *Proc Natl Acad Sci USA* 103:19635-19640.
15. Guo, J., Xu, N., Li, Z., Zhang, S., Wu, J., Kim, D. H., Marma, M. S., Meng, Q., Cao, H., Li, X., Shi, S., Yu, L., Kalachikov, S., Russo, J. R., Turro, N. J., Ju, J. (2008) Four-color DNA sequencing with 3'-O-modified nucleotide reversible terminators and chemically cleavable fluorescent dideoxynucleotides. *Proc Natl Acad Sci USA* 105:9145-9150.
16. Wu, J., Zhang, S., Meng, Q., Cao, H., Li, Z., Li, X., Shi, S., Kim, D. H., Bi, L., Turro, N. J., Ju, J. (2007) 3'-O-modified Nucleotides as Reversible Terminators for Pyrosequencing. *Proc Natl Acad Sci USA* 104:16462-16467.
17. Nie, S. and Emory, S. R. (1997) Probing Single Molecules and Single Nanoparticles by Surface-Enhanced Raman Scattering. *Science* 275:1102-1106.
18. Ju, J., Cao, H., Li, Z., Meng, Q., Guo, J., Zhang, S. (2009) Design and synthesis of cleavable fluorescent nucleotides as reversible terminators for DNA sequencing by synthesis. International Patent Application, International Publication Number WO 2009/051807 A1.
19. Marti, A. A., Li, X., Jockusch, S., Stevens, N., Li, Z., Raveendra, B., Kalachikov, S., Morozova, I., Russo, J. J., Akins, D. L., Ju, J., Turro, N. J. (2007) Design and characterization of two-dye and three-dye binary fluorescent probes for mRNA detection. *Tetrahedron* 63:3591-3600.

20. Strug, L, J, Clarke, T., Chiang, T., Chien, M., Baskurt, Z., Li, W., Dorfman, R., Bali, B., Wirrell, E., Kugler, S. L., Mandelbaum, D. E., Wolf, S. M., McGoldrick, P., Hardison, H., Novotny, E. J., Ju, J., Greenberg, D. A., Russo, J. J., Pal, D. K. (2009) Centrotemporal sharp wave EEG trait in rolandic epilepsy maps to Elongator Protein Complex 4 (ELP4). Eur J Human Genet 17:1171-1181.

21. Haghighi, F., Back-Mizrachi, H., Huang, Y. Y., Arango, V., Shi, S., Dworak, A. J., Rosoklija, G., Sheng, H. T., Morozova, I., Ju, J., Russo, J. J., Mann, J. J. (2008) Genetic architecture of the human tryptophan hydroxylase 2 gene: existence of neural isoforms and relevance for major depression. Mol Psychiatry. 13:813-820.

22. Landgraf, P., Rusu, M., Sheridan, R., Sewer, A., et al. (2007) A mammalian microRNA expression atlas based on small library RNA sequencing. Cell 129:1401-1414.

23. Li, Z., Bai, X., Ruparel, H., Kim, S., Turro, N. J., Ju, J. (2003) A Photocleavable Fluorescent Nucleotide for DNA Sequencing and Analysis. *Proc Natl Acad Sci USA* 100: 414-419.

24. Ruparel, H., Bi, L., Li, Z., Bai, X., Kim, D. H., Turro, N. J., Ju, J. (2005) Design and Synthesis of a 3'-O-allyl Photocleavable Fluorescent Nucleotide as a Reversible Terminator for DNA Sequencing By Synthesis. *Proc Natl Acad Sci USA* 102:5932-5937.

25. Seo, T. S., Bai, X., Kim, D. H., Meng, Q., Shi, S., Ruparel, H., Li, Z., Turro, N. J., Ju, J. (2005) Four-Color DNA Sequencing by Synthesis on Chip Using Photocleavable Fluorescent Nucleotide Analogues. *Proc Natl Acad Sci USA* 102:5926-5931.

26. Edwards, J. R., Itagaki, Y., Ju, J. (2001) DNA sequencing using biotinylated dideoxynucleotides and mass spectrometry. *Nucleic Acids Res*, 29:E104.

27. Ruparel, H., Ulz, M. E., Kim, S., Ju, J (2004) Digital detection of genetic mutations using SPC-sequencing. *Genome Res.* 14:296-300.

28. Pelletier, H., Sawaya M. R., Kumar, A., Wilson, S. H., Kraut, J. (1994) Structures of ternary complexes of rat DNA polymerase beta, a DNA template-primer, and ddCTP. *Science* 264:1891-1903.

29. Ko, H. and Tsukruk, V. V. (2008) Nanoparticle-decorated nanocanals for serface-enhanced Raman scattering. *Small* 4:1980-1984.

30. Chang, S., Ko, H., Singamaneni, S., Runawidjaja, R., Tsukruk, V. V. (2009) Nanoporous membranes with mixed nanoclusters for Raman-based label-free monitoring of peroxide compounds. *Anal. Chem.* 81:5740-5748.

31. Ko, H., Chang, S., Tsukruk, V. V. (2009) Porous substrates for label-free molecular level detection of nonresonant organic molecules. *Nano* 3:181-188.

32. Tuan, V. (2007) SERS diagnostic platforms, methods and systems microarrays, biosensors and biochips. U.S. Pat. No. 7,267,948.

33. Etchegoin, P. G., Le Ru, E. C. & Meyer, M. Evidence of natural isotopic distribution from single-molecule SERS. *J Am Chem Soc* 131, 2713-6 (2009).

34. Kleinman, S. L. et al. Single-Molecule Surface-Enhanced Raman Spectroscopy of Crystal Violet Isotopologues: Theory and Experiment. *Journal of the American Chemical Society* 133, 4115-4122 (2011).

35. Hsiao, W.-H. et al. Surface-Enhanced Raman Scattering Imaging of a Single Molecule on Urchin-like Silver Nanowires. *ACS Applied Materials & Interfaces* 3, 3280-3284 (2011).

36. Savitzky, A.; Golay, M. J. E. *Anal. Chem.* 1964, 36, 1627.

37. Zhang, D.; Ben-Amotz, D. *Appl. Spectrosc.* 2000, 54, 1379.

38. Bell, S. E. J. & Sirimuthu, N. M. S. Surface-enhanced Raman spectroscopy (SERS) for sub-micromolar detection of DNA/RNA mononucleotides. *Journal of the American Chemical Society* 128, 15580-15581 (2006).

39. Blackie, E. J., Le Ru, E. C. & Etchegoin, P. G. Single-Molecule Surface-Enhanced Raman Spectroscopy of Nonresonant Molecules. *Journal of the American Chemical Society* 131, 14466-14472 (2009).

40. Michaels, A. M., Nirmal, M. & Brus, L. E. Surface enhanced Raman spectroscopy of individual rhodamine 6G molecules on large Ag nanocrystals. *Journal of the American Chemical Society* 121, 9932-9939 (1999).

41. Yoon, I. et al. Single Nanowire on a Film as an Efficient SERS-Active Platform. *Journal of the American Chemical Society* 131, 758-762 (2009).

42. Li, W. D., Ding, F., Hu, J. & Chou, S. Y. Three-dimensional cavity nanoantenna coupled plasmonic nanodots for ultrahigh and uniform surface-enhanced Raman scattering over large area. *Optics Express* 19, 3925-3936 (2011).

43. Fromm, D. P. Exploring the chemical enhancement for surface-enhanced Raman scattering with Au bowtie nanoantennas. *J. Chem. Phys.* 124, 061101 (2006).

44. Hatab, N. A. et al. Free-Standing Optical Gold Bowtie Nanoantenna with Variable Gap Size for Enhanced Raman Spectroscopy. *Nano Letters* 10, 4952-4955 (2010).

45. Kinkhabwala, A. et al. Large single-molecule fluorescence enhancements produced by a bowtie nanoantenna. *Nature Photonics* 3, 654-657 (2009).

46. Englund, D. et al. Deterministic Coupling of a Single Nitrogen Vacancy Center to a Photonic Crystal Cavity. *Nano Letters* 10, 3922-3926 (2010).

47. De Poortere, E. P. et al. 1-to 2-nm-wide nanogaps fabricated with single-walled carbon nanotube shadow masks. *Journal of Vacuum Science & Technology B* 24, 3213-3216 (2006).

48. Guo, X. F. et al. Covalently bridging gaps in single-walled carbon nanotubes with conducting molecules. *Science* 311, 356-359 (2006).

49. Palma, M. et al. Selective Biomolecular Nanoarrays for Parallel Single-Molecule Investigations. *Journal of the American Chemical Society* 133, 7656-7659 (2011).

50. Schvartzman, M. et al. Nanolithographic Control of the Spatial Organization of Cellular Adhesion Receptors at the Single-Molecule Level. *Nano Letters* 11, 1306-1312 (2011).

51. Tang, J., De Poortere, E. P., Klare, J. E., Nuckolls, C. & Wind, S. J. Single-molecule transistor fabrication by self-aligned lithography and in situ molecular assembly. *Microelectronic Engineering* 83, 1706-1709 (2006).

52. Tang, J., Wang, Y., Nuckolls, C. & Wind, S. J. Chemically responsive molecular transistors fabricated by self-aligned lithography and chemical self-assembly. *Journal of Vacuum Science & Technology B* 24, 3227-3229 (2006).

53. Tang, J. Y. et al. Encoding molecular-wire formation within nanoscale sockets. *Angewandte Chemie-International Edition* 46, 3892-3895 (2007).

54. Cord, B., Lutkenhaus, J. & Berggren, K. K. Optimal temperature for development of poly(methylmethacrylate). *Journal of Vacuum Science & Technology B* 25, 2013-2016 (2007).

55. Rooks, M. J. et al. Low stress development of poly (methylmethacrylate) for high aspect ratio structures. *Journal of Vacuum Science & Technology B* 20, 2937-2941 (2002).
56. Schvartzman, M. & Wind, S. J. Robust Pattern Transfer of Nanoimprinted Features for Sub-5-nm Fabrication. *Nano Letters* 9, 3629-3634 (2009).
57. Rothemund, P. W. K. Folding DNA to create nanoscale shapes and patterns. *Nature* 440, 297-302 (2006).
58. Rinker, S., Ke, Y. G., Liu, Y., Chhabra, R. & Yan, H. Self-assembled DNA nanostructures for distance-dependent multivalent ligand-protein binding. *Nature Nanotechnology* 3, 418-422 (2008).
59. Penzo, E., Wang, R., Palma, M. & Wind, S. J. Selective placement of DNA origami on substrates patterned by nanoimprint lithography. *Journal of Vacuum Science & Technology B* in press (2011).
60. Iwase, H., Englund, D. & Vuckovic, J. arxiv. (2008).
61. Englund, D. et al. Controlling cavity reflectivity with a single quantum dot. *Nature* 450, 857-861 (2007).
62. Englund, D. et al. Controlling the spontaneous emission rate of single quantum dots in a two-dimensional photonic crystal. *Physical Review Letters* 95(2005).
63. Faraon, A. et al. Coherent generation of non-classical light on a chip via photon-induced tunnelling and blockade. *Nature Physics* 4, 859-863 (2008)

What is claimed:

1. A nucleoside triphosphate analogue having the structure:

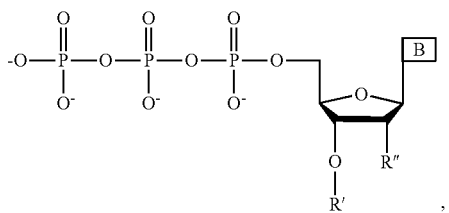

wherein B is a base and is adenine, guanine, cytosine, uracil or thymine,
wherein R" is OH or H, and
wherein R':
(i) comprises an azidomethyl moiety with chemical side groups, wherein said chemical side groups generate a unique or multiple Raman band shifts;
(ii) has a Raman spectroscopy peak with wavenumber from 2000 cm$^{-1}$ to 2300 cm$^{-1}$ or a Fourier transform-infrared spectroscopy peak with wavenumber from 2000 cm$^{-1}$ to 2300 cm$^{-1}$; and
(iii) is cleaved by treatment with a reducing agent, which destroys the N$_3$ group of the azidomethyl moiety with chemical side groups, thereby resulting in a 3'-OH.

2. The nucleoside triphosphate analogue of claim 1 having a Raman spectroscopy peak with wavenumber from 2100 cm$^{-1}$ to 2260 cm$^{-1}$.

3. The nucleoside triphosphate analogue of claim 1, wherein R' has the structure:

(I)

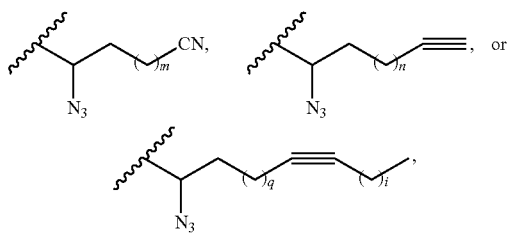

wherein the wavy line indicates the point of attachment of R' to the 3'-O, m is C$_1$-C$_5$, n is C$_1$-C$_5$, q is C$_1$-C$_5$, and i is C$_0$-C$_4$, or (II)

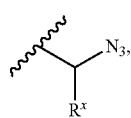

wherein the wavy line represents the point of attachment to the 3' oxygen atom, and R$^x$ is a C$_1$-C$_5$ cyanoalkyl, a C$_1$-C$_5$ alkyl, a C$_2$-C$_5$ alkenyl, or a C$_2$-C$_5$ alkynyl, which is substituted or unsubstituted,
wherein a substituted C$_1$-C$_5$ cyanoalkyl, C$_1$-C$_5$ alkyl, C$_2$-C$_5$ alkenyl, or a C$_2$-C$_5$ alkynyl is a C$_1$-C$_5$ cyanoalkyl, C$_1$-C$_5$ alkyl, C$_2$-C$_5$ alkenyl, or C$_2$-C$_5$ alkynyl in which at least one bond to a hydrogen atom contained therein is replaced by one or more bonds to a non-hydrogen or non-carbon atom with the proviso that normal valencies are maintained.

4. The nucleoside triphosphate analogue of claim 3, wherein R' has the structure:

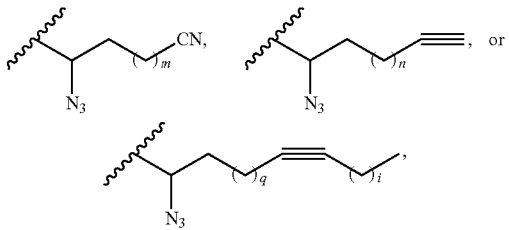

wherein the wavy line indicates the point of attachment of R' to the 3'-O, m is C$_1$-C$_5$, n is C$_1$-C$_5$, q is C$_1$-C$_5$, and i is C$_0$-C$_4$.

5. The nucleoside triphosphate analogue of claim 3, wherein R' has the structure:

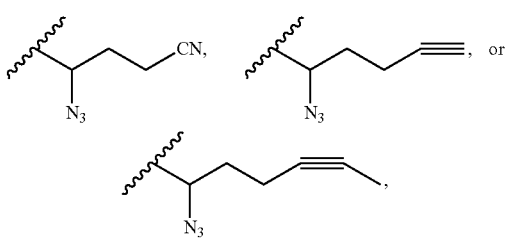

wherein the wavy line indicates the point of attachment to the 3' oxygen atom.

6. The nucleoside triphosphate analogue of claim 3, wherein R' has the structure:

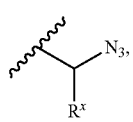

wherein the wavy line represents the point of attachment to the 3' oxygen atom, and R$^x$ is a C$_1$-C$_5$ cyanoalkyl, a C$_1$-C$_5$ alkyl, a C$_2$-C$_5$ alkenyl, or a C$_2$-C$_5$ alkynyl, which is substituted or unsubstituted, wherein a substituted $C_1$-$C_5$ cyanoalkyl, $C_1$-$C_5$ alkyl, $C_2$-$C_5$ alkenyl, or a $C_2$-$C_5$ alkynyl is a $C_1$-$C_5$ cyanoalkyl, $C_1$-$C_5$ alkyl, $C_2$-$C_5$ alkenyl, or $C_2$-$C_5$ alkynyl in which at least one bond to a hydrogen atom contained therein is replaced by one or more bonds to a non-hydrogen or non-carbon atom with the proviso that normal valencies are maintained.

7. The nucleoside triphosphate analogue of claim 3, wherein R" is —H.

8. The nucleoside triphosphate analogue of claim 3, wherein R" is —OH.

9. The nucleoside triphosphate analogue of claim 3, wherein R' has a Raman spectroscopy peak with wavenumber at ~2105 cm−1.

10. The nucleoside triphosphate analogue of claim 3, wherein R' has a Raman spectroscopy peak with wavenumber at ~2138 cm−1.

11. The nucleoside triphosphate analogue of claim 3, wherein R' has a Raman spectroscopy peak with wavenumber at ~2249 cm−1.

12. The nucleoside triphosphate analogue of claim 3, wherein R' has a Raman spectroscopy peak with wavenumber at ~2259 cm−1.

13. The nucleoside triphosphate analogue of claim 3, wherein the reducing agent is aqueous Tris-(2-carboxyethyl) phosphine.

* * * * *